1.

(12) United States Patent
Price et al.

(10) Patent No.: US 6,660,750 B2
(45) Date of Patent: Dec. 9, 2003

(54) FLAVOPIRIDOL METHODS AND COMPOSITIONS FOR HIV THERAPY

(75) Inventors: David H. Price, Iowa City, IA (US); Adrian M. Senderowicz, Rockville, MD (US)

(73) Assignees: University of Iowa Research Foundation, Iowa City, IA (US); The United States of America as represented by the Department of Health and Human Services, Washington, DC (US)

( * ) Notice: Subject to any disclaimer, the term of this patent is extended or adjusted under 35 U.S.C. 154(b) by 13 days.

(21) Appl. No.: 09/784,633

(22) Filed: Feb. 15, 2001

(65) Prior Publication Data

US 2001/0051635 A1 Dec. 13, 2001

Related U.S. Application Data

(60) Provisional application No. 60/182,440, filed on Feb. 15, 2000.

(51) Int. Cl.$^7$ ............................................. A61K 31/445

(52) U.S. Cl. ..................................................... 514/320

(58) Field of Search ......................................... 514/320

(56) References Cited

U.S. PATENT DOCUMENTS

| | | | |
|---|---|---|---|
| 5,284,856 A | 2/1994 | Naik et al. | 514/320 |
| 5,733,920 A | 3/1998 | Mansuri et al. | 514/337 |
| 5,795,909 A | 8/1998 | Shashoua et al. | 514/449 |
| 5,821,072 A | 10/1998 | Schwartz et al. | 435/15 |
| 5,849,733 A | 12/1998 | Kim | 514/212 |
| 5,908,934 A | 6/1999 | Kim | 546/216 |
| 5,919,815 A | 7/1999 | Bradley et al. | 514/449 |
| 5,986,055 A | 11/1999 | Yang et al. | 530/350 |
| 6,013,646 A | 1/2000 | Roder et al. | 514/219 |

FOREIGN PATENT DOCUMENTS

| | | |
|---|---|---|
| WO | WO 96/07409 | 3/1996 |
| WO | WO 97/30174 | 8/1997 |
| WO | WO 99/29730 | 6/1999 |

OTHER PUBLICATIONS

Flores et al. Host–cell P–TEFb kinase activity is essential and limiting for HIV type 1 replication, Proc. Natl. Acad. Sci., USA, 93: 7208–7231, Jun. 1999.*

Sausville et al., Cyclin dependent kinases: initial approach to exploit a novel therapeutic target. Pharmacol. Ther., 82 (2–3): 285–292, 1999.*

Arguello et al., "Flavopiridol induces apoptosis of normal lymphoid cells, causes immunosuppression, and has potent antitumor activity In vivo against human leukemia and lymphoma xenografts," *Blood*, 91:2482–2490, 1998.

Carlson et al., "Flavopiridol induces G1 arrest with inhibition of cyclin–dependent kinase (CDK) 2 and CDK4 in human breast carcinoma cells," *Cancer Res.*, 56:2973–2978, 1996.

Carlson et al., "Down–regulation of cyclin D1 by transcriptional repression in MCF–7 human breast carcinoma cells induced by flavopiridol," *Cancer Res.*, 59:4634–4641, 1999.

Chao et al., "Flavopiridol inhibits P–TEFb and blocks HIV–1 replication," *Jrnl. Biol. Chem.*, 275(37): 28345–28348, 2000.

Cujec et al., "The HIV transactivator Tat binds to the cdk–activating kinase and activates the phosphorylation of the carboxy–terminal domain of RNA polymerase II," *Genes Dev.*, 11:2645–2657, 1997.

De Azevedo et al., "Structural basis for specificity and potency of a flavonoid inhibitor of human CDK2, a cell cycle kinase," *Proc. Natl. Acad. Sci. USA*, 93:2735–40, 1996.

Flores et al., "Host–cell positive transcription elongation factor b kinase activity is essential and limiting for HIV type 1 replication," *Proc. Natl. Acad. Sci. USA*, 96:7208–7213, 1999.

Fujinaga et al., "The ability of positive transcription elongation factor B to transactivate human immunodeficiency virus transcription depends on a functional kinase domain, cyclin T1, and Tat," *J. Virol.*, 72:7154–7159, 1998.

Gray et al., "ATP–site directed inhibitors of cyclin–dependent kinases," *Curr. Med. Chem.*, 6:859–75, 1999; Abstract only.

Kahn et al., "Possible mechanisms of diarrheal side effects associated with the use of a novel chemotherapeutic agent, flavopiridol[1]," *Clin. Cancer Research*, 7:343–349, 2001.

Kim et al., "Structural basis for chemical inhibition of CDK2," *Prog. Cell Cycle Res.*, 2:137–145, 1996; Abstract only.

Li et al., "Induction of apoptosis and inhibition of c–erbB2 in breast cancer cells by flavopiridol", *Clin. Cancer Res.*, 6(1):223–229, 2000.

Li et al., "Induction of growth inhibition and apoptosis in prostate cancer cells by flavopiridol," *Int. J. Oncol.*, 17:755–759, 2000.

Losiewicz et al., "Potent inhibition of CDC2 kinase activity by the flavonoid L86–8275," *Biochem. Biophys. Res. Commun.*, 201:589–595, 1994.

(List continued on next page.)

*Primary Examiner*—Sreeni Padmanabhan
*Assistant Examiner*—Mojdeh Bahar
(74) *Attorney, Agent, or Firm*—Williams, Morgan and Amerson

(57) ABSTRACT

Disclosed is the unexpected discovery that flavopiridol binds tightly to the transcription elongation factor, P-TEFb and dramatically inhibits its activity. As P-TEFb is required for HIV propagation and replication, this invention provides new methods, compositions and kits for the effective treatment of HIV infections and AIDS using flavopiridol, both alone and combination with other therapies.

11 Claims, 7 Drawing Sheets

OTHER PUBLICATIONS

Mancebo et al., "P–TEFb kinase is required for HIV Tat transcriptional activation in vivo and in vitro," *Genes Dev.*, 11:2633–2644, 1997.

Marshall and Price, "Purification of P–TEFb, a transcription factor required for the transition into productive elongation," *J. Biol. Chem.*, 270:12335–12338, 1995.

Marshall et al., "Control of RNA polymerase II elongation potential by a novel carboxyl–terminal domain kinase," *J. Biol. Chem.*, 271:27176–27183, 1996.

Marshall et al., "Regulation of carboxyl–terminal domain phosphatase by HIV–1 Tat protein," *J. Biol. Chem.*, 273:31726–31730, 1998.

McCune, "Animal models of HIV–1 disease," *Science*, 278:2141–2142, 1997.

Meijer, "Cyclin–dependent kinases inhibitors as potential anticancer, antineurodegenerative, antiviral and antiparasitic agents," *Drug Resistance Updates*, 6:83–88, 2000.

Meijer et al., "Properties and potential applications of chemical inhibitors of cyclin–dependent kinases," *Pharmacol.Ther.*, 82(2–3):279–284, 1999.

Melillo et al., "Flavopiridol, a protein kinase inhibitor, down–regulates hypoxic induction of vascular endothelial growth factor expression in human monocytes," *Cancer Res.*, 59:5433–5437, 1999.

Morgan, "Principles of CDK regulation," *Nature*, 374:131–4, 1995.

Morgan, "Cyclin–dependent kinases: engines, clocks, and microprocessors," *Annu. Rev. Cell Dev. Biol.*, 13:261–91, 1997.

Parker et al., "Early induction of apoptosis in Hematopoietic cell lines after exposure to flavopiridol," *Blood*, (91):458–465, 1998.

Patel et al., "Flavopiridol, a novel cyclin–dependent kinase inhibitor, supresses the growth of head and neck squamous cell carcinomas by inducing apoptosis," *J. Clin. Invest.*, 102:1674–1681, 1998.

Peng et al., "Identification of multiple cyclin subunits of human P–TEFb," *genes Dev.*, 12:755–762, 1998.

Price, "P–TEFb, a cyclin–dependent kinase controlling elongation by RNA polymerase II," *Mol. Cell Biol.*, 20:2629–2634, 2000.

Sausville et al., "Cyclin–dependent kinases: initial approaches to exploit a novel therapeutic target," *Pharmacol. Ther.*, 82(2–3):285–292, 1999.

Sausville et al., "Inhibition of CDKs as a therapeutic modality," *Annals New York Academy of Sciences*, 207–222, 2000.

Schnier et al., "Identification of cytosolic aldehyde dehydrogenase 1 from non–small cell lung carcinomas as a flavopiridol–binding protein," *Lett.*, 454:101–104, 1999.

Sedlacek et al., "Flavopiridol (L86–8275, NSC–649890), a new kinase inhibitor for tumor therapy," *International Journal of Oncology*, 9:1143–1168, 1996; Abstract only.

Senderowicz, "Development of cyclin–dependent kinase modulators as novel therapeutic approaches for hematological malignancies," *Leukemia*, 15:1–9, 2001.

Senderowicz and Sausville, "Preclinical development of cyclin–dependent kinase modulators," *J. Natl. Cancer Inst.*, 92:376–387, 2000.

Senderowicz, "Small molecule modulators of cyclin–dependent kinases for cancer therapy," *Oncogene*, 19:6600–6606, 2000.

Senderowicz, "Flavopiridol: the first cyclin–dependent kinase inhibitor in human clinical trials," *Investigational New Drugs*, 17:313–320, 1999.

Senderowicz et al., "Phase I trial of continuous infusion flavopiridol, a novel cyclin– dependent kinase inhibitor, in patients with refractory neoplasms," *J. Clin. Oncol.*, 16:2986–2999, 1998.

Senderowicz et al., "Decreased transcription of cyclin D1 induced by a cyclin dependent kinase inhibitor, flavopiridol, " *In Proc. Eighty–Eightieth Annual Meeting of the American Association of Cancer Research. San Diego, CA.*, 1997.

Singh et al., "Cyclin D1 and Cdk6 are the targets for flavopiridol–mediated G1 block in MCF10A breast epithelial cell line," *Proceedings of the American Association for Cancer Research Annual Meeting*, 40:28, 1999.

Wimmer et al., "Interactions between Tat and TAR and human immunodeficiency virus replication are facilitated by human cyclin T1 but not cyclins T2a or T2b," *Virology*, 255:182–189, 1999.

Yao and Browning, "Potential use of flavopiridol to treat HHV–8–associated malignancies," *Blood*, 92 (10 Suppl. 1 Part 1–2):539A, 1998.

Zhou et al., "Tat modifies the activity of CDK9 to phosphorylate serine 5 of the RNA polymerase II carboxyl–terminal domain during human immunodeficiency virus type 1 transcription," *Mol. Cell Biol.*, 20:5077–5086, 2000.

Zhu et al., "Transcription elongation factor P–TEFb is required for HIV–1 tat transactivation in vitro," *Genes Dev.*, 11:2622–2632, 1997.

International Search Report for PCT/US01/04898, mailed May 28, 2001.

* cited by examiner

FLAVOPIRIDOL METHODS AND COMPOSITIONS FOR HIV THERAPY

The present application claims priority to U.S. provisional application Ser. No. 60/182,440, filed Feb. 15, 2000, the entire specification, claims and figures of which are incorporated herein by reference without disclaimer.

Adrian M. Senderowicz is employed at the Oral Pharyngeal Cancer Branch, Division of Intramural Research, National Institute of Craniofacial and Dental Disorders (NIDCR), National Institutes of Health (NIH), U.S.A. The U.S. Government also owns rights in the present invention pursuant to grants AI43691 and GM35500 to David H. Price from the NIH.

BACKGROUND OF THE INVENTION

1. Field of the Invention

The present invention relates generally to the fields of kinase inhibitors, transcription and virology. More particularly, it concerns the surprising discovery that flavopiridol dramatically inhibits the transcription elongation factor, P-TEFb. As P-TEFb is essential for HIV productive infection, the present invention provides new, effective methods, compositions and kits for treating HIV infections and AIDS using flavopiridol and combinations thereof.

2. Description of Related Art

The Human Immunodeficiency Virus (HIV) is a retrovirus that productively infects human and primate cells. In humans, infection with HIV is life-threatening and leads to AIDS, the terminal syndrome due to HIV infection. Although HIV has been the subject of intense biomedical and clinical research, there are still few effective therapies for use against HIV infection and AIDS. In certain areas of the world, HIV is particularly prevalent; for example, in Africa, one out of every four adults reportedly carries the HIV virus. HIV infection, and the resultant AIDS syndrome, are thus unfortunately widespread and continue to exert a significant toll in human suffering and economic terms.

There are about 15 therapeutics currently approved for administration to patients with HIV. Most of these are either protease inhibitors, such as Saquinavir, the first protease inhibitor approved for treatment of HIV (under the name, Invirase™); or nucleoside reverse transcriptase inhibitors, including AZT (marketed as Retrovir™). Unfortunately, the effectiveness of even the most potent and specific drugs, those that inhibit a required HIV protease, is limited as resistant strains arise quickly. In fact, treatment with current drugs has been reported to stimulate the selection and propagation of resistant viral strains. It has therefore been suggested that the most effective treatments are those incorporating a combinatorial use of different drugs. However, these treatments can lead to dose-limiting toxicity and significant side-effects, limiting their application.

Therefore, there remains in the art an evident need for new and more effective anti-HIV agents. Within this general desire, the identification of drugs other than protease inhibitors and nucleoside reverse transcriptase and drugs that target other important process in the HIV life cycle are needed. The identification of a drug that acts against a cellular target would be an important advance in the field, particularly as such a drug would make it difficult for resistant strains to arise.

SUMMARY OF THE INVENTION

The present invention addresses the foregoing long-felt need and other deficiencies in the art by identifying new and effective strategies for treating viral infections, particularly HIV infections and AIDS. The invention is based, in part, upon the discovery that the compound flavopiridol, used in clinical trials for the treatment of cancer, dramatically inhibits the transcription elongation factor, P-TEFb. As P-TEFb is required for HIV propagation and replication in human cells, flavopiridol compounds can now be used to inhibit cellular P-TEFb, thus interfering with HIV replication and providing new treatments for HIV infections and AIDS.

The invention thus provides new methods, compositions, kits and uses for treating HIV infections and AIDS using flavopiridol compounds and, optionally, combinations of such compounds with other HIV therapeutics. One particularly surprising aspect of this invention is the fact that the cellular targets for flavopiridol action were thought to have been identified, leaving no motivation to search for other candidate molecules to which flavopiridol may bind or inhibit.

A further unexpected benefit of the invention is the ability of flavopiridol to inhibit P-TEFb, and consequent HIV infection, at extremely low concentrations. This allows flavopiridol compounds to be used in HIV treatment at concentrations that are much lower than those employed to produce an anti-tumor effect, thus providing HIV and AIDS treatments with reduced or absent side-effects and toxicities. In fact, the effectiveness of flavopiridol in inhibiting P-TEFb and HIV infection is such that the present invention provides pharmaceutical compositions comprising surprisingly low, but nonetheless therapeutically effective, levels of flavopiridol.

The invention thus provides a variety of flavopiridol-based compositions and methods for inhibiting the enzyme complex P-TEFb (positive transcription elongation factor b). As used herein, unless otherwise stated or evident from scientific usage, the term "P-TEFb" is employed to mean a functional, operative enzyme complex with biological activity. In structural terms, the P-TEFb enzyme complex is comprised of a cyclin-dependent kinase subunit (Cdk9) and a larger, cyclin subunit (cyclin T1). Again, unless otherwise stated or scientifically evident, the "P-TEFb" of the present disclosure comprises both the kinase (Cdk9) and cyclin (cyclin T1) subunits.

According to the convention in the art, as used herein, unless otherwise stated or made evident, the term "HIV" is often used succinctly to refer to "HIV-1". Those of ordinary skill in the art will understand that where "HIV-2" is particularly intended, this will be recited. In the absence of such direction, "HIV" may include "HIV-1 and HIV-2", with "HIV-1" being particularly preferred for treatment by the invention.

Currently, the most preferred flavopiridol-like compound is flavopiridol itself. Flavopiridol is 4H-1-Benzopyran-4-one,2-(2-chlorophenyl)-5,7-dihydroxy-8-(3-hydroxy-1-methyl-4-piperidinyl)-, hydrochloride, (−)-cis-; which may also be termed (−)-cis-2-(2-chlorophenyl)-5,7-dihydroxy-8-[4R(3 S-hydroxy-1-methyl)piperidinyl]-4H-1-benzopyran-4-one, hydrochloride.

However, those of ordinary skill in the art will understand that the present invention is by no means limited to the use of flavopiridol itself, but encompasses a range of "flavopiridol-like compounds", such as analogs and derivatives. Exemplary flavopiridol compounds other than the parent flavopiridol compound include 2-thio and 2-oxo flavopiridol analogs. Any flavopiridol-based compound may be used in the invention so long as it inhibits P-TEFb in at least substantially the same manner as flavopiridol itself.

Given the mechanistic studies provided herein, flavopiridol compounds that inhibit P-TEFb to a greater extent, and/or with other advantageous properties, can now be designed and used in the present invention.

Irrespective of the source of the flavopiridol-based compounds, the invention particularly contemplates the use of one, two, three or four distinct flavopiridol analogues or derivatives, up to and including a plurality of such compounds. This exemplifies the use of singular terminology throughout the entire application, wherein the terms "a" and "an" are used in the sense that they mean "at least one", "at least a first", "one or more" or "a plurality" of the referenced components or steps, except in instances wherein an upper limit is thereafter specifically stated or would be understood by one of ordinary skill in the art. The operable limits and parameters of combinations, as with the amounts of any single agent, will be known to those of ordinary skill in the art in light of the present disclosure.

By the term "inhibiting", it is meant that practice of the present invention results in the "inhibition" of P-TEFb, preferably the inhibition of one or more of the "biological activities" of P-TEFb. Most preferably, the inhibition takes the form of ultimately inhibiting the role of P-TEFb in transcription.

Although by no means bound by the following mechanism, the present inventors believe that the invention functions due to the inhibition of the cyclin-dependent kinase (cdk9) subunit of P-TEFb. Once inhibited, the cdk9 kinase subunit is unable to effectively phosphorylate RNA polymerase II, thus inhibiting transcription. However, any form of "inhibition" of P-TEFb is encompassed by the present invention. As advantageous aspects of the invention concern net inhibitory effects observed at the whole cell or whole animal level, an understanding of the precise molecular mechanism by which the invention operates, although of scientific interest, is not necessary to practice the invention as disclosed herein.

In order to inhibit P-TEFb in accordance with the invention, the inhibitory methods may be conducted at the sub-cellular or cellular levels or in the context of the whole animal, including clinical treatment. All such methods involve the "provision" of at least a first flavopiridol compound to the environment of the P-TEFb in a manner effective to "contact" the P-TEFb with an effective inhibitory amount of the flavopiridol compound.

One method to inhibit P-TEFb comprises contacting "cell-free P-TEFb", i.e., contacting a cell-free composition that comprises P-TEFb, with an effective inhibitory amount of at least a first flavopiridol compound. The operation of such methods generally involves providing to a cell-free system that comprises P-TEFb an amount of a flavopiridol compound effective to inhibit the cyclin-dependent kinase (cdk9) subunit of P-TEFb.

In such sub-cellular methods, the cell-free system may comprise components effective to achieve measurable RNA polymerase II phosphorylation. The inhibition of P-TEFb activity can thus be readily determined by measuring the inhibition of RNA polymerase II phosphorylation in the cell-free system. Preferably, in such methods, the cell-free system comprises components effective to perform measurable in vitro transcription, whereby the inhibition of P-TEFb may be readily determined by measuring the inhibition of transcription elongation in the cell-free system. Such "kinase" and "transcription" assays are known to those of ordinary skill in the art and are further described herein.

In other in vitro embodiments, the inhibitory methods of the invention are performed using intact cells and populations thereof. Examples of such methods include those for generally inhibiting transcription, which comprise providing to a cell capable of supporting transcription an amount of at least a first flavopiridol compound effective to inhibit transcription in the cell. The inhibition of transcription in this manner is particularly embodied by inhibiting transcription via RNA polymerase II.

The foregoing and other sub-cellular and cellular inhibitory methods of the invention, including the "kinase" and "transcription" inhibition, have definite practical uses, such as in providing reliable controls for performing in vitro studies, known to be necessary components in drug screening assays and the like.

In further embodiments, the invention provides compositions and methods for inhibiting P-TEFb in which the flavopiridol compound is provided to a virally-infected cell, resulting in the inhibition of the cdk9 subunit of the P-TEFb within the cell. These methods are intelligently applied in inhibiting viral transcription, in which the flavopiridol compound is provided to a cell capable of supporting viral transcription and wherein viral transcription is inhibited in the cell.

The cells and virally-infected cells to be acted upon by the invention are preferably mammalian cells, although they need not be, with particular examples being primate and human cells. Other aspects of the invention are therefore human cells, and populations thereof, comprising components of an HIV virus and a biologically effective amount of at least a first flavopiridol compound.

The inhibition of viral transcription may be performed in vitro, such that at least a first flavopiridol compound is provided to a system or cell competent to perform viral transcription, resulting in inhibition of viral transcription. An exemplary "system competent to perform viral transcription" is a cell comprising a genetic construct that expresses a reporter gene from a viral promoter. The inhibition of viral transcription in such a cell or system is readily determined by measuring the inhibition of reporter gene expression in the cell or system. Such methods are exemplified using HIV transcription and CMV transcription, but are widely applicable to a range of viral transcription.

Throughout the methods of the invention, an "effective inhibitory amount" is an amount of at least a first flavopiridol compound effective to inhibit, and preferably to significantly inhibit, P-TEFb. The effective inhibitory amounts are thus also amounts effective to inhibit, and preferably to significantly inhibit, a biological activity of P-TEFb, such as inhibiting transcription, and preferably, inhibiting viral transcription. More preferably, the effective inhibitory amounts are amounts of flavopiridol compounds effective to inhibit, and preferably to significantly inhibit, viral transcription, replication and/or propagation in virally-infected cells. Any degree of inhibition is sufficient to satisfy the invention, although those of ordinary skill in the art will understand the inhibition levels that are sufficient to indicate preferred in vitro and in vivo inhibition.

"Inhibition" requires a "reproducible", i.e., consistently observed, inhibition in one or more of the foregoing parameters. A "significant inhibition" is a reproducible or consistently observed significant inhibition in one or more of the foregoing parameters, such as a reproducible inhibition of at least about 45%, about 50%, about 55%, about 60%, about 65%, about 70%, about 75% or about 80% in comparison to control levels, i.e., in the absence of flavopiridol. Although not required to practice the invention, inhibition levels of at least about 85%, about 90%, about 95% or even higher are by no means excluded.

Further methods of the invention concern the "differential inhibition" of cellular or host gene transcription as opposed to viral gene transcription. As the present invention shows a surprisingly effective degree of differential inhibition, particularly in terms of HIV infection of human cells, all that is required to practice these aspects of the invention is to provide to a cell capable of supporting host and viral transcription an amount of at least a first flavopiridol compound effective to inhibit viral gene transcription in preference to cellular or host gene transcription in the cell.

Such is the basic meaning of a "differentially inhibiting amount", as used herein. Preferably, a "differentially inhibiting amount" is an amount of at least a first flavopiridol compound effective to significantly inhibit viral transcription, replication and/or propagation in virally-infected cells of a host without significantly inhibiting host cell gene transcription and cellular function in equivalent, non-virally-infected host cells.

Although by no means a requirement of the invention, the differential inhibition methods provide for certain important uses of this discovery. The inhibition of viral gene transcription to a greater degree than host cell gene transcription supports the in vitro and in vivo anti-viral methods and compositions of the present invention.

Accordingly, the invention provides methods for inhibiting viral gene transcription, comprising providing to a virally-infected cell an amount of at least a first flavopiridol compound effective to inhibit the cdk9 subunit of P-TEFb within the cell, thus inhibiting viral transcription in the cell. Important target cells in these aspects are HIV-1-infected cells. However, as P-TEFb is required for HIV-2, EIAV (equine infections anemia virus), SIV (simian immunodeficiency virus) and BIV (bovine immunodeficiency virus) functions in host cells, the present invention provides effective compositions and methods to inhibit viral gene transcription in cells and animals infected with HIV-2, EIAV, SIV and BIV.

As viral transcription is an essential step of viral replication and propagation, the present invention further provides compositions and methods for inhibiting viral replication and/or propagation. Such methods generally comprise providing to a cell infected, or suspected of being infected, with a virus an amount of at least a first flavopiridol compound effective to inhibit P-TEFb within the cell, thereby inhibiting viral transcription, replication and/or propagation in the cell. Preferred aspects of the invention again concern the inhibition of HIV-1 replication and/or propagation, although inhibiting the replication and/or propagation of viruses such as HIV-2, EIAV, SIV and BIV is encompassed by the present invention.

The inhibition of viral transcription, replication and/or propagation is unified in that it may be achieved in vitro or in vivo. To practice these aspects of the invention in vivo, the virally-infected cell is located within an animal or patient and the at least a first flavopiridol compound is provided to the animal or patient in a manner and an amount effective to contact the virally-infected cell with the inhibitory flavopiridol compound. Preferably, the amount is an amount effective to inhibit viral transcription, replication and/or propagation in virally-infected cells of the animal. More preferably, the amount is a differentially inhibiting amount that is effective to significantly inhibit viral transcription, replication and/or propagation in virally-infected cells of the animal without significantly inhibiting host cell gene transcription or cellular integrity.

Accordingly, the invention provides compositions and methods for inhibiting P-TEFb in an animal or patient, which generally comprise providing to an animal or patient having, suspected of having, or at risk for developing a viral infection, an amount of at least a first flavopiridol compound effective to inhibit P-TEFb within cells of the animal or patient.

Execution of these methods leads to methods for preventing or treating a viral infection, comprising providing to an animal or patient having, suspected of having, or at risk for developing a viral infection, an amount of at least a first flavopiridol compound effective to inhibit P-TEFb within cells of the animal or patient, thereby preventing or treating the viral infection. The P-TEFb should particularly be inhibited within the virally infected or susceptible cells of the animal or patient, as exemplified by the inhibition of P-TEFb within T cells and/or macrophages, which are infected, or are susceptible to infection, by HIV-1.

The animals to be treated by the invention are preferably mammals or primates, with the invention being particularly suitable for treating HIV-1, HIV-2, EIAV, SIV and BIV infections and the associated and resultant diseases.

The treatment of humans with HIV-1 infections and resultant diseases is particularly preferred. Accordingly, the invention provides methods for preventing or treating an HIV-1 infection, comprising providing to a subject or patient having, suspected of having, or at risk for developing an HIV-1 infection, an amount of at least a first flavopiridol compound effective to inhibit P-TEFb within cells of the subject or patient, thereby preventing or treating the HIV-1 infection.

Where "prevention" is concerned, whether of HIV-1 or other viral infections, the amounts of flavopiridol compounds are "prophylactically effective amounts", such that they are effective to inhibit P-TEFb within cells of the animal or subject, thereby preventing or retarding the development of the infection, lessening its severity and/or duration or such like. Where "treatment" is concerned, whether of HIV-1 or other viral infections, the amounts of flavopiridol compounds are "therapeutically effective amounts", such that they are effective to inhibit P-TEFb within cells of the animal or patient, thereby treating the infection, as exemplified by alleviating symptoms, lessening the severity and/or duration of the infection, up to and including curing the infection or disease.

In certain aspects, the invention thus provides methods for slowing or preventing an HIV infection, comprising identifying a subject at risk for developing an HIV infection and administering to the subject a prophylactically effective amount of at least a first flavopiridol compound. Methods for slowing or preventing the progression of an HIV infection into full-blown AIDS are also provided, comprising providing to a patient having an HIV infection an amount of at least a first flavopiridol compound effective to inhibit P-TEFb within cells of the patient, thereby slowing or preventing the progression of the HIV infection into full-blown AIDS.

Other methods are those for treating an HIV infection, comprising providing to a subject having or suspected of having an HIV infection an amount of at least a first flavopiridol compound effective to inhibit P-TEFb within T cells and/or macrophages of the subject, thereby treating the HIV infection. Other methods for treating a patient with an HIV infection, comprise providing at least a first flavopiridol compound to such a patient in an amount and for a period of time effective to inhibit the cyclin-dependent kinase (cdk9) subunit of P-TEFb within HIV-infected cells of the patient, thereby inhibiting HIV replication or HIV propagation in the patient.

Yet further methods of the invention are those for treating patients with an AIDS related illness or full-blown AIDS, comprising providing to the patient an amount of one or more flavopiridol compounds effective to inhibit P-TEFb within a number of cells of the patient sufficient to exert a therapeutic effect in the patient. The patients may be identified or pre-selected by any one or more of a number of means.

Given the effectiveness of the invention, another advantage is that it provides compositions and methods for treating patients infected with a strain of HIV-1 that is at least moderately resistant to at least a first available anti-HIV therapeutic agent. These methods extend to the treatment of patients infected with a strain of HIV that is substantially resistant to at least a moderate number of available anti-HIV therapeutic agents.

The foregoing "prophylactically and therapeutically effective amounts" are thus encompassed within the terms "biologically effective amounts" and "effective inhibitory amounts" of flavopiridol compounds. All such "effective amounts" are amounts of flavopiridol compounds effective to produce some, and preferably some significant, benefit upon administration to an animal or patient. The benefits include reducing symptoms, severity and/or duration, as well as lessening the chance of transmission and other veterinary and clinical benefits.

It will be understood that the more significant the disease to be treated, the more side-effects that can likely be tolerated. Equally, where the disease to be treated is not particularly significant or life-threatening, the lack of side-effects should be more stringently pursued.

Appropriate doses will be known those of ordinary skill in the art in light of the present disclosure. For example, suitable doses of flavopiridol compounds are those provided to patients in an amount between about 4 mg/m$^2$/day IV over 72 hours (5 mg/kg PO) and about 50 mg/m$^2$/day IV over 72 hours (25 mg/kg PO); between about 12 mg/m$^2$/day IV over 72 hours (10 mg/kg PO) and about 28 mg/m$^2$/day IV over 72 hours (20 mg/kg PO); and between about 8 mg/m$^2$/day IV over 72 hours (8 mg/kg PO) and about 16 mg/m$^2$/day IV over 72 hours (15 mg/kg PO). Further suitable doses are those effective to produce a peak plasma concentration of between about 30 nM and about 60 nM upon administration to a human subject.

The routes of administration that may be used in the present invention are virtually limitless, so long as an effective amount of at least a first flavopiridol compound can be provided thereby. Exemplary means include ingestible, oral administration and parenteral administration, such as by intranasal administration, subcutaneous injection, intravenous injection or continuous infusion.

All such compositions and methods of the invention may be combined for use with one or more other anti-viral agents, such as at least a second, third, fourth or fifth, anti-HIV agent or at least a first, second, third or fourth anti-AIDS therapeutic agent. A plurality of distinct anti-HIV or anti-AIDS therapeutic agents may be administered to an animal or patient, up to and including the dose limiting toxicity of the combination. The invention can thus be used to form synergistic combinations with other therapies and/or known agents, particularly those methods and agents that previously failed to achieve maximal effectiveness in vivo, perhaps due to dose-limiting toxicity and/or viral resistance.

In terms of anti-HIV and anti-AIDS therapeutic agents, certain preferred compounds include nucleoside analogue reverse transcriptase inhibitors (NRTIs) and protease inhibitors. Particular exemplary compounds include those selected from the group consisting of amprenavir (Agenerase™); the VX-175/GW433908 prodrug of amprenavir (Agenerase™); Combivir®; indinavir (Crixivan™); lamivudine (3TC, Epivir™); saquinavir (Invirase™ or Fortovase™); zalcitabine (ddC, Hivid™); hydroxyurea (Hydrea™); ritonavir (Norvir™); adefovir dipivoxil (Preveon™); delavirdine (Rescripto™); AZT (zidovudine, Retrovir™); efavirenz (Sustiva™); didanosine (ddI, Videx™); nelfinavir (Viracept™); nevirapine (Viramune™); stavudine (d4T, Zerit™); abacavir (Ziagen™); capravirine (AG1549) and emivirine (MKC-442, Coactinon®).

In such combination therapies, the at least a first flavopiridol compound and at least a second anti-HIV or anti-AIDS therapeutic agent may be administered to the animal or patient substantially simultaneously, such as from a single pharmaceutical formulation or two distinct pharmaceutical formulations. Alternatively, the at least a first flavopiridol compound and at least a second anti-HIV or anti-AIDS therapeutic agent may be administered to the animal or patient sequentially, such as on alternate days.

In further embodiments, the invention provides a range of therapeutic kits. Certain kits comprise a therapeutically effective amount of at least a first flavopiridol compound and instructions for administering the flavopiridol compound to an animal or subject having or at risk for developing an viral infection, HIV infection or AIDS. Such kits may be combined with effective amounts of at least one diagnostic agent that detects a viral, HIV infection or AIDS; or with a therapeutically effective amount of at least one other anti-viral, anti-HIV or anti-AIDS therapeutic agent.

Certain other therapeutic kits of the invention comprise an effective amount of at least a first flavopiridol compound and an effective amount of at least one diagnostic agent that detects a viral, HIV infection or AIDS; or an effective amount of at least one, two, three, four or any number of other anti-viral, anti-HIV or anti-AIDS therapeutic agents. Instructions may also be combined with these kits. Other biological agents or components may be included, such as those for making and using the drugs.

Exemplary diagnostic agents include molecular biological agents that detect at least a first HIV nucleic acid; at least a first antibody that detects at least a first HIV protein or peptide; and at least a first HIV protein or peptide that detects at least a first antibody that binds to an HIV protein or peptide. The range of additional therapeutic agents will be known those of ordinary skill in the art in light of the present disclosure, as exemplified by those described herein.

In such kits, the diagnostic agents are preferably disposed within a distinct container of the kit. The combined therapeutic agents, however, may be combined within a single container of the kit, i.e., in the same composition as the flavopiridol compound, such as in a cocktail or admixture. They may alternatively be maintained separately from the flavopiridol compound, in a distinct container.

The invention thus provides combination therapeutics comprising, in any pharmaceutically acceptable form, a therapeutically effective amount of a flavopiridol compound in combination with a therapeutically effective amount of at least a second anti-viral, anti-HIV or anti-AIDS therapeutic agent. Also provided are medicinal cocktails comprising, in any pharmaceutically acceptable form, a combined therapeutically effective amount of flavopiridol or a flavopiridol analog or derivative and a plurality of distinct anti-viral, anti-HIV or anti-AIDS therapeutic agents.

Further important aspects of the invention are compositions comprising a dilute solution of at least a first flavopiridol compound, optionally in combination with a pharmaceutically acceptable excipient, e.g., one suitable for oral or intranasal administration, or for parenteral administration, such as intravenous or subcutaneous injection or continuous infusion. Such compositions may comprise at least a first flavopiridol compound at a concentration of between about 0.01 mg/ml and about 0.04 mg/ml.

Particular novel and inventive compositions of the invention are those comprising a therapeutically effective amount of at least a first flavopiridol compound formulated for oral administration and those comprising a therapeutically effective amount of at least a first flavopiridol compound formulated for intranasal administration.

Yet further compositions of the invention are those comprising at least a first flavopiridol or flavopiridol analog formulated in a unit low dose solution for any type of administration. Exemplary unit low dose flavopiridol solutions are those effective to significantly inhibit the cyclin-dependent kinase (cdk9) of P-TEFb without significantly inhibiting other cyclin-dependent kinases. Further exemplary compositions are those comprising a solution of at least a first flavopiridol compound effective to produce a peak plasma concentration of between about 30 nM and about 60 nM upon administration to a human subject.

Naturally, the invention further provides any type of flavopiridol composition for use in treating a viral or HIV infection or AIDS. The invention yet further provides for the use of any type of flavopiridol composition in the manufacture of a medicament for use in treating a viral or HIV infection or AIDS. Combined uses and medicaments in which a flavopiridol compound is one component of a therapeutic approach are also encompassed within the present invention.

BRIEF DESCRIPTION OF THE DRAWING

The following drawing forms part of the present specification and is included to further demonstrate certain aspects of the present invention. The invention may be better understood by reference to the drawing in combination with the detailed description of specific embodiments presented herein.

FIG. 2A, 10 $\mu$M ATP; FIG. 2B, 30 $\mu$M ATP; FIG. 2C, 100 $\mu$M ATP and FIG. 2D, 300 $\mu$M ATP. Autoradiographs of the SDS gels in which the phosphorylated polymerase was resolved allowed the positions of the hypophosphorylated (IIa) and hyperphosphorylated (IIo) forms of the large subunit RNA polymerase II to be distinguished from reactions containing between 0 and 300 nM flavopiridol. The extent of phosphorylation was quantitated from dried gels with an InstantImager™ (Packard). The $IC_{50}$ values were calculated by fitting the data to a logistic dose-response curve using the program TableCurve™ (Jandel Scientific). Each inhibition curve was performed more than twice on different days with the same results.

FIG. 4A, effect of flavopiridol on the single round of infection in Sx22-1 indicator cells. The HIV1$_{HXB2}$ viral isolate was used. It was transfected into 293T cells and high viral titers were observed. 50 $\mu$l of the viral stock was added to $10^4$ Sx22-1 cells, which contain one copy of the HIV LTR linked to the $\beta$-galactosidase (lacZ) reporter gene (Fackler et al., 1997). Cells were incubated for 5 hours to allow for entry and integration of HIV-1, washed and grown for an additional 36 hours before being fixed and stained for $\beta$-galactosidase by standard protocols (Fackler et al., 1997). Flavopiridol was added to the culture 12 hours prior to the infection (at the concentrations shown) and cells were grown in its presence for the duration of the assay. The plot shows the number of blue cells in one well of a 96-well culture plate versus the concentration of flavopiridol. The study was repeated three times and the mean and standard deviations are plotted.

FIG. 4B, effect of flavopiridol on viral spread and replication in Jurkat cells using the multiple round viral spread assay. In the presence of 10 $\mu$g of Polybrene, HIV-1$_{NL-3}$ viral particles (containing 2 ng of p24$^{gag}$) were added to 5×10$^4$ Jurkat cells. After 5 hours, virus was removed by extensive washing. Flavopiridol was added at the indicated concentrations from 1.5 to 25 nM. On days 2, 5, 8, 11 and 15, supernatants were collected and cells were incubated with fresh medium and flavopiridol. Reverse transcriptase was measured on 10 supernatant. With the high multiplicity of infection used, most Jurkat cells were killed after 10 days of infection and viral titers returned to base-line levels. Results are representative of two infections performed in duplicate where the standard errors of the mean were less than 20%.

FIG. 5A, kinase assay using RNA polymerase I as a substrate; FIG. 5B, kinase assay using the negative transcription elongation factor, DSIF, as a substrate; FIG. 5C, a plot of the $IC_{50}$ calculated versus the relative amounts of P-TEFb.

DESCRIPTION OF ILLUSTRATIVE EMBODIMENTS

Figure 1:
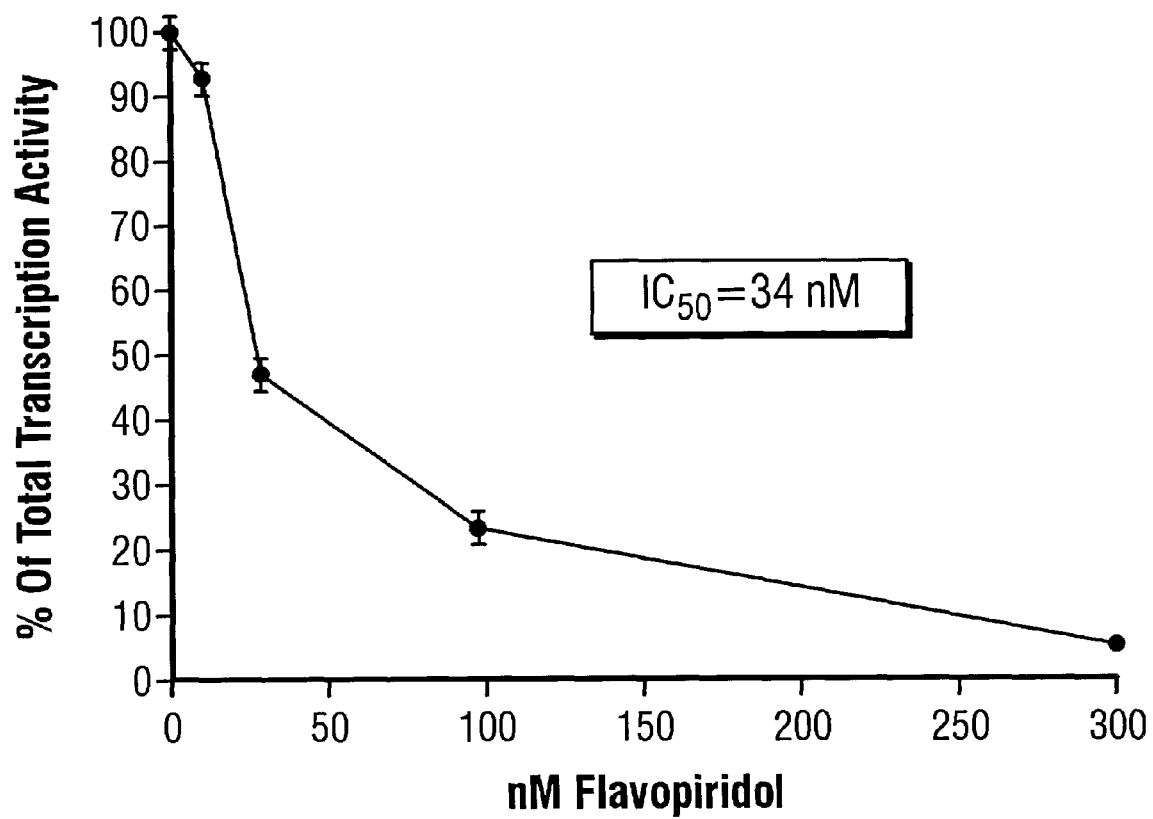
FIG. 1. Inhibitory effects of flavopiridol on transcription by targeting P-TEFb. Reactions were carried out with the modified pulse-chase protocol using the CMV promoter (Peng et al., 1998a). Flavopiridol was added during pre-incubation step. The run-off transcripts synthesized in the presence of the indicated concentrations of flavopiridol were analyzed (using a 6% gel) and quantitated with an InstantImager™ (Packard). The $IC_{50}=33.6$ nM.

The HIV epidemic is a growing international concern. There remains today a significant need to develop new therapeutics to combat the devastating effects of HIV infection and the resultant disease state, AIDS. The present invention makes a significant contribution to this endeavor, in part facilitated by linking diverse aspects of cellular biology, not previously connected in the art. The invention centers on the surprising discovery that the transcription elongation factor, P-TEFb is a primary cellular target for the inhibitory actions of the candidate anti-cancer drug, flavopiridol. As P-TEFb is essential for HIV replication in human cells, the ability of low levels of flavopiridol to inhibit P-TEFb opens up important new avenues of therapeutic intervention.

Flavopiridol is a flavonoid compound that has antiproliferative properties and is currently being tested in clinical trials against cancer (Senderowicz and Sausville, 2000). The present inventors discovered that flavopiridol blocks transcription in vitro and in vivo and that these effects are mediated by inhibition of P-TEFb. Flavopiridol inhibits the kinase activity of P-TEFb with a Ki of about 3 nM and is not competitive with ATP. P-TEFb is a cellular cofactor required for productive HIV infection and the present invention demonstrates the actual inhibition of HIV infection by very low levels of flavopiridol. The use of flavopiridol and flavopiridol analogs as therapeutic agents against AIDS, both alone and in combination with other agents, is thus provided by the instant invention.

I. P-TEFb

The focus of the present invention on P-TEFb is in the context of the requirement for P-TEFb as a cellular cofactor for HIV replication. P-TEFb, comprised of Cdk9 and cyclin T1, has other important cellular roles, as discussed below.

The elongation phase of transcription by RNA polymerase II is one of the many steps during the generation of mature mRNAs that is subject to regulation. Shortly after initiation, RNA polymerase II comes under the control of negative transcription elongation factors, generally termed N-TEF, and enters abortive elongation (Marshall and Price, 1992; Shilatifard, 1998b). During this post-initiation process only short, prematurely terminated transcripts are generated. Such short transcripts arise from transcription of many genes, including c-myb, c-myc, c-fos, HSP70, and the HIV-LTR, and are normally subject to rapid degradation (Marshall and Price, 1992; Bentley, 1995; Reines et al., 1999).

Productive elongation generating long transcripts from which mRNAs are derived, i.e., escape from the action of N-TEF, requires the action of a positive transcription elongation factor (P-TEFb) (Marshall and Price, 1995). P-TEFb suppresses the effects of N-TEF, allows the transition from abortive elongation to productive elongation, and is the only factor shown to do so (Marshall et al., 1996). In this way, the fraction of initiating RNA polymerase II molecules that produce full length transcripts is controlled by a selection process that occurs early in the elongation phase of the transcription cycle. After the transition is made into productive elongation the efficiency of elongation may be influenced by additional factors, including S-II, TFIIF, ELL and elongin (Reines et al., 1996; Shilatifard, 1998a).

A. Identification of P-TEFb

The elongation control process was uncovered during studies aimed at understanding the mechanism of inhibition of transcription by 5,6-dichloro-1-β-D-ribofuranosylbenzimidazole (DRB). Treatment of mammalian cells with DRB is lethal, however, the initial effect is a dramatic reduction of mRNA (Sehgal et al., 1976). DRB treatment caused the production of shortened transcripts from a variety of genes, suggesting that elongation by RNA polymerase II was affected (Tamm et al., 1980). This interpretation was complicated by the finding that DRB had no effect on the enzymatic activity of purified RNA polymerase II (Kephart et al., 1992).

Fortunately, DRB did affect transcription by RNA polymerase II in vitro when crude nuclear extracts were used (Chodosh et al., 1989; Zandomeni et al, 1982). A number of promoters were surveyed using a Drosophila in vitro transcription system and it was found that most of the RNA polymerase II molecules that initiated generated only short transcripts (Marshall and Price, 1992). Those polymerases that were able to reach the end of the template could not do so in the presence of DRB (Marshall and Price, 1992). Inhibition of the appearance of runoff transcripts by DRB became the hallmark of elongation control and made the requirement for P-TEFb apparent.

Examination of RNA polymerase II elongation using pulse/chase techniques or immobilized templates led to the elucidation of the general parameters of N-TEF and P-TEF function. The effects of N-TEF were suppressed by the addition of high salt or detergents, so that all polymerases that initiated were able to reach runoff length (Kephart et al., 1992). P-TEF was a limiting factor because under normal salt conditions in the functional presence of N-TEF only a small fraction of the polymerases were able to reach runoff (Marshall and Price, 1992).

Kinetic analysis indicated that polymerases initiated and then generated a pattern of short transcripts within 30 seconds and that runoff transcripts accumulated only after several minutes (Marshall and Price, 1992). This led to the model in which P-TEF was suggested to interact with the early elongation complexes after they were stopped by N-TEF and then after a period of time caused the suppression of the action of N-TEF (Marshall and Price, 1992). Early elongation complexes generated on immobilized templates and washed with low salt retained their inability to generate long transcripts (Marshall and Price, 1992). Transcription with gently washed preinitiation complexes indicated that N-TEF, but not P-TEF was retained (Marshall and Price, 1992).

The first and only known component of P-TEF, P-TEFb, was first identified and purified using an in vitro reconstitution assay. Drosophila $K_c$ cell nuclear extract was subjected to chromatographic fractionation and fractions containing two co-eluting polypeptides were found to stimulate the appearance of DRB-sensitive runoff transcripts (Marshall and Price, 1995). Shortly after its purification, P-TEFb was found to have protein kinase activity (Marshall et al., 1996). It was able to efficiently phosphorylate the carboxyl terminal domain (CTD) of the large subunit of RNA polymerase II when either pure polymerase or isolated early elongation complexes were used as substrate. Kinetic analysis indicated that P-TEFb preferentially phosphorylated a CTD that was already partly phosphorylated, but that otherwise the extensive phosphorylation observed did not occur in a processive manner (Marshall et al., 1996).

The results of a comparison of transcription reactions driven by polymerase with or without the CTD suggested that the CTD was the physiological target of P-TEFb. DRB sensitive transcripts only arose if the CTD was intact (Marshall et al., 1996). Thus, P-TEFb is a key elongation control factor that can phosphorylate the CTD of the large subunit of RNA polymerase II in a DRB-sensitive manner (Marshall et al., 1996; Zhu et al., 1997; Peng et al., 1998a; 1998b; 1998c). The involvement of the CTD in elongation control is clear (Marshall et al., 1996; Chun and Jeang, 1996) and the ability of P-TEFb to phosphorylate this domain as a functional target has been well characterized, including in an in vitro reconstitution system (Marshall et al., 1996; Peng et al., 1998a).

B. P-TEFb Kinase Activity

Cloning of the subunits of P-TEFb began with sequence analysis of the small subunit of purified Drosophila P-TEFb. Full length Drosophila cDNA encoding the small subunit was first obtained (Zhu et al., 1997). The sequence databases indicated that a potential human homologue had already been identified (Zhu et al., 1997). The human protein, called PITALRE, had sequence similarity to other cyclin dependent kinases (Grana et al., 1994). However, aside from its ability to associate with other unknown proteins, its nuclear localization and its ability to carry out serine phosphorylation, its function was unknown (Garriga et al., 1996a; Garriga et al., 1996b). Proof that PITALRE was a component of human P-TEFb came from depletion experiments in which PITALRE antibodies were found to remove all P-TEFb activity from HeLa nuclear extract (Zhu et al., 1997).

Full length cDNA encoding the large subunit of Drosophila P-TEFb was also obtained using the protein sequence information (Peng et al., 1998b). The sequence of the cDNA indicated that the amino terminus of the large subunit had similarity to other cyclins (Peng et al., 1998b). This provided the second piece of evidence that P-TEFb was a kinase/cyclin pair, but proof that the P-TEFb was a cyclin dependent kinase came from comparing the activity of one or both of the Drosophila subunits. The kinase subunit alone had no activity (Peng et al., 1998b). Simultaneous expression of both Drosophila subunits using a baculovirus expression system resulted in a heterodimeric protein that had full CTD kinase activity and functionally substituted for native P-TEFb during in vitro transcription assays (Peng et al., 1998b). Because of this requirement for the cyclin subunit, the kinase subunit was named cyclin dependent kinase 9 (Cdk9) (Peng et al., 1998b). The cyclin subunit was named cyclin T because of its involvement in transcription (Peng et al., 1998b).

There are now known to be multiple forms of P-TEFb, but all contain the kinase subunit Cdk9 (Zhu et al., 1997) and one cyclin subunit encoded by either a cyclin T (Peng et al., 1998b; 1998c) or cyclin K gene (Fu et al., 1999). Humans have one Cdk9 gene, two cyclin T genes, T1 and T2, and one cyclin K gene (Peng et al., 1998c; Edwards et al., 1998).

Using the Drosophila cyclin T protein sequence and the human EST database, cDNAs encoding portions of three different human cyclin T subunits were found (Peng et al., 1998c). The novel cyclins were encoded by two genes: T1 and T2. The T2 gene produced two predominate splice variants differing from each other only at their extreme carboxyl termini. Cyclin T1 and T2 were over 80% identical in the amino terminal cyclin box region, but less than 50% identical in the rest of the protein (Peng et al., 1998c). All three proteins, cyclin T 1, T2a and T2b produced active recombinant P-TEFb molecules when co-expressed with human Cdk9 (Peng et al., 1998c).

The cyclin box was essential for activity (Peng et al., 1998c). The rest of the cyclin protein was not essential in vitro, but was required for maximal activity (Peng et al., 1998c). Although the region downstream of the cyclin box does not have a clear function yet, it may be used to interact with other proteins including its substrate (Marshall et al., 1996). In HeLa cells, there was no evidence of free P-TEFb subunits. About 80% of Cdk9 was complexed with cyclin T1 and 10% to 20% was complexed with cyclin T2a and T2b (Peng et al., 1998c). Cdk9 and both cyclin T's were expressed in all of a wide variety of tissues tested (Peng et al., 1998c). Cyclin T1 was independently cloned as a Tat associated protein (Wei et al., 1998) (see below).

Human cyclin K was identified in a yeast screen based on its ability to restore cell-cycle progression and rescue the lethality of deletion of yeast G1 cyclins (Edwards et al., 1998). The original study also showed that cyclin K immunoprecipitates from mammalian cells possessed CTD kinase activity, but the kinase partner was not identified. Recently, cyclin K was isolated in a two-hybrid screen using human Cdk9 as bait (Fu et al., 1999). A Cdk9/cyclin K heterodimer was purified from insect cells infected with a baculovirus expressing both proteins. This protein had potent CTD kinase activity and was able to substitute for immunodepleted human P-TEFb during in vitro transcription reactions (Fu et al., 1999). A comparison of the sequences in the cyclin box region of cyclin K, T1 and T2 indicates that the three proteins share about 32% identity, with cyclin K being slightly more similar to cyclin T1 than T2.

Subunits of the P-TEFb Cdk9, cyclin T and cyclin K homologues have been identified in many species. A yeast homologue has not been definitively identified, but the properties of CTK1 suggest that it might play a homologous role in yeast (Lee and Greenleaf, 1997).

C. Involvement In HIV Tat Transactivation

P-TEFb has been identified as the cellular cofactor for the HIV transcriptional activator, Tat (Mancebo et al., 1997; Zhu et al., 1997). Tat is a small protein encoded by HIV and other lentivirus genomes that is required to activate the promoter contained within the viral long terminal repeat (LTR) (Karn, 1999; Rana and Jeang, 1999; Taube et al., 1999). This strong transactivator is targeted to the viral promoter through interaction with a region of the nascent RNA transcript called TAR. Tat associates with a 3 nucleotide bulge in the stem of a hairpin structure that forms spontaneously in TAR. The functional consequence of this association is the enhancement of processivity of RNA polymerase II molecules initiating from the LTR, such that long primary transcripts are produced (Kao et al., 1987; Laspia et al., 1993; Marciniak and Sharp, 1991; Toohey and Jones, 1989). These transcripts in turn are differentially spliced to form all viral gene products. In the absence of Tat, short abortive transcripts that encode no proteins are predominately produced (Kao et al., 1987).

The enhancement of processivity brought about by Tat requires at least one cellular cofactor. Before identification of the cofactor, its existence and general properties were predicted by several laboratories (Carroll et al., 1992; Madore and Cullen, 1993). Early experiments indicated that the activation domain of Tat interacted with the cellular factor (Carroll et al., 1992) and that the cellular factor extended the sequence requirement in TAR to include the bulge and loop (Madore and Cullen 1993). Progress was made when Tat was found to associate with a cellular kinase initially of unknown identity (Herrmann and Rice, 1993). This Tat associated kinase (TAK) was found to be able to phosphorylate the carboxyl terminal domain of the large subunit of RNA polymerase II and was sensitive to the transcriptional inhibitor DRB (Herrmann and Rice, 1995).

A comparison of the properties of Tat in activating the HIV LTR and the general properties of P-TEFb suggested that P-TEFb might be TAK. Several groups had shown that Tat increased the fraction of RNA polymerase II molecules that made long transcripts after initiation from the HIV LTR (Laspia et al., 1993, Marciniak and Sharp, 1991; Toohey and Jones, 1989). There were strong parallels between the in vitro Tat results and the general features of elongation control found in vitro using a Drosophila system (Kephart et al., 1992; Marshall and Price, 1992; Marshall and Price, 1995). P-TEFb became a strong prospect for the Tat cofactor when it was discovered that it was a DRB-sensitive CTD kinase (Marshall et al., 1996).

Proof that P-TEFb was TAK came after the kinase subunit of Drosophila P-TEFb was cloned and the human homologue was found to be Cdk9 (Zhu et al., 1997). Cdk9 associated with wildtype Tat, but not activation domain mutants of Tat (Yang et al., 1997; Zhu et al., 1997) and depletion of P-TEFb from HeLa nuclear extract rendered the extract unable to carry out Tat transactivation (Zhu et al., 1997). The involvement of P-TEFb in Tat transactivation was further supported by the results from a screen for drugs that inhibited the process. All compounds that were found to block Tat transactivation also inhibited the+kinase activity of P-TEFb (Mancebo et al., 1997).

Recent studies have shed light on the details of the interaction of Tat, TAR and P-TEFb (Rana and Jeang, 1999). Tat forms a triple complex with P-TEFb, containing Cdk9 and cyclin T1, and TAR (Zhu et al., 1997; Garber et al., 1998b; 1998a; Wei et al., 1998; Wimmer et al., 1999; Rana and Jeang, 1999; Price, 2000).

Rodent cells can be made permissive for Tat transactivation by the expression of human cyclin T1 (Bieniasz et al., 1998; Wimmer et al., 1999) or by making a single amino acid change in mouse cyclin T1 (Bieniasz et al., 1998; Garber et al., 1998). Human cyclin T2a or T2b do not support Tat transactivation (Napolitano et al., 1999; Wimmer et al., 1999) and it is likely that cyclin K will not either because it lacks the cysteine residue at position of 261 of cyclin T1 that is required for a zinc-dependent interaction between cyclin T1 and HIV-1 Tat (Garber et al., 1998).

The requirement for specific sequences in the loop of TAR is conferred by cyclin T1 (Wei et al., 1998), however, it is not clear if the loop is contacted by cyclin T1 or by an altered conformation of Tat. Results from studies of the interactions between Tat and TAR from HIV-1, HIV-2, $SIV_{mnd}$, and EIAV and human, murine, equine and canine cyclin T1 have indicated several important features of the Tat/TAR/P-TEFb interaction. All Tat proteins associate with P-TEFb, however they are somewhat relaxed in their selectivity with HIV-2 and $SIV_{mnd}$ binding both cyclin T1 and T2 (Bieniasz et al., 1999a). Recruitment of the Tat/P-TEFb complex is more specific, with only P-TEFb containing cyclin T1 allowing complexation with TAR (Bieniasz et al., 1998; Taube et al., 1999). Species specificity is conferred by the interaction between the Tat/cyclin T1 complex and TAR (Bieniasz et al., 1998; Bieniasz et al., 1999b; Taube et al., 1999). Recent evidence suggests that in addition to the region around amino acid 261 in human cyclin T1, another region on the amino terminal side of the cyclin box (amino acid 29) is important for recognition of TAR (Taube et al., 1999).

P-TEFb is thus required for Tat transactivation (Zhu et al., 1997; Mancebo et al., 1997; Bieniasz et al., 1998; Wimmer et al., 1999) and for productive HIV infection (Wimmer et al., 1999; Flores et al., 1999). The targeting of cyclin T1 by Tat seems well suited to the viral goal of propagating during the activation of T cells and the differentiation of monocytes to macrophages. There is an increase in P-TEFb activity (TAK activity) during activation of peripheral blood lymphocytes (Gold et al., 1998; Garriga et al., 1998; Herrmann et al., 1998), peripheral blood mononuclear cells and after the differentiation of promonocytic cell lines to macrophages (Yang et al., 1997). The increase in TAK activity in peripheral blood lymphocytes has been shown to be due to an increase in mRNA and protein levels of both Cdk9 and cyclin T1 (Herrmann et al., 1998).

Another study showed that the levels of cyclin T1 were upregulated by two independent signaling pathways triggered by PMA or PHA (Garriga et al., 1998). The latter study showed that the ability of the peripheral blood lymphocytes to support HIV replication and productive infection directly correlated with the levels of induced cyclin T1 and CTD kinase activity (Garriga et al., 1998). A further study showed that P-TEFb was essential and limiting for HIV-1 replication in cultured cells (Flores et al., 1999). In this study, HIV replication was seen to be exquisitely sensitive to the levels of P-TEFb with a 6 to 20 fold reduction in Tat transactivation seen with only a 50% reduction in P-TEFb activity (Flores et al., 1999).

All results obtained so far suggest that Tat-transactivation and HIV replication are closely tied to the levels of P-TEFb (Cdk9/cyclin T1). This allows the virus to infect many cells but maintain its latency until the host cell is activated. HIV also takes advantage of CIITA, a transcriptional activator of the major histocompatibility class II genes that are responsible for antigen processing and presentation in B cells, activated T cells and antigen presenting cells. CIITA functions through recruitment of P-TEFb, but because of competition between Tat and CIITA for the same region of cyclin T1, CIITA activation is blocked during HIV infection. Because of this, the HIV infected cells more effectively escape the immune response (Kanazawa et al., 1999).

D. Mechanism of P-TEFb Action

The involvement of P-TEFb in elongation control in general and Tat transactivation specifically is now clear.

The kinase activity of P-TEFb is required in all assays requiring P-TEFb function, but there is more than one possible target for phosphorylation. The evidence suggests very strongly that the CTD of the large subunit of RNA polymerase II is the important physiological target. The CTD is phosphorylated during the transcription cycle at the time P-TEFb is known to act (Dahmus, 1996; Egyhazi et al., 1996) and the CTD is required for elongation control (Chun and Jeang, 1996; Marshall et al., 1996). Transcriptional activity, the CTD kinase activity of P-TEFb, and phosphorylation of RNA polymerase II in early elongation complexes are all inhibited by DRB (Marshall et al., 1996). Finally, prephosphorylation of the polymerase in early elongation complexes by P-TEFb (Peng et al., 1998a) or in preinitiation complexes (Wada et al., 1998) allows the polymerase to at least partially overcome the action of negative factors that would otherwise block processive elongation. Although the CTD is the most likely target, TFIIF and the SPT5 subunit of DSIF are phosphorylated by P-TEFb. However, no functional significance of the phosphorylation of these factors has been discovered.

Since other CTD kinases are always present in vivo and usually present in vitro their role in elongation control needs to be resolved. A number of kinases can phosphorylate the CTD (Dahmus, 1996), but only P-TEFb has been shown to modify the functional properties of RNA polymerase II (Marshall et al., 1996). P-TEFb has been shown to phosphorylate the CTD of RNA polymerase II in an early elongation complex at the time it is known to functionally modify the elongation properties of the polymerase (Marshall et al., 1996). TFIIH containing Cdk7/cyclin H/Mat1 (CAK) phosphorylated the CTD of pure RNA polymerase II at the same rate that P-TEFb did; but of the two kinases, only P-TEFb had the ability to confer processive elongation properties on an early elongation complex (Marshall et al., 1996).

The role of the CTD kinase activity of TFIIH in Tat transactivation is not clear. TFIIH has been found to associate with Tat (Blau et al., 1996; Cujec et al., 1997; Garcia-Martinez et al., 1997; Parada and Roeder, 1996) and based on differential sensitivity of TFIIH and P-TEFb to a pseudosubstrate peptide it was concluded that in addition to P-TEFb, the kinase activity of TFIIH was required for Tat to work (Cujec et al., 1997). However, two recent reports came to the opposite conclusion. One showed that Tat transactivation was unaffected after immunodepletion of CAK under conditions that do not deplete TFIIH (Chen and Zhou, 1999) and the other showed that TFIIH was lost from the elongation complex leaving only P-TEFb (Ping and Rana, 1999). Since TFIIH is present in preinitiation complexes and is then lost from early elongation complexes (Ping and Rana, 1999; Zawel et al., 1995) and P-TEFb functions during elongation it is possible that the two kinases work sequentially. This possibility was suggested earlier when it was found that P-TEFb preferred to phosphorylate a CTD that had already been partially phosphorylated (Marshall et al., 1996; see also, Yankulov and Bentley, 1998).

P-TEFb has no effect on elongation by RNA polymerase II in the absence of other factors (Peng et al., 1998a). Instead, it overcomes the effects of factors that negatively affect elongation (Garber and Jones, 1999). Factor 2 was the first potential component of N-TEF identified. It is a member of the SWI/SNF family of proteins (Liu et al., 1998) and has an ATP dependent RNA polymerase II termination activity (Xie and Price, 1996; Xie and Price, 1997). Because P-TEFb is unable to reverse the termination activity of factor 2, other N-TEFs were postulated (Peng et al., 1998a). Controlling the termination activity of factor 2 may be important for ensuring the long term survivability of elongation complexes and there is evidence for antitermination activities (Mingyi Liu and David Price). In fact, TFIIF has been shown to partially inhibit factor 2 (Peng et al., 1998a).

Two other factors have been identified as playing a role in DRB sensitive transcription. The two factors, DSIF (Wada et al., 1998; Yamaguchi et al., 1999b) and NELF (Yamaguchi et al., 1999a), are able to impede elongation by RNA polymerase II on a dC tailed template. The kinase activity of P-TEFb is required to overcome their negative effect (Wada et al., 1998) (Dan Renner and David Price). The large subunit of DSIF has also been shown to play a role in Tat transactivation (Wu-Baer et al., 1998). Finally, a CTD phosphatase, FCP1 (Archambault et al., 1998), may be involved in regulating the phosphorylation state of the polymerase in early elongation complexes and its activity may be regulated by HIV Tat (Cho et al., 1999; Marshall et al., 1998). It is likely that other factors will be found that modulate the elongation potential of RNA polymerase II.

P-TEFb function requires its kinase activity, but how this activity is normally directed toward the elongation complex is less well understood. Early in vitro experiments indicated that P-TEFb was not functionally associated with preinitiation complexes (Marshall and Price, 1992) and no experiments have indicated that it is functionally associated with early elongation complexes from any gene except the HIV-LTR. P-TEFb has been detected in association with preinitiation complexes and early TAR-containing elongation complexes using antibody detection methods (Ping and Rana, 1999). P-TEFb has also been shown to interact with double stranded RNA (Zhou et al., 1998), but it is not clear that the interaction is strong enough to recruit P-TEFb to an elongation complex.

P-TEFb is recruited to the early elongation complex during transcription of the HIV LTR (Rana and Jeang, 1999). Tat has been shown to associate with early elongation complexes formed on the HIV LTR (Keen et al., 1997) and recruit P-TEFb (Isel and Karn, 1999; Ping and Rana, 1999; Zhou et al., 1998). Furthermore, this recruitment causes hyperphosphorylation of the CTD (Isel and Karn, 1999; Zhou et al., 1998). The first example of natural recruitment of P-TEFb to an activator has just been reported. CIITA functionally recruits P-TEFb containing cyclin T1 to MHC class II promoters (Taube et al., 1999). Finally, P-TEFb is dramatically recruited to the transcribed region of HSP70 genes during heat shock in a manner consistent with it playing a role in activation.

Artificial targeting experiments have demonstrated that recruitment of P-TEFb to either RNA or DNA elements can activate transcription. Expression of a reporter construct containing an HIV Rev response element was increased when it was cotransfected with a Rev/Cdk9 chimera (Fujinaga et al., 1998; Gold et al., 1998) or a Rev/cyclin T1 chimera (Bieniasz et al., 1999c). This artificial recruitment of P-TEFb through an RNA element required the kinase activity of Cdk9 (Fujinaga et al., 1998). Activation must be through a different mechanism than that found in similar experiments with artificially recruited Cdk8 for which kinase activity was not required (Gold and Rice, 1998). Targeted recruitment of either Cdk9 or cyclin T1 to DNA targets also activates transcription and, when a Cdk9 mutant lacking kinase activity was used, no activation was seen (Majello et al., 1999).

As is found with the intact HIV LTR, the activation by targeted P-TEFb is mediated through an increase in productive elongation (Majello et al., 1998). A difference between RNA and DNA targeting of activators has been seen (Pendergrast and Hernandez, 1997). In this study, RNA targeted Tat was a stronger activator than DNA targeted Tat. This could have been due to the increased affinity of Tat for P-TEFb when it is bound to TAR, but RNA tethered activators may effect elongation more than DNA tethered activators (Pendergrast and Hernandez, 1997).

One explanation for the existence of elongation control is that cells require a mechanism to globally or specifically regulate gene expression. Since the accumulation of most mRNAs is sensitive to inhibitors of P-TEFb, it seems that elongation control could be used to adjust most or all mRNA levels in particular cells when the need arises. In addition, some genes might have evolved to use the process in gene specific control mechanisms. The AIDS virus uses the process to control the expression of viral proteins and may use the programmed change in cyclin T1 level as a sensor for the appropriate timing of productive infection (Garriga et al., 1998; Gold et al., 1998). The expression of many cellular genes, exemplified by Fos (Collart et al., 1991), is also controlled by this process, though the detailed mechanism is not clear.

Another potential reason for elongation control is to couple transcription with RNA processing. The evidence is mounting that phosphorylation of the CTD allows the recruitment of processing factors including those involved in capping, polyadenylation and possibly splicing (Bentley, 1999; Minvielle-Sebastia and Keller, 1999). For example, the large subunit of DSIF stimulates mRNA capping (Wen and Shatkin, 1999) and phosphorylation of specific residues in the CTD have a differential effect on recruitment and activation of the capping enzyme (Ho and Shuman, 1999). A likely model is that the concerted action of first negative and then positive factors causes a kinetic delay shortly after initiation that allows the replacement of initiation factors with elongation and processing factors. This model is not incompatible with any number of genes using the process as a control mechanism to regulate mRNA levels.

The involvement of P-TEFb in the regulation of transcription from the HIV-1 promoter is thus well documented, but it is not clear why replication of the virus is more sensitive to reduction of P-TEFb activity than other viral or cellular promoters. One study used both an in vitro and in vivo assay to screen a library of over 100,000 compounds for molecules that blocked Tat transactivation of the HIV-1 promoter, but not expression from the CMV promoter. Every compound identified was found to inhibit P-TEFb (Mancebo et al., 1997).

Three of these inhibitors were chosen for further study and were shown to block HIV-1, but not HTLV-1 replication at concentrations that were on average about 14 times lower than concentrations that caused cytotoxic effects (Flores et al., 1999). Significantly, expression of a dominant-negative Cdk9 transgene at levels equal to the wildtype Cdk9 dramatically reduced the ability of the cells to support HIV-1 replication without having any effect on the growth of the cells (Flores et al., 1999).

HIV-1 replication in T cells requires activation of the cells and activation is coupled to upregulation of cyclin T1 levels (Garriga et al., 1998; Herrmann et al., 1998). Initiation from the HIV-1 promoter in T cells before activation is not accompanied by efficient elongation to make viral mRNAs. After T cell activation, when the levels of P-TEFb containing cyclin T1 have increased, viral mRNAs are produced. This tight control of expression in vivo suggests that the HIV-1 promoter is strongly controlled by the action of negative factors that increase the dependence on P-TEFb.

Two factors NELF and DSIF play a general role in elongation control (Wada et al., 1998; Yamaguchi et al., 1999; Garber and Jones, 1999) and DSIF has been shown to play a role in Tat transactivation (Wu-Baer et al., 1998). It is also possible that a CTD phosphatase might be especially active at the HIV-1 promoter. Presumably, the phosphatase would have a negative effect on elongation by reversing the P-TEFb dependent phosphorylation of the CTD. Support for this idea comes from the finding that the phosphatase is inhibited by Tat (Marshall et al., 1998; Cho et al., 1999). Studies aimed at elucidating the mechanism of enhanced sensitivity of transcription from the HIV-1 promoter compared to other viral and cellular promoters should emphasize in vivo assays with virus or stably integrated viral promoters (Flores et al., 1999), because less than a 5 fold difference is seen between the HIV-1 and CMV promoter in vitro and in transient transfection assays.

II. Flavopiridol

Flavopiridol (L86-8275; NSC-649890; HMR 1275; CAS Registry Number, 131740-09-5; Molecular Weight, 438.29; Molecular Formula, $C_{21}H_{20}ClNO_5HCl$), is a potential anticancer therapeutic currently being tested in phase I and II clinical trials (Senderowicz and Sausville, 2000). This compound, which is prepared by total synthesis, is structurally related to a compound derived from a natural product originally obtained from Dysoxylum binectariferum, a plant indigenous to India (Sedlacek et al., 1996).

Flavopiridol was initially believed to be a tyrosine kinase antagonist with in vitro activity against the epidermal growth factor (EGF) receptor. However, early studies revealed that flavopiridol was not cytotoxic to stationary MDA-MB-468 breast carcinoma cells, but reversibly inhibited the growth of cells in exponential growth phase. At concentrations of 25-150 nM, flavopiridol inhibited the growth of human breast, prostate and lung carcinoma cells, with the MDA-MB-468 breast carcinoma cells being 60- and 400-fold more sensitive to flavopiridol than to quercetin and genistein, respectively (Kaur et al., 1992).

Initial mechanistic studies (Kaur et al., 1992) revealed that flavopiridol inhibited asynchronously growing MDA-MB-468 breast carcinoma cells with accumulation of a fraction of the treated cells with G2/M DNA content and a decline in S-phase fraction. It was subsequently demonstrated that when MDA-MB-468 breast carcinoma cells were released from aphidicolin-block at the beginning of S-phase into medium with 200 nM flavopiridol, they ultimately completed S-phase but arrested with G2/M DNA content without rounding up, suggesting that the block to cell cycle progression was in G2 or very early M-phase. Likewise, when cells synchronized in M-phase with nocodazole were released into medium containing 200 nM flavopiridol, they completed M-phase, but did not progress into S-phase.

The foregoing results collectively suggested that flavopiridol could block cell cycle progression acting prior to entry into S-phase or prior to entry into M-phase. Subsequent studies revealed flavopiridol to be a cyclin-dependent kinase (Cdk) inhibitor, a number of which inhibitors have recently identified by intensive screening (Gray et al., 1999). Flavopiridol has now been reported to induce apoptosis in various types of cancerous cells (Schwartz et al., 1997; Parker et al., 1998; Arguello et al., 1998; Patel et al., 1998; Schrump et al., 1998; Byrd et al., 1998; Shapiro et al., 1999; Li et al., 2000; Senderowicz and Sausville, 2000) and has been proposed to target the Cdks that control the cell cycle (Losiewicz et al., 1994; Carlson et al., 1996).

Control of cell cycle progression is maintained by complex coordinated kinase and phosphatase reactions. Cdk4 and 6 coupled with their respective cyclin partners, the D-type cyclins, are necessary for transition through the earlier phase of G1, and the activity of Cdk2 (p33 cdk2) and its cyclin E partner are required at the G1/S transition. In a similar fashion, CDC2 (also known as Cdk1, $p34^{cdc2}$) is complexed with cyclin-A and with cyclin-B at the G2/M transition. These Cdk complexes are in turn regulated by specific post-translational mechanisms and in the case of G1 kinases, by the stoichiometric combination with the growing family of inhibitory proteins, such as p15, p16, p21 and p27 (Pines, 1994; Grana and Reddy, 1995; Morgan, 1995; Morgan, 1997).

Early studies reported flavopiridol to prevent the G2 related increase in histone H1 kinase activity mediated by Cdk1. Flavopiridol was shown to inhibit [$^{32}P$]-orthophosphate labeling of Cdk1 threonine and tyrosine residues and to decrease phosphotyrosine content of $p_{34}^{cdc2}$. Diminution of Cdk1 phosphotyrosine appeared selective, since general depletion of cellular phosphotyrosine was not observed (Worland et al., 1993).

Subsequent experiments reported that flavopiridol inhibited other cyclin-dependent kinases (Carlson et al., 1996). In 1996, one report summarized flavopiridol as inhibiting cdk1, cdk2, cdk4 and cdk7 (Sedlacek et al., 1996), although flavopiridol has been shown to be less potent on Cdk7 (Senderowicz and Sausville, 2000). Individual studies include those of Carlson et al. (1996), reporting that flavopiridol induces G1 cell cycle arrest in the MCF-7 human breast cancer cells by inhibiting cdk2 and cdk4; and the later report of Singh et al. (1999), that cyclin D1/cdk6 is the primary target for the flavopiridol-mediated G1 block in the MCF-10A breast epithelial cell line.

A further study focused increasing attention on cdk2, by determining the crystal structure of Cdk2 in complex with flavopiridol. The x-ray structure of Cdk2 complexed to deschloroflavopiridol (L86-8276) was determined and compared to the x-ray structure of Cdk2 complexed to ATP (De Azevedo et al., 1996). It was reported that deschloro-flavopiridol binds in the ATP-binding pocket with the benzopyran ring occupying approximately the same region as the purine ring of ATP, which was said to confirm the experiments using purified Cdk1 assays (Worland, 1993). Thus, the structural studies (De Azevedo et al., 1996) help to explain why inhibition of Cdk2 is competitive with ATP.

It will be seen from the foregoing studies, that there have been no suggestions of cdk9 as a target for flavopiridol action.

In terms of the cyclin components of cyclin-dependent kinases, studies within the last two years have reported that flavopiridol is able to downregulate cyclin $D_1$ protein expression in mammalian cells in vitro and in vivo (Patel et al., 1998, Carlson, 1996, Carlson, 1999). Senderowicz et al. (1997) first reported that MCF-7 breast cancer cells exposed to flavopiridol showed a specific decline in steady state cyclin $D_1$ protein levels due to diminished cyclin $D_1$ mRNA species. The treatment of breast cancer cells with flavopiridol was then reported to decrease transcription of the gene encoding cyclin D1 (Carlson et al., 1999); and Singh et al. (1999) also reported cyclin $D_1$ to be a target for flavopiridol. The connection between flavopiridol, cdk6 and cyclin $D_1$ was also mentioned in an abstract by Yao and Browning (1988), commenting on the potential use of flavopiridol to treat herpes infections. High levels of flavopiridol were also said to affect the levels of 63 different mRNAs in *Saccharomyces cerevisiae* (Gray et al., 1998).

Again, prior to the present invention, there was no reported connection between flavopiridol and cyclin T1.

III. Inhibition of P-TEFb by Flavopiridol

Despite the apparent lack of connection between flavopiridol, cdk9 and cyclin T1, the present inventors discovered that flavopiridol potently inhibits the cdk9 subunit of P-TEFb. Consequently, flavopiridol inhibits transcription by human RNA polymerase II by blocking the transition into productive elongation controlled by P-TEFb (Chao et al., 2000).

The biochemical nature of flavopiridol's inhibition of P-TEFb is also surprising, even when compared with the actions of flavopiridol on other cyclin-dependent kinases. Flavopiridol inhibits the kinase activity of P-TEFb with a Ki of about 3 nM and, unlike all other cyclin dependent kinase inhibitors, is not competitive with ATP. This is also in marked contrast with the action of flavopiridol on the cyclin-dependent kinases, cdk1, cdk2, cdk4, cdk6 and cdk7, in which inhibition is competitive with ATP in all instances with higher Ki's (~40-60 nM).

The effectiveness of flavopiridol-mediated inhibition is further surprising in quantitative, as well as qualitative terms. In fact, flavopiridol is about 3 orders of magnitude more potent than the commonly used P-TEFb inhibitor, DRB. As discussed above, P-TEFb comprised of Cdk9 and cyclin T1 is a required cellular cofactor for the HIV-1 transactivator, Tat. The inventors therefore further discovered that, consistent with its new-found ability to inhibit P-TEFb, flavopiridol blocked Tat transactivation of the viral promoter in vitro. Furthermore, flavopiridol blocked HIV-1 replication in both single round and viral spread assays with an $IC_{50}$ of less than 10 nM (see also, Chao et al., 2000).

Since P-TEFb is a key factor in HIV-1 infection, the present discovery of an uncompetitive inhibitor of this key enzyme represented a potential breakthrough in HIV research and treatment. The demonstration that flavopiridol clearly blocks HIV-1 propagation in a widely accepted model system, confirms that the present invention truly represents a dramatic breakthrough. Although not suggesting the advantageous uses made possible by this invention, the previous administration of flavopiridol to cancer patients means that flavopiridol can be readily administered to HIV patients.

In cancer patients, flavopiridol must currently be administered parenterally, and, its MTD administered as a 72 hour-continuous infusion every 2 weeks are 50 mg/m²/day and 78/mg/m²/day, achieving concentrations in plasma of about 200 to 400 nM. At these doses, flavopiridol causes diarrhea and a pro-inflammatory syndrome (Senderowicz et al., 1998). Importantly, the present invention provides for the selection of effective doses significantly lower than the high levels used in cancer patients. The studies of this invention indicate that flavopiridol will be useful in AIDS patients at levels that achieve nanomolar drug levels orders of magnitude lower than those used to treat other indications, i.e. 10 to 20 nM rather than 200 nM to 400 nM, which will alleviate the previous problems.

The present use of flavopiridol to cancer patients, coupled with the ability to use significantly lower doses of flavopiridol for HIV therapy, should speed regulatory approval for the use of flavopiridol in the treatment of HIV and AIDS. Moreover, this invention is not limited to the use of flavopiridol to treat HIV-1 and AIDS. In fact, the use of P-TEFb inhibitors is broadly applicable to a range of other infections in which P-TEFb is a required cellular factor. These include for example, HIV-2, EIAV, SIV and BIV (Taube et al., 1999).

Flavopiridol is available from Hoechst Marion Roussel (Aventis Pharmaceuticals, Inc., Bridgewater, N.J., U.S.A.) and flavopiridol formulations are described in Example 8. In addition, a number of U.S. patents concern flavopiridol production and analogs, each of which are incorporated herein by reference. As described in U.S. Pat. No. 5,795,909, incorporated herein by reference, pharmaceutical agents may comprise the active compound, in this case, flavopiridol or a flavopiridol analog, which has been conjugated to a targeting agent for specific delivery to particular target cells. Although the flavopiridol compositions for use in the present invention will not need any such targeting in order to exert anti-HIV effects, the use of targeted flavopiridol and analogs is certainly encompassed herein.

U.S. Pat. No. 5,908,934 is incorporated herein by reference to provide processes for the preparation of chiral ketone intermediates useful in the preparation of flavopiridol and analogs. U.S. Pat. No. 5,849,733 is incorporated herein by reference to describe 2-thio and 2-oxo flavopiridol analogs, initially proposed for use in the treatment of proliferative diseases, which can now be used in the advantageous anti-HIV methods and formulations of this invention.

IV. Pharmaceutical Formulations

The fundamental pharmaceutical compositions of the present invention generally comprise an effective amount of at least a first flavopiridol or flavopiridol analog, dissolved or dispersed in a pharmaceutically acceptable carrier, aqueous medium or other acceptable formulation or vehicle. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other significant untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

Irrespective of which of the following exemplary or other pharmaceutical or pharmacological formulations are employed, the flavopiridol compounds and/or analogs will be administered in a manner compatible with the dosage formulation and in such amount as is therapeutically effective. Administration designed to give chronic exposure to plasma flavopiridol concentrations of about 10, 20, 30, 40, 50, 60, 70 or 80 nM or so, preferably about 30, 40, 50 or 60 nM or so, and more preferably, of about 25, 30, 35 or 40 nM or so, is contemplated to be particularly useful. Such levels may be readily obtained by oral, subcutaneous and intranasal routes of administration.

In terms of intravenous injection, flavopiridol compounds are provided to HIV patients in amounts between about 1 mg/m$^2$/day and about 78 mg/m$^2$/day, preferably for 72 hours every 2 weeks (particularly with other agents, such as ADP). More preferably, flavopiridol is given in amounts between about 4 mg/m$^2$/day and about 50 mg/m$^2$/day; even more preferably, in amounts between about 12 mg/m$^2$/day and about 28 mg/m$^2$/day; and still more preferably, in amounts between about 8 mg/m$^2$/day and about 16 mg/m$^2$/day. Accordingly, flavopiridol may be administered in amounts of about 0.5, 0.75, 1, 2, 3, 4, 5, 6, 7, 8, 9, 10, 11, 12, 13, 14, 15, 16, 17, 18, 19, 20, 22.5, 25, 27.5, 30, 35, 40, 45, 50, 55, 60, 65, 70, 75 and about 80 or so mg/m$^2$/day. Any such flavopiridol doses may be given over 0.5, 1, 1.5, 2, 2.5, 3, 3.5, 4, 4.5, 5, 6, 7, 10, 14 days or such like, preferably for 72 hours every 2 weeks.

Although intravenous injections and continuous infusions are currently preferred modes of administration, oral administration is not excluded from the invention. Therefore, other suitable doses are between about 5 mg/kg PO and about 25 mg/kg PO; more preferably, between about 10 mg/kg PO and about 20 mg/kg PO; and even more preferably, between about 8 mg/kg PO and about 15 mg/kg PO. Accordingly, flavopiridol doses of about 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 and about 36 or so mg/kg PO may be administered. Any form of solo or combined treatment may be continued for days, weeks, months or years, as determined by the physician.

A. Injectable Formulations

The flavopiridol compounds or analogs of the present invention will most often be formulated for parenteral administration, e.g., formulated for injection via the intravenous (including bolus and infusional), sub-cutaneous, intramuscular, transdermal, or other such routes, including peristaltic administration and direct instillation into a disease sites. The preparation of an aqueous composition that contains a flavopiridol or analog as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The flavopiridol compound or analog compositions can be formulated into a sterile aqueous composition in a neutral or salt form. Solutions of flavopiridol compounds or analogs as free base or pharmacologically acceptable salts can be prepared in water suitably mixed with a surfactant, such as hydroxypropylcellulose. Pharmaceutically acceptable salts, include the acid addition salts, and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the flavopiridol or analogs should be extensively dialyzed to remove undesired small molecular weight molecules, and/or lyophilized for more ready formulation into a desired vehicle, where appropriate. Sterile injectable solutions are prepared by incorporating the active flavopiridol agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active flavopiridol compounds or analogs, plus any additional desired ingredient from a previously sterile-filtered solution thereof.

Suitable pharmaceutical compositions in accordance with the invention will generally include an amount of the flavopiridol or analog admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver flavopiridol or analogs in accordance with the present invention.

B. Liposomes and Nanocapsules

In certain embodiments, liposomes and/or nanoparticles may also be employed with the flavopiridol or analogs. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

C. Oral Administration

In certain embodiments, active compounds may be administered orally. For oral administration, the active flavopiridol compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

D. Nasal Administration

One may use nasal solutions or sprays, aerosols or even inhalants for the treatment of HIV with flavopiridol. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known.

Inhalations and inhalants are pharmaceutical preparations designed for delivering a drug or compound into the respiratory tree of a patient. A vapor or mist is administered and reaches the affected area, often to give relief from symptoms of bronchial and nasal congestion. However, this route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, consists of finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient.

Particle size is of importance in the administration of this type of preparation. It has been reported that the optimum particle size for penetration into the pulmonary cavity is of the order of 0.5 to 7 $\mu$m. Fine mists are produced by pressurized aerosols and hence their use in considered advantageous.

E. Therapeutic Kits

This invention also provides therapeutic kits comprising flavopiridol or analogs for use in the present treatment methods. Such kits will generally contain, in suitable container means, a pharmaceutically acceptable formulation of at least one flavopiridol or analog, preferably a low-dose flavopiridol or analog. Written, electronic or other instructions for using the flavopiridol and/or flavopiridol analogs in the treatment or prevention of HIV inventions and AIDS will preferably be included.

The kits may also contain other pharmaceutically acceptable formulations, either for diagnosis/imaging or combined therapy. For example, such kits may contain any one or more of a range of anti-HIV drugs; non-specific anti-viral agents; anti-HIV antibodies and such like, as well as one or more diagnostics.

The kits may have a single container (container means) that contains the flavopiridol or analog, with or without any additional components, or they may have distinct containers for each desired agent. Where combined therapeutics are provided, a single solution may be pre-mixed, either in a molar equivalent combination, or with one component in excess of the other. Alternatively, each of the flavopiridol or analog and other anti-HIV agent components of the kit may be maintained separately within distinct containers prior to administration to a patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the flavopiridol or analog, and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the flavopiridol or analog to an animal or patient, e.g., one or more needles or syringes, aerosols, inhalants or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

V. Anti-HIV and AIDS Therapeutics

The flavopiridol- or flavopiridol analog-based treatment methods of the present invention may be combined with any other method(s) generally employed in the treatment of HIV or in any other disease or disorder that the patient exhibits. So long as a particular therapeutic approach is not known to be significantly detrimental to the patient's condition in itself, and does not significantly counteract the flavopiridol treatment, its combination with the present invention is contemplated.

When one or more agents are used in combination with the flavopiridol therapy, there is no requirement for the combined results to be additive of the effects observed when each treatment is conducted separately. Although at least additive effects are generally desirable, any increased effect above one of the single therapies would be of benefit. Also, there is no particular requirement for the combined treatment to exhibit synergistic effects, although this is certainly possible and advantageous.

To practice combined therapy, one would simply administer to an animal a flavopiridol component in combination with another anti-HIV agent in a manner effective to result in their combined anti-HIV actions within the animal or patient. The agents would therefore be provided in amounts effective and for periods of time effective to result in their combined presence in the region of target cells. To achieve this goal, the agents may be administered simultaneously, either in a single composition, or as two distinct compositions using different administration routes. Alternatively, the two treatments may precede, or follow, each other by, e.g., intervals ranging from minutes to weeks or months.

Exemplary anti-HIV agents that are useful in connection with combined therapy are listed in Table A. Each of the agents listed therein are exemplary and by no means limiting. Some variation in dosage will necessarily occur depending on the condition of the subject being treated. The physician responsible for administration will be able to determine the appropriate dose for the individual subject.

TABLE A

ANTI-HIV DRUGS AND PROPERTIES

| DRUG (Synonyms) | Tradename | Commercial Source | Class of Compound | Biochemical Action | Dose/ Regimen | Clinical Considerations Combined/ Contraindicated |
|---|---|---|---|---|---|---|
| Amprenavir | Agenerase ™ | Glaxo Wellcome | Protease Inhibitor | Inhibits aspartic protease enzyme, thus inhibiting post-translational processing of gag and pol genes | Administered orally; 1200 mg taken twice daily (8 150 mg capsules); oral solutions also available, although 16% less bioavailable than capsules | Side effects include: nausea, vomiting, diarrhea, headache, stomach pains/gas, rash and numbing sensations on the skins; Hismanal, |

TABLE A-continued

ANTI-HIV DRUGS AND PROPERTIES

| DRUG (Synonyms) | Tradename | Commercial Source | Class of Compound | Biochemical Action | Dose/ Regimen | Clinical Considerations Combined/ Contraindicated |
|---|---|---|---|---|---|---|
| | | | | | | Propulsid, Halcion and Versed contraindicated; Multiple protease inhibitor and reverse transcriptase inhibitor combinations are useful; Rescriptor ™ increases Agenerase ™ levels. |
| Combination of Lamivudine (3TC) and Zidovudine (ZDV) | Combivir ® (Combination of Retrovir ® and Epivir ®) | Glaxo Wellcome | Nucleoside reverse transcriptase inhibitors | Synthetic nucleoside analogues (of cytidine and thymidine, respectively); active 5'-triphosphates inhibit reverse transcriptase via DNA chain termination after incorporation of the nucleoside analogue. | Administered orally; 1 tablet of Combivir ® is bioequivalent to 1 Epivir ® 150 mg tablet and 1 Retrovir ® 300 mg tablet | Not recommended for use in children under 12 years of age; or in patients with reduced renal function; 3 drug regimen: Combivir ® (combination of Retrovir ® and Epivir ®) plus a protease inhibitor or efavirenz. |
| Indinavir | Crixivan ™ | Merck | Protease Inhibitor | Inhibits both HIV-1 and HIV-2 proteases, thus inhibiting post-translational processing of gag and pol genes, rendering noninfectious virus. | Administered orally; 800 mg every 8 hours with at least 8 glasses of $H_2O$ a day; adhere to guidelines on food intake; DO NOT MISS DOSES | Side effects include: hemolytic anemia; exacerbates liver damage and cirrhosis; kidney stones; hair loss, skin and nail disorders; high blood sugar and diabetes; lipodystrophy; Saldane, Hismanal, Propulsid, Halcion and Versed contraindicated. |
| Efavirenz | Sustiva ™ | | HIV-1 specific, non-nucleoside, reverse transcriptase inhibitor (NNRTI) | Non-competitive inhibition of HIV-1 reverse transcriptase, thereby blocking RNA-dependent and DNA-dependent DNA polymerase activities | Administered orally; 600 mg taken once a day; capsules available in 50 mg, 100 mg or 200 mg; recommended to take at bedtime; with or without food; fatty meal not recommended | Side effects include: dizziness, sleeplessness, intense dreams, altered mood and anxiety; Hismanal, Propulsid, Halcion and Versed contraindicated. |
| Lamivudine (Also known as 3TC) | Epivir ™ | Glaxo Wellcome | Nucleoside analog reverse transcriptase inhibitor | Potent reverse-transcriptase inhibitor; inhibits both HIV-1 and HIV-2 reverse-transcriptase, thus inhibiting vial DNA synthesis; can also inhibit replication of hepatitis B virus | Administered orally; 150 mg twice a day; also available in syrup for children; taken with or without food; mean absolute bioavailability of 86% for the tablet and 87% for solution and 66% in children | Side effects include: nausea, vomiting, headaches, and rare cases of hair loss; peripheral neuropathy, pancreatitis (in children); Resistance develops within 12 weeks; |
| Saquinavir | Invirase ™ | | Protease Inhibitor | First protease inhibitor approved for HIV; inhibits HIV-1 and HIV-2 proteases, thus inhibiting post-translational processing of gag and pol genes, rendering noninfectious virus. | 600 mg, three times a day; poor absorption leads to HIV resistance | Side effects include: diarrhea, stomach discomfort and nausea; high blood sugar and diabetes; Seldane, Hismanal, Propulsid and antibiotics, such as Mycobutin, contraindicated. |
| Saquinavir | Fortovase ™ | | Protease Inhibitor | New version of saquinavir, same biochemical mechanism of action | Designed for improved absorption over Invirase ™; available in 200 mg pills; six pills (1,200 mg) three times a day with food for a daily dose of 18 pills (3,600 mg); if not taken with meal, should be taken within 2 hours afterwards | Side effects include: diarrhea, nausea, stomach discomfort, heartburn, liver toxicity, weakness and fatigue; high blood sugar and diabetes; Seldane, Hismanal, Propulsid, Halcion; Versed and the antibiotic Mycobutin contraindicated; double- and triple-combination regimens |

TABLE A-continued

ANTI-HIV DRUGS AND PROPERTIES

| DRUG (Synonyms) | Tradename | Commercial Source | Class of Compound | Biochemical Action | Dose/ Regimen | Clinical Considerations Combined/ Contraindicated |
|---|---|---|---|---|---|---|
| Zalcitabine (Also known as ddC) | Hivid ™ | Hoff-mann-LaRoche | Nucleoside analog reverse transcriptase inhibitor | Inhibits HIV reverse transcriptase; must be phosphorylated to be active; competes with the natural substrate for RNA-directed DNA polymerase, terminating chain synthesis. | Administered orally; Adults take 2.25 mg per day divided into three doses; average bioavailability 70–88% | with reverse transcriptase inhibitors are useful. Side effects include: the anemia or suppression of white blood cells, skin eruptions, canker sores, general inflammation of the mouth, nausea, pancreatitis, fever, peripheral neuropathy |
| Hydroxyurea | Hydrea ™ | Bristol Myers-Squibb | Cell cycle-phase specific antineo-plastic agent | Reduces number of adenine nucleotides and impairs DNA synthesis; blocks ribonucleotide reductase and impairs DNA synthesis; can also impair thymidine incorporation into DNA; active during the S-phase of cell cycle. | Administered orally; 500 mg twice a day | Side effects include: suppression of bone marrow; hair loss, anorexia, nausea, vomiting, diarrhea, constipation, rashes, birth defects in animals and should not be taken by pregnant women. |
| Ritonavir | Norvir ™ | Abbott | Protease Inhibitor | Inhibits both HIV-1 and HIV-2 proteases, thus inhibiting post-translational processing of gag and pol genes, rendering noninfectious virus. | Only available as a liquid; administered orally; 600 mg twice a day; should be taken with a full high-protein, high-fat meal | Side effects include: nausea, vomiting, weakness, diarrhea, numbing sensations around the mouth and elevated liver enzymes; high blood sugar and diabetes; Alprazolam, amiodarone, astemizole, bepridil, bupropion, cisapride, clorazepate, clozapine, diazepam, encainide, estazolam, flecainide, flurazepam, meperidine, midazolam, piroxicam, propafenone, propoxyphene, quinidine, rifabutin, terfenadine, triazolam and zolpidem contraindicated. |
| Adefovir Dipivoxil | Preveon ™ | Gilead Sciences | Nucleotide analog reverse transcriptase inhibitor | A nucleotide analog that targets HIV's reverse transcriptase enzyme; does not require as complex processing as nucleoside analog drugs | Available in 60 mg pill or 120 mg pill taken once a day; must take a daily L-carnitine supplement with Preveon ™ | Side effects include: nausea, diarrhea, liver and kidney problems |
| Delavirdine | Rescriptor ™ | | Non nucleoside analog reverse transcriptase inhibitor | Binds directly to and inhibits reverse transcriptase by disrupting catalytic site, thereby blocking RNA- and DNA-dependent DNA polymerase activities; does not compete with template or nucleoside triphosphates and does not require phosphorylation | 400 mg taken three times a day with or without food; people with achlorhydria (low stomach acid) should take Rescriptor with an acidic drink | Side effects include: rash (with potential for Stevens-Johnson Syndrome); Seldane, Hismanal, Propulsid, Mycobutin, phenytoin, phenobarbital, carbamazepine, certain amphetamines, calcium channel blockers, antiarrhythmics and anti-migraine drugs contraindicated; Tagamet ™ and related drugs not recommended as lowers Rescriptor ™ levels; combinations with other anti-HIV drugs useful. |
| Zidovudine (Also known | Retrovir ™ | Glaxo Wellcome | Nucleoside analog | Inhibits viral reverse transcriptase, interfering with | Administered orally; 300–600 mg per day; best if | Side effects include: loss of muscle, |

TABLE A-continued

ANTI-HIV DRUGS AND PROPERTIES

| DRUG (Synonyms) | Tradename | Commercial Source | Class of Compound | Biochemical Action | Dose/ Regimen | Clinical Considerations Combined/ Contraindicated |
|---|---|---|---|---|---|---|
| as AZT) | | | reverse transcriptase inhibitor | generation of DNA copies of viral RNA, thus inhibiting virion synthesis | taken on empty stomach; available in syrup form for children. | anemia, white blood cell depression, lip, mouth and tongue sores, bone marrow damage, headaches, skin rash, itching, weakness, nervousness, dizziness, nausea, stomach pain, confusion, loss of speech or appetite, muscle aches, fever or sweating, sore throat or abnormal bruising or bleeding; rare but serious side effect: lactic acidosis |
| Didanosine (Also known as ddI) | Videx ™ | | Nucleoside analog reverse transcriptase inhibitor (NRTI) | Inhibits activity of reverse transcriptase, which interferes with generation of DNA copies of viral RNA, which in turn inhibits synthesis of new virions | Administered orally; for adults - two 200 mg pills (400 mg) taken once daily; Children's ddI comes in cherry or mint flavor and must be mixed with an antacid (usually Maalox ™ or Mylanta ™). | Side effects include: stomach pain, diarrhea, peripheral neuropathy, pancreatitis, liver damage, seizures, headaches, abnormal bone marrow function, and allergic reactions; ddI should not be taken in combination with dapsone; ddI and Crixivan ™ should be taken at least one hour apart from one another; serious adverse reactions have been reported in people taking ddI at the same time as rifabutin and colfazimine |
| Nelfinavir | Viracept ™ | Agouron | Protease Inhibitor | Inhibits HIV protease, thus inhibiting post-translational processing of gag and pol genes, rendering noninfectious virus. | 750 mg taken three times a day with food or 1,250 mg taken every 12 hours; also available in a sprinkle formulation for children | Side effects include: diarrhea, allergic-type reactions; elevated liver function tests; high blood sugar and diabetes; Seldane, Hismanal, Propulsid, Halcion, Versed, Cordarone, Quinidex contraindicated; Rifampin ™ reduces levels of Viracept ™; Mycobutin ™ should be avoided; Nizoral ™ increases levels of Viracept ™ |
| Nevirapine | Viramune ® | | Non nucleoside analog reverse transcriptase inhibitor | Binds directly to reverse transcriptase causing disruption of catalytic site, thereby blocking RNA- and DNA-dependent DNA polymerase activities, thus inhibiting replication of the HIV virus. | Administered orally; 200 mg once a day for the first two weeks, and then 200 mg twice a day thereafter; also available as a liquid suspension for children. | Side effects include: rash, elevated liver function tests, fever and muscle soreness; affects the liver and causes other drugs to be processed too quickly, due to this effect, often lowers the levels of other drugs in the body; |

TABLE A-continued

ANTI-HIV DRUGS AND PROPERTIES

| DRUG (Synonyms) | Tradename | Commercial Source | Class of Compound | Biochemical Action | Dose/ Regimen | Clinical Considerations Combined/ Contraindicated |
|---|---|---|---|---|---|---|
| Stavudine (Also known as d4T) | Zerit ® | | Nucleoside analog reverse transcriptase inhibitor | Stavudine triphosphate competes with deoxythymidine triphosphate and incorporates into viral DNA, terminating DNA elongation (due to lack of 3'-OH) and inhibiting viral DNA growth | Administered orally; 40 mg twice a day for people weighing more than 60 kg and 30 mg for those that weigh less; taken with or without food; liquid version is available for children. | combination therapy with nevirapine and zidovudine useful. Side effects include: peripheral neuropathy; pancreatitis, elevated liver function tests and bone marrow suppression; combination of d4T and AZT is not recommended |
| Abacavir | Ziagen ™ | Glaxo Wellcome | Nucleoside analog reverse transcriptase inhibitor | Carbovir triphosphate inhibits HIV-1 reverse transcriptase by competing with dGTP and incorporating into viral DNA; absence of 3'-OH prevents DNA chain elongation, inhibiting viral DNA growth | Administered orally; one 300 mg pill taken twice a day; taken with or without food | Side effects include: hypersensitivity; increased fatigue, changes in liver function tests, headache, abdominal pain, constipation, diarrhea, nausea, vomiting, sleeplessness, skin rash, and dizziness; intended for use in combination with other antiretroviral agents |

The following examples are included to demonstrate preferred embodiments of the invention. It will be appreciated by those of skill in the art that the techniques disclosed in the examples that follow represent techniques discovered by the inventors to function well in the practice of the invention, and thus can be considered to constitute preferred modes for its practice. However, those of skill in the art will, in light of the present disclosure, appreciate that many changes can be made in the specific embodiments that are disclosed and still obtain a like or similar result without departing from the spirit and scope of the invention.

EXAMPLE 1

Flavopiridol Inhibits P-TEFb

To investigate the effects of flavopiridol on transcription, an in vitro assay involving a cytomegalovirus (CMV) promoter-containing template and HeLa nuclear extract was utilized. Reactions were carried out with the modified pulse-chase protocol (Peng et al., 1998a). Flavopiridol was added during pre-incubation step. The addition of increasing concentrations of flavopiridol during the reaction resulted in a dramatic inhibition of the appearance of the 660 nucleotide run-off transcript (FIG. 1). The radioactivity in run-off transcripts was quantitated and the $IC_{50}$ for the inhibitory effect was determined to be 33.6 nM.

To determine whether flavopiridol inhibited initiation or elongation, a pulse/chase assay designed to separate the two processes was performed. Flavopiridol (1 $\mu$M) was added at different steps of the pulse-chase study, including no drug added; drug added during pre-incubation; drug added during pulse; and drug added during chase. Reactions were stopped after pulse, or after chase. The same reactions were also performed using 50 $\mu$M DRB instead of flavopiridol.

On adding flavopiridol into the reactions during the formation of preinitiation complexes (preincubation), initiation (pulse), or elongation (chase), it was determined that initiation was not inhibited by the drug; as indicated by the uniform production of short transcripts during the pulse. However, the addition of flavopiridol at any step resulted in decreased levels of run-off transcripts during the subsequent chase.

Under the influence of flavopiridol, the elongating polymerases produced shorter incomplete transcripts, indicating that flavopiridol affected the elongation stage of transcription. Almost identical results were obtained when 5,6-dichloro-1-p-β-ribofuranosyl-benzimidazole (DRB) was used instead of flavopiridol. DRB is known to inhibit P-TEFb, the cyclin dependent kinase that controls the number of polymerases that enter into productive elongation (see Detailed Description herein; Price, 2000). This similarity suggests that flavopiridol could inhibit P-TEFb function.

An alternative possibility, that flavopiridol might directly inhibit the elongation reaction carried out by RNA polymerase II, was ruled out by the following study. To determine the effects of flavopiridol on elongation, increasing concentrations of flavopiridol were added into 5 minute elongation reactions. Early elongation complexes formed on an immobilized template were isolated by washing with 1 M KCl and 1% sarkosyl to remove all known elongation factors. Time points were taken at 0, 1, 2, 3, 4, and 5 minutes of elongation. Increasing concentrations of flavopiridol were added into 5 minute elongation reactions.

In this study, early elongation complexes were isolated under stringent washing conditions that eliminate all known factors able to affect the elongation properties of the polymerase (Peng et al., 1998a). The polymerases in these complexes are able to efficiently, albeit slowly, elongate their nascent transcripts as indicated by the 1, 2, 3, 4, and 5 minute chase time points. Since no differences in the lengths of the RNA attained during the 5 minute chase were seen, it can be concluded that flavopiridol does not inhibit the elongation properties of RNA polymerase II directly. Flavopiridol did not have any effect on transcription in vitro by RNA polymerase I or III. Taken together, the foregoing data indicate that flavopiridol affects the action of P-TEFb.

The direct effect of flavopiridol on the ability of P-TEFb to phosphorylate the carboxyl terminal domain (CTD) of RNA polymerase II was next examined. The kinase assay (Marshall et al., 1996) utilized recombinant P-TEFb, comprised of Cdk9 and cyclin T1 (Peng et al., 1998c), and purified RNA polymerase II. A 10 mM stock of flavopiridol in $Me_2SO$ was stored at $-80°$ C. The stock was diluted to 0.1 mM in $Me_2SO$ and a set of serial dilutions in 4% $Me_2SO$ was used to give the indicated concentration of flavopiridol. The final concentration of $Me_2SO$ in the transcription or kinase assays was less than 1%.

Figure 2A:
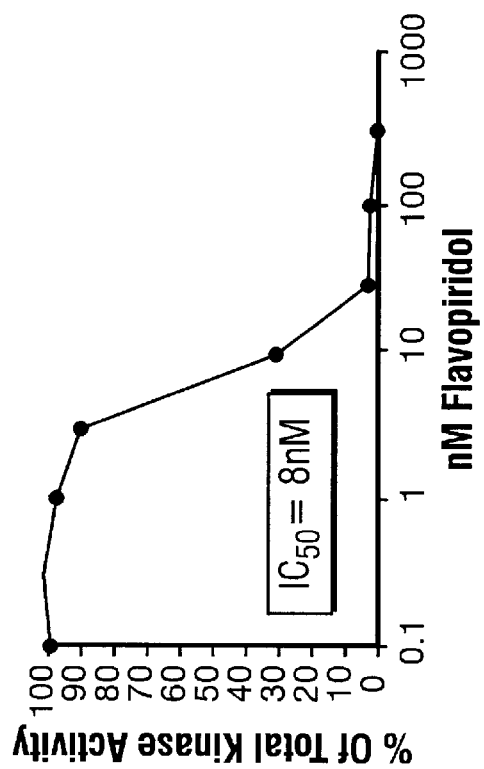
FIG. 2A, FIG. 2B, FIG. 2C and FIG. 2D. Inhibitory effects of flavopiridol on the kinase activity of P-TEFb in an ATP-independent manner. Kinase assays were performed and quantitated (Marshall et al., 1996) at the indicated ATP concentrations.
Figure 2B:
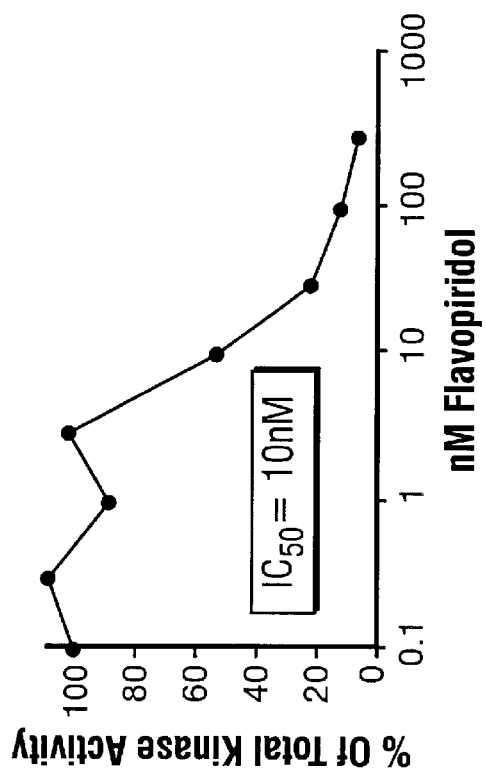
Figure 2C:
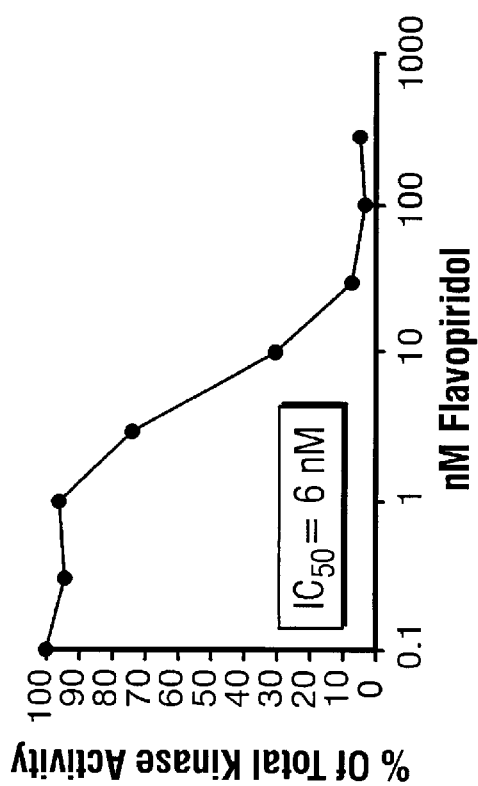
Figure 2D:
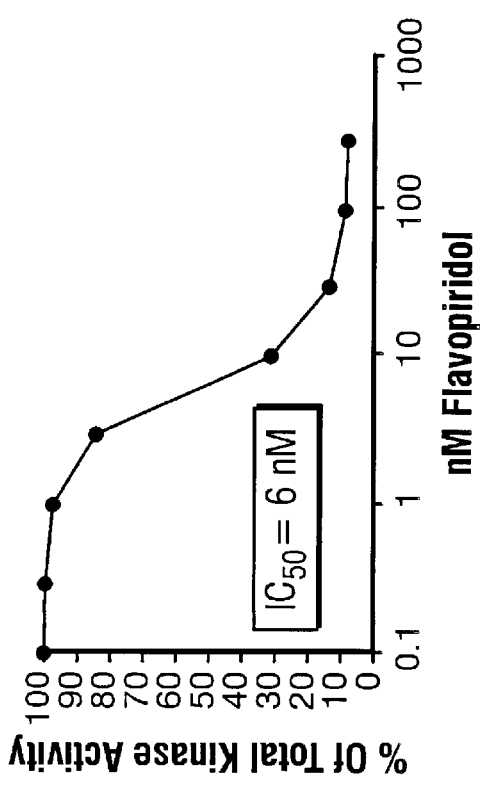

These studies showed that P-TEFb was dramatically inhibited by flavopiridol in a standard assay using 10 $\mu$M ATP (FIG. 2A). The $IC_{50}$ was calculated to be 6 nM.

Assays were also carried out using 30, 100 and 300 $\mu$M ATP. Surprisingly, the $IC_{50}$ did not vary significantly (6-10 nM) at the different concentrations of ATP (FIG. 2A, FIG. 2B, FIG. 2C, FIG. 2D). The data from FIG. 2A, FIG. 2B, FIG. 2C and FIG. 2D were fit to equations derived for competitive, noncompetitive and uncompetitive inhibition (Cleland, 1979; Dixon and Webb, 2000). The data fit uncompetitive inhibition best and gave an apparent Ki of 3 nM.

The apparent Ki of 3 nM is four orders of magnitude below the Km for ATP of 36 $\mu$M. These results indicate that flavopiridol inhibits P-TEFb much more potently than its previously suspected targets, Cdc2 and Cdk4. Flavopiridol inhibited Cdc2 (Losiewicz et al., 1994) with a Ki of 41 nM and Cdk4, with a Ki of 65 nM (Carlson et al., 1996) and with a Ki of 61 nM (Singh et al., 1999); all cases were competitive with ATP. The results also show that flavopiridol is the most effective P-TEFb inhibitor discovered to date.

EXAMPLE 2

Flavopiridol Inhibits HIV Replication

Figure 3:
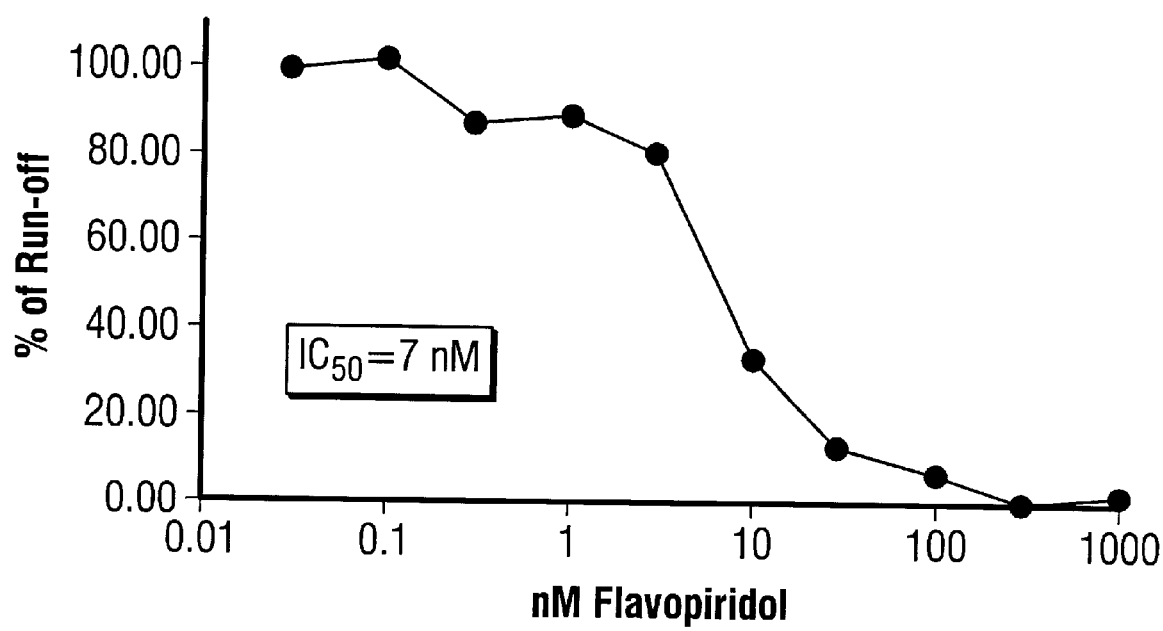
FIG. 3. Inhibitory effects of flavopiridol on HIV Tat transactivation. Continuous labeling transcription assays using the MV-1 promoter were performed as described by Zhu et al. (1997, specifically incorporated herein by reference). Autoradiographs of run-off transcripts were analyzed by denaturing PAGE. Tat (20 ng/reaction), DRB (50 $\mu$M) and flavopiridol were added to the reactions. Run-off transcripts were quantitated and $IC_{50}$ was determined as described in FIG. 1. The results shown are representative of those from more than 5 assays performed with different preparations of Tat.

Since P-TEFb is a required cellular cofactor for the HIV transactivator Tat to activate transcription of the viral genome (Price, 2000), the ability of flavopiridol to inhibit Tat transactivation was next examined. Using the HIV-1 promoter in the assay, Tat was found to stimulate the appearance of a 694-nucleotide run-off transcript from the HIV-1 promoter about 5-fold. As has been found before, the P-TEFb inhibitor DRB blocked the formation of long run-off transcripts. When increasing concentrations of flavopiridol were included in Tat transactivation reactions, the amount of run-off transcription was reduced to background levels (FIG. 3). Quantitation of the results indicated that the $IC_{50}$ was 7 nM (FIG. 3). These results are consistent with the ability of flavopiridol to inhibit the kinase activity of P-TEFb.

Figure 4A:
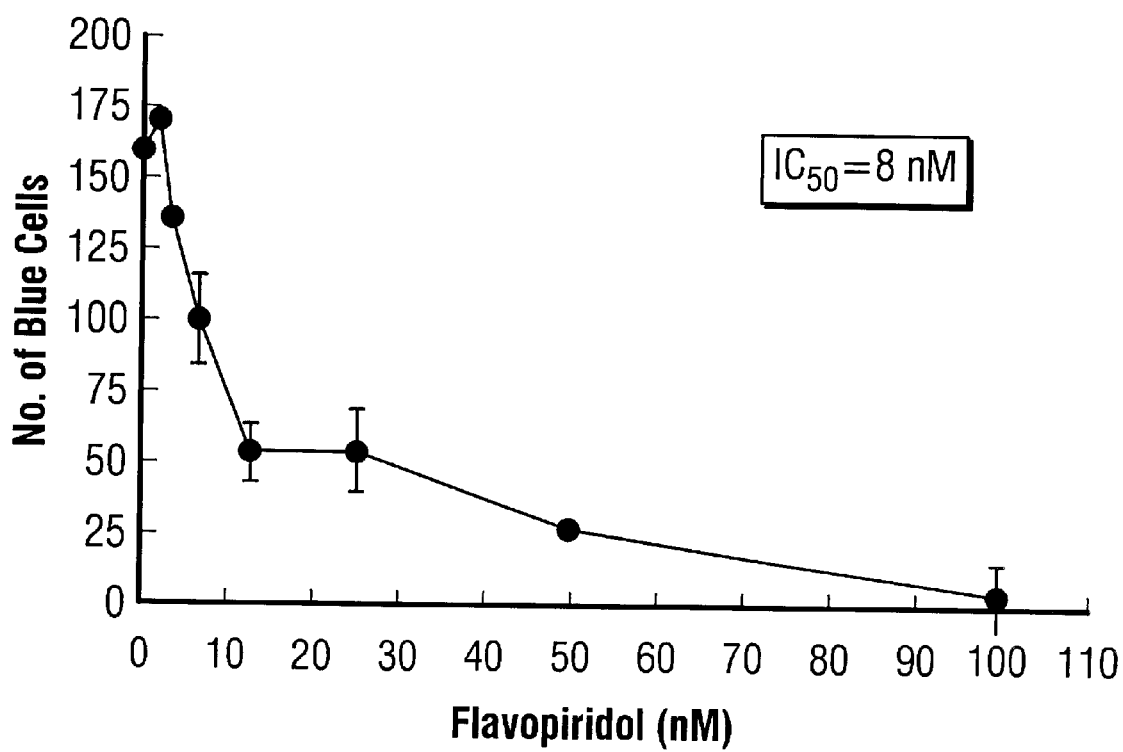
FIG. 4A and FIG. 4B. Inhibitory effects of flavopiridol on the replication of HIV-1.

Flores et al. (1999) have shown that reducing P-TEFb activity in cells, either through the expression of a dominant negative Cdk9 subunit or by treatment with small molecule inhibitors of P-TEFb, has a dramatic inhibitory effect on the ability of HIV to replicate and spread. Therefore, the effects of flavopiridol on the single round of infection by HIV-$1_{HXB2}$ in Sx22-1 indicator cells and viral replication of HIV-$1_{NL4-3}$ in Jurkat cells were examined (FIG. 4A and FIG. 4B).

Sx22-1 cells are HeLa cells that contain one copy of the HIV-1 promoter linked to the $\beta$-galactosidase reporter gene and can be efficiently infected by the HIV-$1_{HXB2}$ strain. Following the infection by HIV-1, the production of Tat leads to the expression of $\beta$-galactosidase, which is detected by the blue staining of Sx22-1 cells with 5-bromo-4-chloro-3-indolyl $\beta$-D-galatopyranoside (X-gal) (Wimmer et al., 1999; Fackler et al., 1999). The addition of flavopiridol reduced the number of blue cells to background levels and exhibited an $IC_{50}$ of 8 nM (FIG. 4A). Of note, the Sx22-1 cells remained viable even at the highest concentrations of flavopiridol (100 nM) as determined by trypan blue exclusion.

Figure 4B:
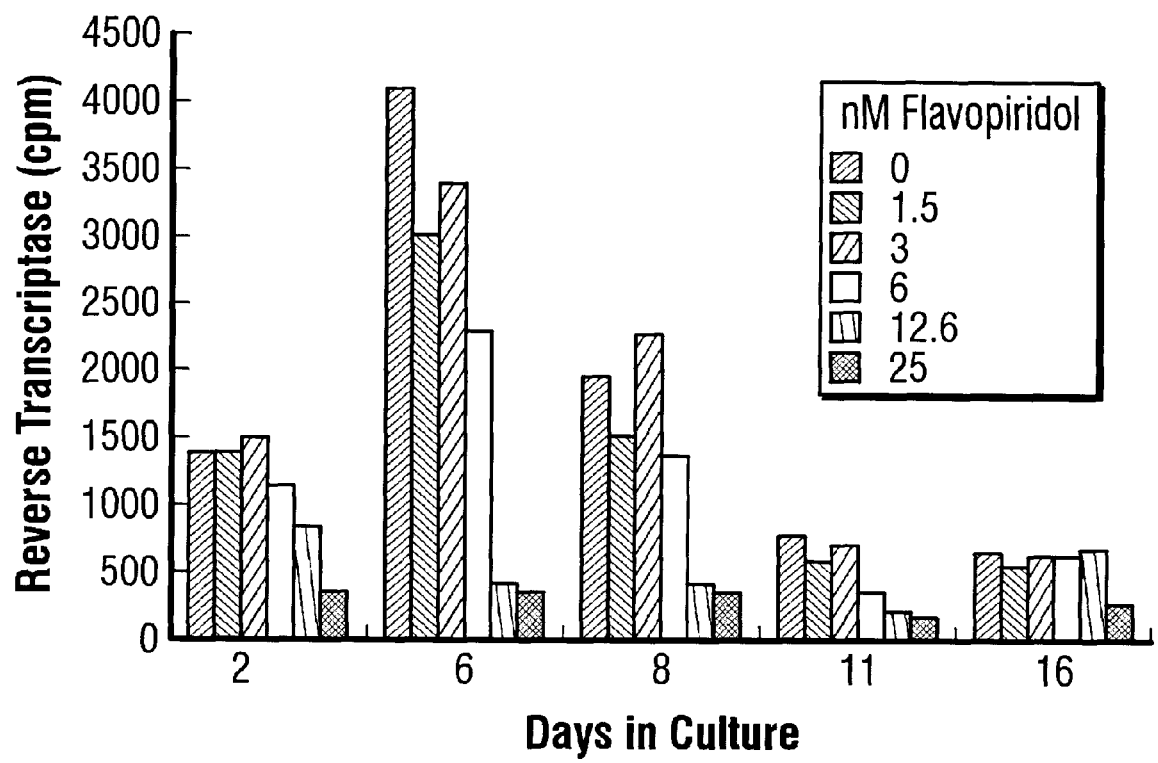

The foregoing findings were extended with a viral spread assay using Jurkat cells infected with the HIV-$1_{NL4-3}$ virus (FIG. 4B). Using high multiplicities of infection, these cells produce maximal viral titers 5 days after the initial infection, after which the cells begin to die. Reverse transcriptase assays again demonstrated that flavopiridol reduced the production of virus in a dose-dependent fashion. As was found in the single-round assay, a dramatic block of HIV-1 replication occurred at a concentration of flavopiridol between 6 and 12.5 nM (FIG. 4B). Cells that did not replicate HIV-1 remained viable at the highest concentration of flavopiridol used (25 nM).

The results presented in Example I and Example II therefore show that flavopiridol inhibits P-TEFb at low nanomolar concentrations in human cells. In fact, biochemical analyses demonstrate that P-TEFb is more potently inhibited than any other previously proposed target, including Cdk1 and Cdk4. The Ki for flavopiridol against P-TEFb of 3 nM is at least an order of magnitude lower than the Ki against either Cdk1(41 nM) or Cdk4 (65 nM). As flavopiridol is not competitive with ATP on P-TEFb, but is competitive with ATP on Cdk1 and Cdk4, there is expected to be an even greater difference in $IC_{50}$ between P-TEFbs compared with Cdk1 or Cdk4 at the high ATP levels found in vivo.

The nanomolar Ki and lack of competition with ATP indicates that the drug binds relatively tightly to P-TEFb. In light of crystal structure studies on the ATP binding site of Cdk2, it is likely that the ATP binding site of P-TEFb is targeted by flavopiridol. It is also possible that flavopiridol binds to another site and this is supported by the kinetic data that fit an uncompetitive model best. However, although of scientific interest, an understanding of the precise mode of flavopiridol binding to P-TEFb is not required to practice the invention.

These studies of Example I and Example II have two immediate implications. First, since flavopiridol affects the proliferative abilities of a number of cancer cells, this implicates P-TEFb as potentially playing a role in cancer. Second, since P-TEFb is a key factor in HIV infection, and as flavopiridol blocks HIV-1 propagation in accepted models, the present discoveries show that flavopiridol can now be used as an anti-AIDS therapeutic.

Currently, in using flavopiridol to treat cancer, the drug causes diarrhea and a proinflammatory syndrome. However, as detailed herein, the present invention provides for the selection of lower doses that achieve the nanomolar drug levels (10-20 nM) required to counteract HIV without causing such problems. Although there is a particularly urgent need for HIV-1 therapeutics, the inventive concept of using flavopiridol as a P-TEFb inhibitor is broadly applicable to the development of other anti-virals. For example, as P-TEFb is required for HIV-2, equine infections anemia virus (EIAV), simian immunodeficiency virus (SIV) and bovine immunodeficiency virus (BIV) (Taube et al., 1999), flavopiridol can be effectively used to combat such infections. In such treatments, as well as anti-HIV-1 regimens, flavopiridol has an advantage over treatment with current drugs, which often results in the selection and propagation of resistant viral strains. As the P-TEFb target is a cellular factor, it is unlikely that resistant strains will arise using the therapies of the present invention.

EXAMPLE 3

Detailed Binding Analyses

To further examine the inhibitory effect of flavopiridol on P-TEFb, the following studies were conducted. Surprisingly, flavopiridol is not competitive with ATP (Example 1). One explanation is that the inhibitor is tightly bound to the enzyme. This possibility was further suggested by the fact that the $IC_{50}$ calculated (<10 nM) was about the same as the concentration of P-TEFb in the kinase reactions. This suggested that the $IC_{50}$ was determined by the concentration of P-TEFb.

Figure 5A:
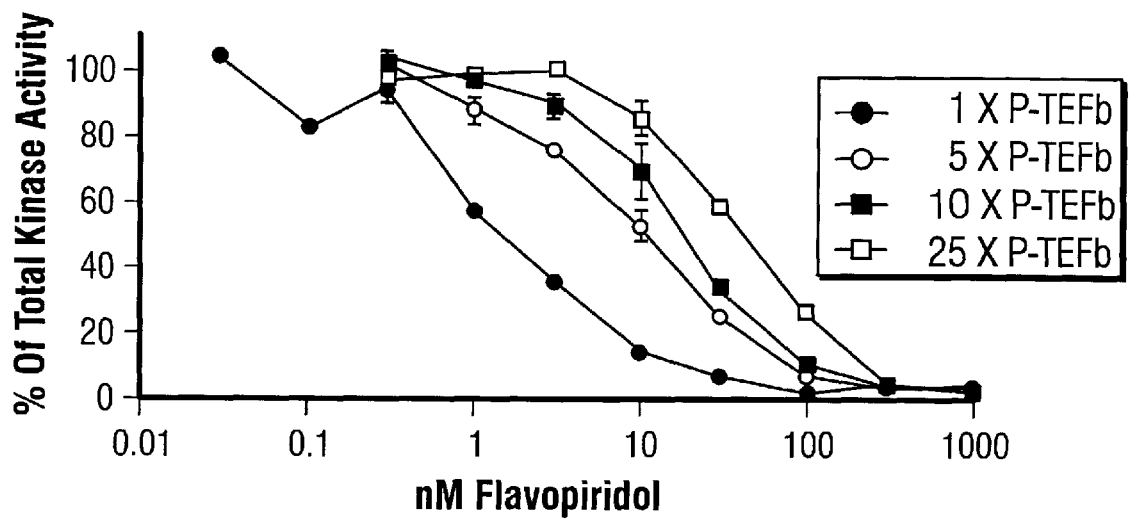
FIG. 5A, FIG. 5B and FIG. 5C. The effect of P-TEFb concentration on the $IC_{50}$ for flavopiridol. Kinase reactions were carried out at four concentrations of P-TEFb over a 25-fold range with increasing amounts of flavopiridol from 0.03 to 300 nM.
Figure 5B:
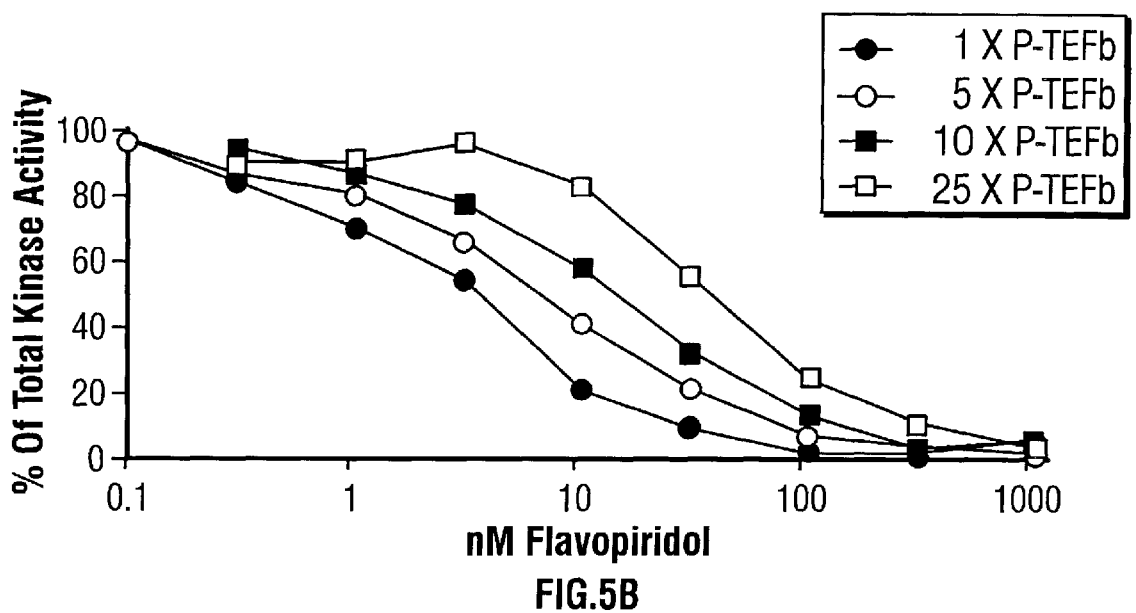
Figure 5C:
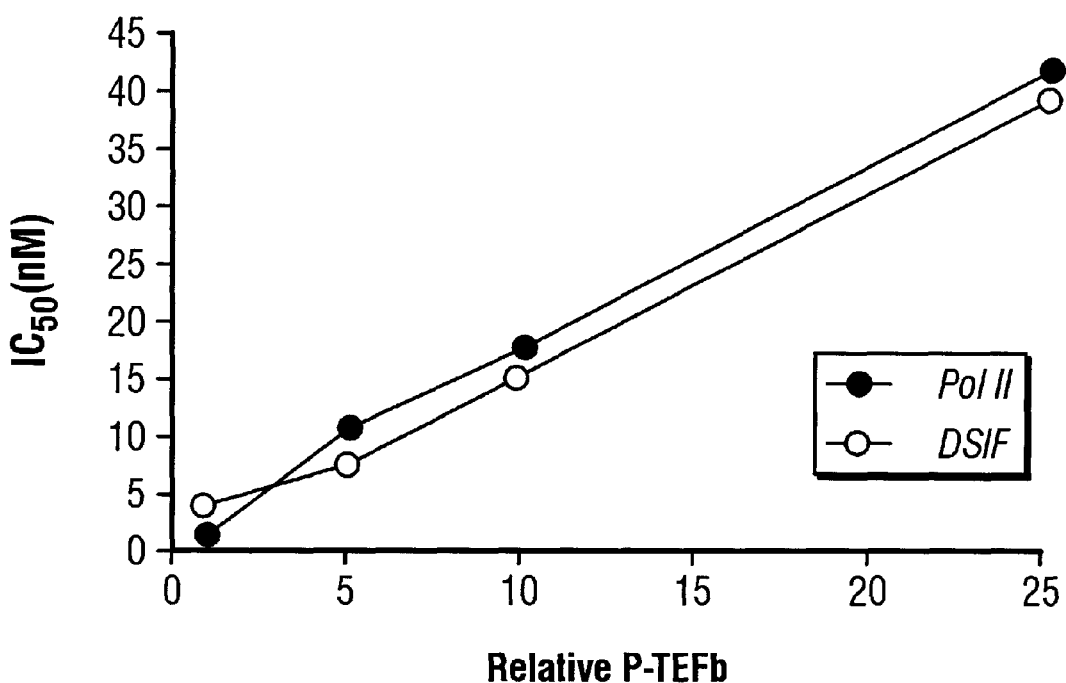

To examine this possibility, kinase assays were carried out with four levels of P-TEFb covering a 25-fold range of concentration (FIG. 5A, FIG. 5B and FIG. 5C). Using either RNA polymerase II (FIG. 5A) or a negative transcription elongation factor, DSIF (FIG. 5B), as substrate, flavopiridol was more easily able to inhibit P-TEFb when low levels of the kinase were used. A plot of the IC50 calculated versus the relative amounts of P-TEFb demonstrated that the relationship was linear (FIG. 5C).

An estimate of the absolute concentration of P-TEFb in the reactions suggests that the drug binds one to one with the enzyme. The fact that the plot in FIG. 5C does not have much deviation from linearity even at low P-TEFb concentrations indicates that the dissociation constant ($K_D$) must be less than $10^{-9}$. This tight binding is likely responsible for the finding that flavopiridol is apparently not competitive with ATP which has a $K_m$ of 37 $\mu$M.

To study the binding in greater detail, an immobilized P-TEFb assay was developed. P-TEFb comprised of Cdk9 and cyclin T1 was biotinylated using N hydroxysuccinimide ester (NHS) activated biotin (Vector Laboratories) and then coupled to streptavidin coated paramagnetic beads (Dynal Inc.). The biotinylation and immobilization did not inactivate the kinase activity of P-TEFb.

A study was designed to determine whether flavopiridol would remain bound to the immobilized enzyme during extensive washing to remove the free drug. Immobilized P-TEFb was incubated with mock drug, DRB or flavopiridol at a concentration ten times higher than their respective $IC_{50}$'s (DRB, 90 $\mu$M; flavopiridol, 400 nM). Wash conditions were utilized that gave an effective dilution of the free drug in excess of 40,000 fold within two min. If the drug was released from the enzyme during the wash it would be at a concentration below that required for inhibition. A 10 min kinase reaction was used to determine the activity of the immobilized P-TEFb.

Using RNA polymerase II as substrate either drug was able to completely inhibit the activity of immobilized P-TEFb before washing. Slightly less activity was recovered from untreated beads after washing and the inhibitory effect of DRB was completely removed. However, only 25% of the activity was recovered after washing beads treated with flavopiridol. This demonstrates that flavopiridol is tightly bound to P-TEFb and suggests that the dissociation process has a half time longer than 2 min.

Figure 6:
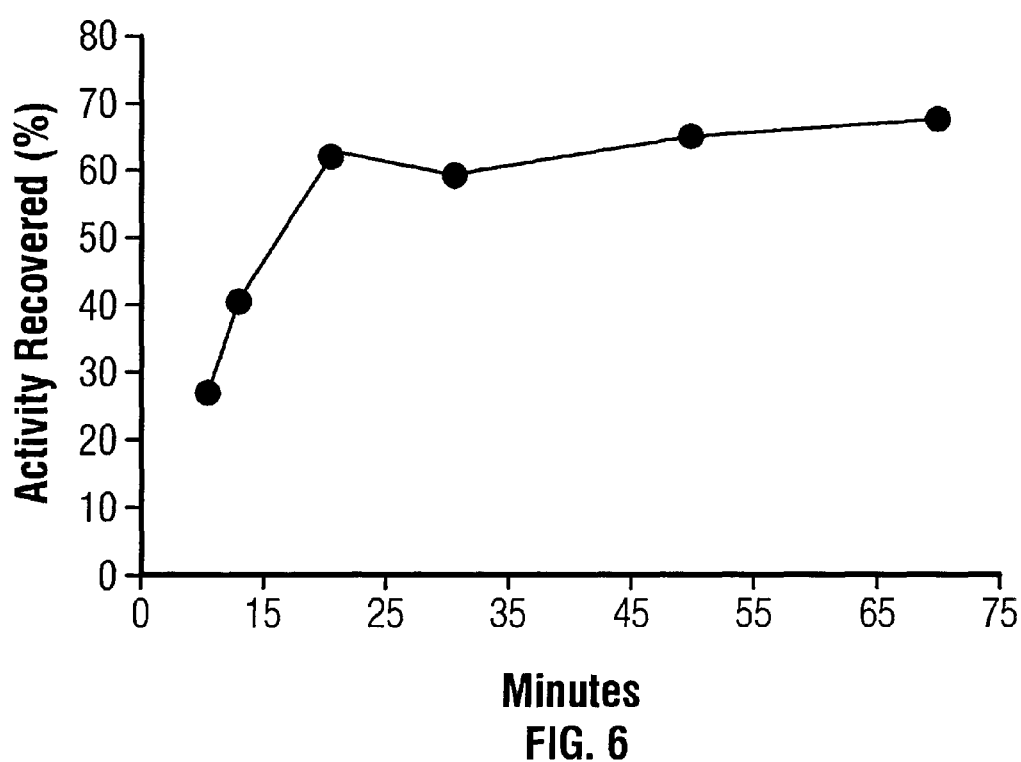
FIG. 6. Recovery of P-TEFb activity after incubation of P-TEFb beads with flavopiridol. P-TEFb-coated beads were washed and incubated under dilute conditions for increasing amounts of time. The times shown include the incubation time and the 10 minute reaction.

A study was then designed to estimate the off rate of flavopiridol from immobilized P-TEFb. Beads were treated with flavopiridol as above and washed, and were then incubated in a large volume of buffer for increasing amounts of time. The beads were re-concentrated and subjected to a 10 min kinase assay using RNA polymerase II as substrate. The fraction of activity recovered was calculated by comparing activity with beads treated with mock drug with those treated with flavopiridol and then plotted versus time (FIG. 6). The results indicate that flavopiridol binds tightly to P-TEFb and that half of the drug has dissociated in 10 to 15 min.

EXAMPLE 4

Detailed Transcription Inhibition Studies

Nuclear run-on analyses of flavopiridol inhibition of transcription were conducted to test the assumption that elongation control is a general process that functions on most genes. This assumption is based on the inhibition of the synthesis of many different mRNAs by the P-TEFb inhibitor DRB in vivo and in vitro (Price, 2000).

Figure 7A:
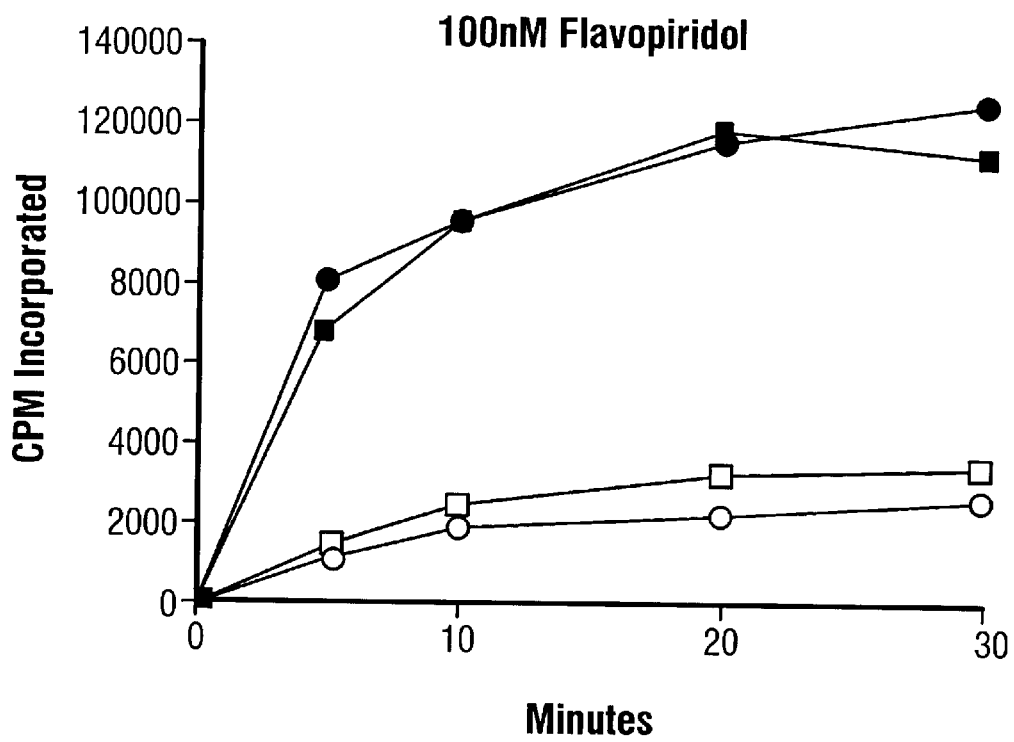
FIG. 7A and FIG. 7B. Nuclear run-on assay using 100 nM (FIG. 7A) and 300 nM (FIG. 7B) flavopiridol. Nuclei were isolated from control HeLa cells (circles) or HeLa cells treated with 100 nM (FIG. 7A) and 300 nM (FIG. 7B) flavopiridol (squares). Incorporation of $^{32}$P-GTP was measured for the indicated times in the presence (open shapes) or absence (filled shapes) of $\alpha$-amanitin. Error in individual points was 10%.
Figure 7B:
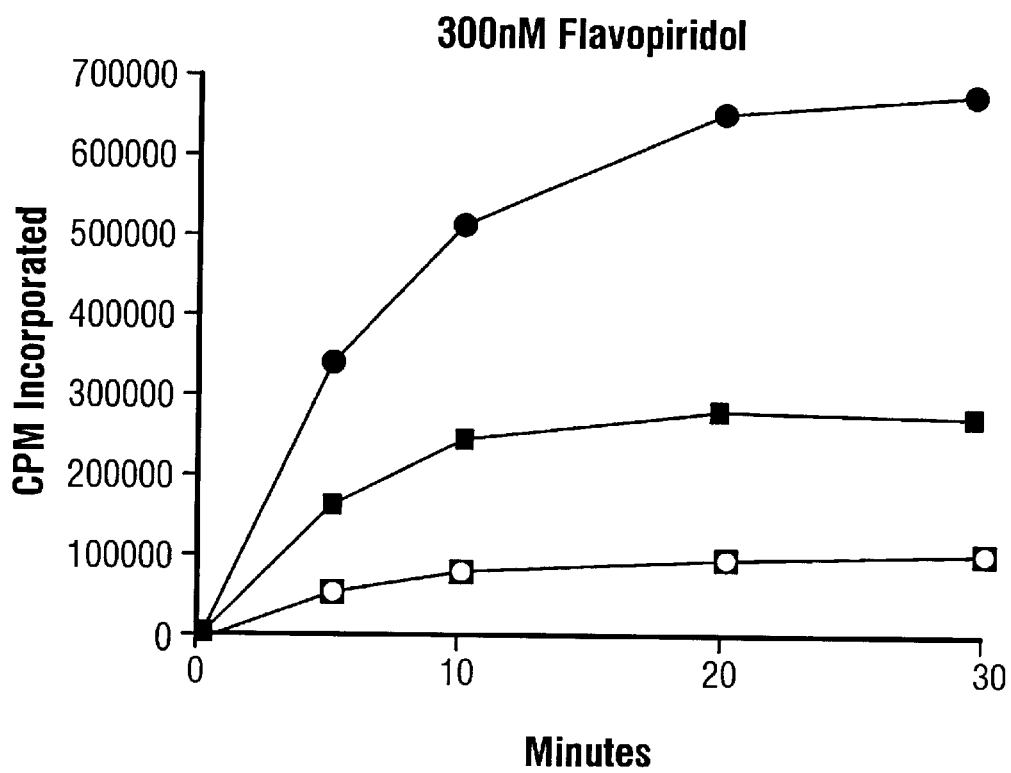

To determine the fraction of RNA polymerase II molecules that depend on P-TEFb to enter productive elongation in vivo, a nuclear run-on assay was used to compare transcription from normal cells to cells treated with flavopiridol (FIG. 7A and FIG. 7B). Nuclei were isolated from HeLa cells grown in suspension that were treated with mock drug or flavopiridol for 1 h. These are not virally infected cells. After one hour, the polymerases transcribing most genes that require P-TEFb would have reached the 3' end of the genes and would have terminated because flavopiridol does not affect elongation by polymerases that have already undergone the transition into productive elongation. The nuclei were incubated with $^{32}$P-GTP under transcription conditions that did not include detergent or high salt. With these more physiological conditions, RNA polymerase II molecules in the process of abortive elongation at the 5' end of genes are not allowed to elongate. T1 me points from large reactions incubated with or without 1 $\mu$g/ml α-amanitin were spotted on DE81 filters. After washing to remove unincorporated label the filters were counted and the results were plotted (FIG. 7A and FIG. 7B).

In FIG. 7A and FIG. 7B, total cpm (filled shapes) includes transcription by RNA polymerase I, II, and III, while transcription in the presence of α-amanitin detects only RNA polymerase I and III (open shapes). The difference between the total and the amanitin resistant counts is due to RNA polymerase II. In the two control studies shown, about 80% of the total transcription in HeLa nuclei is carried out by RNA polymerase II. When cells were treated with a high level of flavopiridol (300 nM; FIG. 7B) the signal from RNA polymerase II was reduced to about 30% of that found in untreated nuclei. These results support the assumption that the expression of most genes requires P-TEFb. It is possible that a relatively smaller fraction of the genes are affected if those genes are the most heavily transcribed, but this possibility can be addressed.

A very different result was obtained when cells were treated with 100 nM flavopiridol (FIG. 7A). In this case, little affect on RNA polymerase II transcription was found as indicated by comparing the total counts for nuclei isolated from control and flavopiridol treated cells. In this preliminary study, it is possible that the number of nuclei obtained from the flavopiridol treated cells was slightly greater than from the control cells (indicated by the increase in amanitin resistant counts). If the total counts are normalized to the amanitin resistant counts, then a slight inhibition (10%) of RNA polymerase II transcription is possible.

The $IC_{50}$ for flavopiridol on RNA polymerase II transcription in vivo can be estimated from these two studies to be between 100 and 300 nM. This is in sharp contrast to the $IC_{50}$ of below 10 nM for HIV in infected cultured cells. Importantly, these studies indicate that expression of the HIV genome is 10 to 30 times more sensitive to flavopiridol than transcription of normal cellular genes. This is very encouraging for the in vivo use of flavopiridol in the safe and effective treatment of HIV infections, particularly using doses of flavopiridol below those typically used in cancer patients.

EXAMPLE 5

Immunolocalization Studies

An important aspect of the function of any protein is its subcellular location. A preliminary localization of Cdk9 was thus carried out (in collaboration with Dr. Charlotte Spencer at the University of Alberta). Confocal images were obtained of cells stained with DAPI to visualize nuclei and anti-Cdk9 antibodies. Antibodies against the C-terminal 20 amino acids of Cdk9 were used. DAPI gave a blue color and the anti-Cdk9 antibodies gave a green signal. The two images could therefore be overlaid in merged fashion.

The results indicate that Cdk9 is predominately nuclear as previously reported, but significant punctate cytoplasmic staining was observed. The cytoplasmic form of Cdk9 may or may not be complexed with a cyclin and may or may not have activity. The characterization of cytoplasmic versus nuclear Cdk9 can be achieved.

EXAMPLE 6

Kinetic and Structural Analyses

The properties of flavopiridol on the kinase activity of P-TEFb are unusual in that the inhibitor is not competitive with ATP (Chao et al., 2000). Thus, flavopiridol likely binds very tightly to P-TEFb. The present example provides biochemical techniques to more precisely define the mechanism and selectivity of flavopiridol inhibition of P-TEFb and to explain why HIV is more sensitive to the drug than cellular genes. The structural information also provides for the development of additional and even improved P-TEFb inhibitors.

1. Kinetic Parameters of Flavopiridol Inhibition.

P-TEFb has multiple forms and interacts with a number of factors during its normal cellular function in controlling elongation by RNA polymerase II and as a co-activator of HIV transcription (Price, 2000). Flavopiridol and all other P-TEFb inhibitors block transcription of the HIV genome more effectively than expression of cellular genes (Mancebo et al., 1997; Flores et al., 1999; Chao et al., 2000) and it is possible that the inhibitory activity of flavopiridol is modulated by proteins that interact with Cdk9.

The crystal structure of Cdk2 with a close derivative of flavopiridol indicates that the compound binds to the ATP binding site (De et al., 1996; Kim et al., 1996). When the structure of Cdk2 with and without a cyclin subunit are compared, it is clear that a region of Cdk2 that is adjacent to the flavopiridol binding site is significantly modified. This suggests that the cyclin subunit of P-TEFb may influence the binding of flavopiridol to the kinase subunit. This is investigated using recombinant P-TEFb comprised of Cdk9 and each of the three cyclins known to activate Cdk9 (cyclin T1, T2 and K).

Powerful assays for this include kinase assays using recombinant P-TEFb and one of several substrates that include RNA polymerase II and DSIF; and transcription assays using a whole HeLa extract that has been depleted of P-TEFb. Both assays can be programmed with any of the three forms of P-TEFb. The transcription assay can be further modified by using different templates. In addition, a number of modified transcription systems can be used that utilize immobilized templates and more defined sets of factors (Peng et al., 1998a; Xie and Price, 1996; Marshall and Price, 1992).

Flavopiridol titrations in kinase assays with Cdk9/cyclin T1, Cdk9/cyclinT2 and Cdk9/cyclin K, using both RNA polymerase II and DSIF individually as substrate, are informative. Care must be taken to use identical levels of Cdk9 in such comparative studies since the $IC_{50}$'s determined in kinase assays are in part determined by the concentration of P-TEFb. The details of the relationship between $IC_{50}$ and the concentration of P-TEFb containing each of the cyclin subunits are thus determined. Some of the enhanced inhibition of HIV may be due to inability or reduced ability of flavopiridol to inhibit P-TEFb comprised of Cdk9 and either cyclin T2 or K.

P-TEFb functions at the HIV-1 promoter by association with HIV-1 Tat protein and potentially other factors (Price, 2000), so the effect of Tat, TatSF 1, DSIF and NELF on the inhibitory properties of flavopiridol is determined. Tat has an effect on the kinase activity of P-TEFb toward RNA polymerase II. The viral protein dramatically stimulates the extent of phosphorylation of the CTD of the large subunit of RNA polymerase II and changes the sight of phosphorylation from predominately Ser 2 to Ser 2 and 5 in the $YS_2PTS_5PS$ repeat (Zhou et al., 2000; Garber et al., 2000). Kinase assays in the presence of increasing concentrations of flavopiridol are performed on the three forms of P-TEFb with and without Tat. In addition, similar assays are performed in the presence of other proteins known or suspected to be involved in Tat transactivation, such as TatSFI, DSIF and NELF. Effects in vivo in the absence of effects in kinase assays can be addressed (see below).

In vitro transcription assays in which transcription from the CMV promoter is compared to that from the HIV-LTR are further useful. P-TEFb is required for long transcripts to be produced from both promoters, but the HIV-LTR requires Tat for maximum production of run-off transcripts. Transcription from both promoters is carried out under identical conditions with and without Tat. The appearance of run-off transcripts in the presence of increasing concentrations of flavopiridol is quantified and $IC_{50}$'s determined. A comparison of the $IC_{50}$'s against CMV and HIV-LTR plus Tat is made to determine whether there is an enhancement of sensitivity to flavopiridol. A comparison of the runoff from the HIV-LTR with and without Tat determines whether all transcription from the HIV-LTR or just Tat activated transcription is differentially affected by flavopiridol.

Key transcription studies are performed in the presence of increasing concentrations of ATP to determine whether inhibition of P-TEFb function is independent of ATP concentration. This is necessary because it is a possibility that the factors present in the nuclear extract might affect the ability of the kinase to be inhibited by flavopiridol. Any such change in the properties of P-TEFb would lead to the purification of the proteins(s) responsible using the immobilized P-TEFb assay (see below). A shift of $IC_{50}$ of 3 fold or more toward greater sensitivity by factors in the extract is informative.

2. Association of Flavopiridol and Factors with Immobilized P-TEFb

P-TEFb immobilized to paramagnetic beads (Example 3) is used to uncover details of the inhibition of Cdk9 by flavopiridol and to determine whether protein factors influence the binding of flavopiridol. Flavopiridol binds tightly to P-TEFb (FIG. 6), suggesting that P-TEFb is inhibited with a one to one ratio of the drug to P-TEFb. It is possible that Tat or other proteins increase the time that flavopiridol is bound to P-TEFb by decreasing the off rate of the drug. It is also possible that flavopiridol may affect the association of protein factors with P-TEFb.

To determine baseline parameters of flavopiridol interaction with P-TEFb, binding assays are performed in which flavopiridol is bound to immobilized P-TEFb, free flavopiridol quickly washed away and then the P-TEFb flavopiridol complex incubated in a relatively large volume of buffer that allows dissociation of the drug. At various times after the complexes are diluted they are concentrated and assayed using RNA polymerase II or DSIF as substrate in a kinase reaction. A plot of activity recovered with time is used to calculate the time it takes to recover half of the P-TEFb activity ($t_{1/2}$). The time of the kinase assay is minimized to reduce the continued dissociation of the drug during the reaction, allowing a better determination of the $t_{1/2}$ for dissociation.

The effects of salt and ATP on flavopiridol binding to P-TEFb are determined by diluting the P-TEFb/flavopiridol complex into a solution that contains increasing concentrations of salt or ATP. The P-TEFb is concentrated and assayed for recovery of activity and kinetics. If the predominant interaction between flavopiridol and P-TEFb is hydrophobic, then increasing salt may increase the dissociation time; and if ionic interactions are involved, then increasing salt may decrease the dissociation time. If flavopiridol binds to the ATP binding site on P-TEFb, the effect of including ATP in the dissociation reaction may be small due to the fact that flavopiridol is occupying the site to which ATP binds, and only after flavopiridol dissociates would ATP be able to bind. However, if flavopiridol binds to another site on P-TEFb, then ATP might have a positive or negative effect on flavopiridol dissociation. Results from dissociation in the presence of ATP thus provide evidence for the mechanism of inhibition of flavopiridol. If ATP has no effect, then a model in which the drug binds to the ATP site is favored; and if ATP has an effect (either positive or negative), then a model in which the drug binds to another site is favored.

The influence of various factors, such as Tat, TatSF 1, DSIF and NELF, on the rate of dissociation is determined. It is possible that Tat changes the conformation of P-TEFb such that it has a higher affinity for flavopiridol. In this way, any flavopiridol inside a cell infected with HIV would bind to P-TEFb that has Tat associated and that complex would then be inactive toward the HIV-LTR. This could explain the fact that low levels of flavopiridol block HIV transcription, but not cellular gene transcription because only the P-TEFb with Tat bound would be affected.

In addition to purified factors, whole HeLa cell nuclear extracts are used as a source of potential P-TEFb binding factors. Extracts with or without Tat added are incubated with beads containing P-TEFb/flavopiridol complexes for increasing amounts of time, the beads are quickly rinsed to remove most protein and assayed for kinase activity recovered. Positive or negative effects on dissociation lead to fractionation of the extract and purification of the necessary component(s), such as in the purification and cloning of S-11 (Sluder et al., 1989; Marshall et al., 1990; Guo and Price, 1993), TFIIF (Price et al., 1989; Kephart et al., 1993), factor 2 (Xie and Price, 1996; Liu et al., 1998), and P-TEFb (Marshall and Price, 1995; Zhu et al., 1997; Peng et al., 1998b; Peng et al., 1998c). Identified activities are tested for their requirement in Tat transactivation or elongation control in general using standard transcription assays.

Just as protein factors may influence flavopiridol binding, it is also possible that flavopiridol may influence protein binding. To examine this possibility and to discover factors involved in enhanced sensitivity of Tat transactivation, immobilized P-TEFb is used in pull down assays with purified factors and with whole HeLa extracts. Differences in proteins associated with unliganded P-TEFb and with the P-TEFb/flavopiridol complex are sought in assays performed with and without Tat. Material bound to P-TEFb is analyzed by silver stained protein gel and by Western blot using antibodies to Tat, TatSFI, DSIF and NELF. The influence of bound proteins on the kinase activity of P-TEFb, or on the dissociation of flavopiridol, is determined and such factors purified.

3. Structural analysis of flavopiridol binding to P-TEFb

Significant information about the association of flavopiridol is obtained from a structural analysis of P-TEFb with and without the drug bound. Knowing the interaction surfaces of both the protein and the drug allows the prediction of the mechanism of inhibition and the potential role of the cyclin subunit or Tat in changing the interaction. Structural information also makes it possible to rationally design other compounds that have higher bioavailibility and other improved pharmacokinetic parameters, i.e., allows drug optimization (Gane and Dean, 2000).

P-TEFb is purified from baculovirus infected Sf cells (Peng et al., 1998b; Peng et al., 1998c). To eliminate a heterogeneous population of molecules due to proteolysis of the carboxyl terminal region of cyclin T1, and to reduce the overall size of the protein for crystallization, a baculovirus construct that expresses Cdk9 (HIS tagged) and a truncated cyclin T1 (amino acids 1-280) is used. Drosophila P-TEFb with such a truncated cyclin forms a strong heterodimer and has all the domains required to function during transcription (Peng et al., 1998b). Importantly, a similarly truncated human cyclin T1 functions well in Tat dependent binding to TAR and in Tat transactivation of the HIV-LTR in vivo (Garber et al., 1998b). Recombinant P-TEFb can also be produced from *Pichia pastoris* systems (Invitrogen Inc.), which produce high levels of proteins in yeast.

Active P-TEFb containing a truncated cyclin T1 is shown to be pure by electrophoretic and chromatographic methods and dynamic light scattering is used to check for the dispersive properties of the prepared protein. Mono-disperse preparations favor crystallization over poly-dispersive samples (Chayen et al., 1996). Protein crystallization can be achieved using the Hampton screening kits and an incomplete factorial method (Abergel et al., 1991) is used to vary promising conditions to optimize the production of high quality crystals. Micro-seeding and macro-seeding can be employed to improve the crystals. Lipid cubic phases, which form a three dimensional grid that has been successfully exploited in the crystallization process (Landau and Rosenbusch, 1996), enables the growth of crystals that diffract to much better resolution from poorly diffracting crystals (Luecke et al., 1999).

Well diffracting crystals yield structural determinations. Initial X-ray diffraction data is collected using a rotating anode X-ray generator, osmic confocal mirrors and an RAXIS IV++ detector. Structure solution is done by the method of multiple isomorphous replacement and/or multi-wavelength anomalous dispersion using the LII edge of soaked heavy atoms (Ingelman et al., 1999). The production selenomethionine substituted proteins (Kauppi et al., 1998) is achieved using a baculovirus system (Bellizzi et al., 1999).

EXAMPLE 7

Inhibition of HIV Gene Expression Exceeds that of Normal Cellular Genes

Data concerning the function of P-TEFb are consistent with a requirement for transcription of most genes transcribed by RNA polymerase II (Price, 2000). In one study, Drosophila P-TEFb was found to be physically associated with hundreds of transcribed genes including HSP70 (Lis et al., 2000). The present example describes the determination of the levels of mRNA in cells treated with flavopiridol using DNA microarray methodology, supplemented by the use of isolated nuclei to examine the effect of flavopiridol directly on mRNA transcription and thereby eliminate indirect effects of the drug. Although the target of flavopiridol is a cellular factor controlling gene expression, the comparative effects of the drug on normal cellular transcription and HIV transcription show that an effective window of therapeutic intervention exists.

1. Direct Effects of Flavopiridol on Transcription by RNA polymerase II

The fraction of genes in a standard tissue culture cell line inhibited by flavopiridol is determined using nuclei isolated from HeLa cells treated with 0, 10, 30, 100, 300, and 1000 nM flavopiridol for 1 h. Nuclear run-on assays (Marzluff, 1990) are performed in the absence and presence of 1 µg/ml α-amanitin. The amount of α-$^{32}$P-GTP incorporated into RNA is determined after 0, 5, 10 and 20 min. RNA polymerase II transcription is quantified by taking the difference between total RNA synthesized and RNA synthesized in the presence of α-amanitin.

Studies indicate that in isolated HeLa nuclei about 80% of the total RNA synthesis is carried out by RNA polymerase II (FIG. 7A and FIG, 7B). A 1 h treatment with the drug is appropriate because flavopiridol, like DRB, rapidly enters cells and inhibits P-TEFb (Egyhazi et al., 1996). In the absence of P-TEFb, RNA polymerase II will no longer enter productive elongation on genes that require the factor. However, polymerases that have made the transition into productive elongation before the drug is added will continue elongation until they reach the 3' end of the transcribed gene. RNA polymerase II elongates at about 1,500 nucleotides per min and, therefore, after one h should have been cleared from the vast majority of genes. Since the run-on assay is essentially a measure of the polymerase density along a gene, there should be no signal from genes that require P-TEFb so long as P-TEFb is completely inhibited and the gene is less than 90 kbp long (60 min at 1.5 kb/min). To validate the 1 h treatment, the cells are also treated with 1000 nM flavopiridol for 15, 30, 90, and 120 min and the amount of amanitin sensitive transcription remaining quantified.

Interpretation of the results from nuclear run-on studies is informative. Examination of the effect of high levels of flavopiridol on total RNA polymerase II synthesis gives a global picture of what fraction of the polymerases require P-TEFb to elongate efficiently. The nuclear run-on analysis has the advantage that it can be performed very soon after the addition of the drug, so that the effects of lethal doses can be measured before the cell is dramatically affected. Methods that detect mRNAs require longer treatment times, so that the RNA that existed before the drug was added can turnover. Drugs that have lethal effects on cells can have very strong secondary effects on mRNA levels. For example, flavopiridol might directly inhibit only a few genes that are required for normal cellular function, but might affect all mRNA levels due to the activation of apoptotic pathways. The nuclear run-on assay avoids this problem by a direct readout of the primary effect.

The effects of flavopiridol on the transcription of individual genes are also determined, including genes covering a range of sensitivity to flavopiridol from highly sensitive (like HIV) to moderately sensitive or resistant. Oncogenes such as c-myc (Miller et al., 1989) and c-fos (Collart et al., 1991) that have been demonstrated to be controlled at the elongation stage, and cyclin $D_1$ (Carlson et al., 1999) that has been shown to be affected by flavopiridol, are examined. The transcription rate of any particular gene can be determined by hybridization of the labeled RNA to gene specific probes immobilized on nitrocellulose.

A slot blot device is used to load 1 µg per slot of PCR™ amplified cDNA from genes selected from microarray studies (see below). RNA from a preparative scale nuclear run-on assay is hybridized to the filter. Conditions are used that maximize the efficiency of hybridization, so that the amount of labeled RNA bound is directly related to the transcription rate in vivo. After stringent washing, the filters are analyzed with a Packard InstantImager. Absolute transcription rates are calculated taking into account the efficiency of detection by the imaging device, the number of nuclei used, the specific activity of the labeled nucleotide and the length and nucleotide content of each cDNA. rRNA synthesis is used as a control since it is not be affected by flavopiridol. Each reaction has similar numbers of nuclei that have been treated with different amounts of flavopiridol. The transcription rate of rDNA and other unaffected genes will not change, but affected genes will show reduced rates of transcription.

2. DNA Microarray Assays Examine the Effect of Flavopiridol on Gene Expression

To determine whether the expression of any normal gene is meaningfully inhibited by flavopiridol at the low concentrations shown to be effective against HIV, microarray technology is used. Basically, the method determines the relative concentration of mRNA from many genes at once. It is necessary to treat cells for more extended periods of time compared to those used in the isolated nuclei studies above. Since the half life of many mRNAs is about 3-5 h, cells are treated for at least 10 h before isolating mRNA using low and intermediate flavopiridol concentrations, particularly using long term treatment with low drug concentrations. These techniques are highly complementary, as nuclear run-on assays examine direct effects at high levels of drug and DNA microarray analyses determine quantitative effects on the expression of specific genes after treatment with low doses of the drug for long times.

The Affymetrix GeneChip system, which allows the simultaneous analysis of 12,000 human genes, may be used. Essentially all genes that have been functionally identified are included in the U95A array. Each gene is represented on the chip by a set of 16 to 20 primers nucleotides in length that hybridize to different regions of each cDNA. A primer containing a single mismatch at nucleotide 13 acts as a negative control for each of these primers. cDNA is synthesized from 10 µg of total RNA isolated from the cells to be analyzed. The cDNA mixture is then transcribed by T7 RNA polymerase in the presence of biotinylated nucleotide. After fragmentation, the cRNA is hybridized to the ~500,000 oligos on the 1 cm$^2$ chip. The chip is then washed and stained with a fluorescent protein, Streptavidin phycoerythin, before being scanned by a laser.

A high resolution image of the chip is produced and the signal from each gene is analyzed by proprietary GeneChip software. The software uses a variety of algorithms to call mRNAs from each gene as present or marginal or absent and takes into account the signal from the mismatched probe, a general background and noise, and other parameters. Two sets of data can be compared using normalization or scaling techniques. A difference call is determined by a comparison algorithm that indicates each mRNA is either increased, marginally increased, not changed, marginally decreased, decreased. Alternatively, a fold change for each mRNA can be calculated.

The microarray assays involve comparing three types of cells treated with different levels of flavopiridol for different times. Initially, HeLa cells are used as a general measure of the effect of flavopiridol on an average growing cell. The cells are grown in 100 ml spinner flasks under highly controlled conditions to minimize any extraneous factors that might affect gene expression. Cells in logarithmic growth are treated with 3 different concentrations of flavopiridol for 10 h. Total RNA is isolated from untreated cells and from cells treated with flavopiridol using a TRIzol protocol followed by a clean up step utilizing the Qiagen RNeasy Total RNA isolation kit. 10 $\mu$g of total RNA is used in the synthesis of the cDNA, in vitro transcription, hybridization, staining and scanning.

Each probe preparation is tested using the Test2 GeneChip that contains 5', middle and 3' regions of several housekeeping genes to confirm that the cDNA has an appropriate ratio of full length to short products. Each probe is hybridized to a Human Genome U95A Array (HG-U95A from Affymetrix) and analyzed using the GeneChip software. Results from each of the treated cell probes are compared to the untreated control. A list of mRNA concentrations for each gene at each concentration of flavopiridol is compiled. Genes that are not affected by flavopiridol are used as a scaling factor that normalizes each dataset to those genes. Other control methods are also suitable (Holstege et al., 1998).

The long term effects of flavopiridol treatment on HeLa cells and human T cells and macrophages are determined to show the safety of treating patients with flavopiridol for long periods at low doses. The effect of treatment of HeLa cells grown in suspension for 1 wk with nM flavopiridol are examined. As the cells grow, every day new medium is added with fresh flavopiridol. The growth rate is monitored and any morphological differences between treated and control cells noted. After one wk, total RNA is isolated from control and treated cells. Microarray analysis of gene expression is performed as described above.

T cells and macrophages are particularly relevant physiologically and may be isolated and cultured as described (Maury, 1994; Maury, 1998). Peripheral blood lymphocytes (PBLs) are isolated from peripheral blood mononuclear cells (PBMCs) obtained from HIV- and HBV-individuals. The PBLs containing CD4+T cells are activated with PHA for 48 h and cultured in the presence of IL-2. Monocytes are obtained by adherence of PBMCs to fibronectin coated flasks. Adherent monocyte derived macrophages are cultured for six days. The cultured cells are treated with 0, 10, 30, or 100 nM flavopiridol with replacement of the media every 2 or 3 days. Macrophages are monitored for changes in adherence properties or morphology. T cells are monitored for changes in growth rate or morphology. After treatment with flavopiridol for 1 wk, total RNA is isolated as described above for HeLa cells and subjected to DNA microarray analysis.

EXAMPLE 8

Formulation of Flavopiridol

Flavopiridol may be used in any effective formulation desired. Originally, a cyclodextrin vehicle was employed by the supplier and such formulations have been used in infusional trials. However, the following formulations represent those currently believed to be preferred for use.

Flavopiridol (IND, NSC 649890) is supplied by Hoechst, Marion, Roussel, Cincinnati, Ohio, and is a formulated product, not bulk. Flavopiridol is supplied as a sterile, yellow-colored 10 mg/ml solution in flint glass vials with elastomeric closures. Each vial contains 54.5 mg of HMR 1275, which is equivalent to 50 mg of the free base. The pH of the solution is 2.6 to 3.4. The solution also contains acetic acid and Water for Injection.

For preparation, the contents of the vial are preferably diluted prior to infusion with 0.9% Sodium Chloride Injection USP or 5% Dextrose Injection USP to final concentrations typically ranging from 0.09 to 1.0 mg/ml HMR 1275 (free base equivalent). For use in the present anti-HIV therapies, significantly lower concentrations may be employed, e.g., 0.01 to 0.04 mg/ml. The diluted solutions are iso-osmotic and the pH is about 3.5.

For storage, the vials are stored at room temperature (25° C. to 30° C.) and protected from sunlight. The stability of flavopiridol is such that the shelf-life is not problematical. Dilute solutions of flavopiridol show no change in physical appearance or chemical potency when stored in polyvinyl chloride infusion bags for 4 days at room temperature. Dilute solutions of flavopiridol were challenged with microbes to simulate potential contamination during extended infusion. Results showed no microbial growth over a six-day period at room temperature in solutions of 0.91 mg/ml. Dilute solutions of flavopiridol are compatible with silicone elastomer tubing, Becton-Dickinson filter needles, polyurethane tubing, and CADD administrations sets.

For intravenous administration, doses of flavopiridol are administered as a bolus over 60 minutes. The daily dose of flavopiridol is diluted in 100 mls of 0.9% sodium chloride for Injection, USP and is administered over 60 minutes daily for five days into a running IV of 0.9% Sodium Chloride of 100 ml/hr. The running IV is started just prior to administration of flavopiridol and is continued for at least 30 minutes after the flavopiridol bolus is completed. Although the foregoing injectable and infusional formulations are easily prepared and used, flavopiridol can also be advantageously prepared for oral, subcutaneous and intranasal administration for use in anti-HIV and AIDS therapies.

EXAMPLE 9

P-TEFb Function During HIV Infection of Human Macrophages and T cells

The present example concerns further information regarding the function of P-TEFb in cells normally infected by HIV and the use of flavopiridol to block HIV in vivo using an art-accepted animal model.

1. Primary Human Cells

HIV-1 infects primarily CD4+T cells and macrophages, but there are significant differences between the two types of cells and their ability to support productive HIV infection (Finzi and Silliciano, 1998). The two cell types have different chemokine receptors on their surface and a specific interaction between the HIV-1 gp120 protein and the receptor is required for entry of the virus (Ross et al., 1999; Carrington et al., 1999). There are T cell and macrophage tropic HIV-1 strains that differ in the chemokine receptors that they recognize (Roda Husman and Schuitemaker, 1998), but single amino acid changes in the gp120 protein can change the tropism (Boyd et al., 1993).

After the virus has gained entry into the cell, viral dynamics are different between T cells and macrophages (Finzi and Silliciano, 1998). In an infected individual, $10^7$ to $10^8$ CD4+T cells are infected each day and then die. Productive infections occur in activated, proliferating T cells, but viral entry can occur before activation and viruses can remain in a latent form in activated cells that have re-entered the resting state as memory cells. Circulating monocytes do not seem to be highly infected, but after differentiation into non-dividing macrophages (especially those found in the lymph tissues) are readily infected, but not killed by the infection. One of the major problems in AIDS patients is the reduction of CD4+T cells, but it is the subject of debate whether the bulk of the viral particles are produced by T cells or macrophages. P-TEFb expression and flavopiridol effects are thus examined in T cells and macrophages.

To understand the form and activity of P-TEFb, a combination of quantitative western blots, immunoprecipitations and immunolocalizations are used to compare P-TEFb in HeLa cells to that in T cells and macrophages. HIV may encounter a different P-TEFb environment in each type of cell, which might have an impact on its ability to carry out a productive infection. To analyze the forms of P-TEFb present and their activity, the absolute number of molecules/cell is determined for Cdk9, cyclin T1 and cyclin T2, as well as the location of these molecules in the cell (cytoplasmic vs. nuclear) and the activity of P-TEFb complexes isolated from the cells. The effect of flavopiridol and HIV infections on these parameters is then determined. To more accurately describe the role of P-TEFb in the HIV infection process, effects that cause a change in the location or activity of P-TEFb, especially in the presence of HIV Tat, are important.

In such studies, high quality antibodies are used, such as monoclonal antibodies to Cdk9, cyclin T1, cyclin T2 and cyclin K that recognize both the denatured and native proteins (Zhu et al., 1997; Fu et al., 1999; Peng et al., 1998c). A preliminary characterization showed that about 80% of P-TEFb in HeLa cells was comprised of Cdk9 complexed with cyclin T1 and most of the rest contained cyclin T2. Quantitative western blotting of HeLa cells grown in suspension involves lysing a large sample with a known number of cells with SDS, running aliquots with amounts increasing by a factor of 2 in a gradient protein gel and blotting onto nitrocellulose with known amounts of recombinant P-TEFb containing either T1, T2a, T2b, or K loaded with the same factor of 2 titration. The blot is probed with one of the antibodies and developed with chemiluminescent reagents. Films are produced and scanned and the scanned image is quantified by comparing the signals from the standards of similar intensity to that of the signal in the cell extract, thus calculating the number of molecules per cell (Kimura et al., 1999).

The location of the proteins is determined using immunofluorescence (Maury et al., 1998). Preliminary results suggest that P-TEFb is located predominately in the nucleus, but at least partially in the cytoplasm. P-TEFb is not diffusely localized, but is rather found in discrete locations within the cytoplasm and the nucleus. Localization studies with and without flavopiridol provide information on the localization pattern. For example, if the cytoplasmic form of P-TEFb is an inactive form, it is possible that treatment with flavopiridol will cause the cell to attempt to increase P-TEFb activity and a movement of the cytoplasmic form into the nucleus may be seen.

To determine how much P-TEFb activity is present in the cells, immunoprecipitation followed by kinase activity determination is used (Peng et al., 1998c)(Garriga et al., 1998). Cells are fractionated into cytosol and nuclear material. Nuclear P-TEFb is extracted by high salt. Western analysis is used to confirm that appropriate amounts of P-TEFb have been extracted as judged from the immunofluorescence results. Antibodies are used to immunoprecipitate P-TEFb and such material is assayed for CTD kinase activity (Marshall et al., 1996). The kinase activity is compared to the amount of Cdk9 as determined by western analysis of the immunoprecipitated material (Zhu et al., 1997). Such immunofluorescence studies may show that P-TEFb localization is tied to its function. Accordingly, CTD phosphorylation is analyzed using Western blots probed with antibodies that recognize specific phosphorylated states. H5 and H14 antibodies recognize Ser 2 and Ser 5 phosphorylation specifically and have been used to examine the bulk phosphorylation state of RNA polymerase II in vivo (Imamura et al., 2000).

Such methods are also applied to T cells (before and after activation) and adherent monocytes before and after differentiation into macrophages, determining what affect activation or differentiation has on the amount, location and activity of P-TEFb and what affect flavopiridol and HIV infection has on these parameters. Immunolocalization methods for macrophages and T cells are available (Khelef et al., 1998; McLaren et al., 1997; Lu and Partridge, 1998).

2. SCID-Hu Mouse Model for HIV

The effectiveness and lack of toxicity of flavopiridol is shown using the SCID-hu mouse system, an art-accepted model for preclinical studies of HIV (Mccune, 1997; Mccune, 1996). The SCID-hu model is constructed by co-implantation of human fetal thymus and liver under the kidney capsule of severe-combined immunodeficient (SCID) mice. Once implanted, the fetal tissues fuse, become vascularized, and grow into a unique "Thy/Liv" organ that is morphologically and functionally equivalent to a human thymus. The Thy/Liv implants generate a continuous source of human CD4+T cells for at least 6-12 months, and they support viral replication after inoculation of HIV-1 by direct injection. Thymocyte depletion occurs with most primary viral isolates within 3-5 wk and is manifest by both a loss of CD4+CD8+ immature cortical thymocytes and a decrease in the CD4/CD8 ratio in the thymic medulla.

Administration of antiretroviral agents to the mice results in dose-dependent inhibition of HIV-1 replication (and protection of CD4+ cells) within the implants, as assessed by measurement of viral core protein (p24) and viral RNA and by analysis of human thymocyte subpopulations by flow cytometry in treated versus untreated mice. This model is the NIAID standard for examining the effectiveness of potential anti-HIV drugs (Stoddart et al., 2000; Stoddart et al., 1998).

Groups of SCID-hu Thy/Liv are treated with flavopiridol at 1, 0.3, and 0.1 mg/kg/day by twice-daily intraperitoneal injection beginning 24 h before inoculation of 1,000 TCID50 of HIV-1 NL4-3 directly into the implant. These doses are about 10% lower than those that cause apoptosis of normal lymphoid cells (Arguello et al., 1998). Dosing continues daily until 12 days after inoculation, when the mice are euthanized and the implants collected for viral load and flow cytometric analyses. One group of mice is treated with 3TC (positive antiviral control), one group is untreated, and one group is neither infected nor treated. In addition, one group of uninfected mice is treated with flavopiridol at 1 mg/kg/day to assess the effects of treatment on thymocyte subpopulations in the absence of virus-mediated effects. Lack of toxicity is assessed by daily observation, weight change, and necropsy examination at the time of termination. The lowest effect concentration of flavopiridol is thus determined in such studies. In addition to the injection regimen, mice are treated by continuous subcutaneous infusion by Alzet pumps and oral dosing is used with the injection formulation, as in several animal models.

EXAMPLE 10

Administration of Flavopiridol

Results from several animal studies show that flavopiridol can be safely administered in amounts effective to produce anti-tumor effects. Given that anti-HIV effects are evident at lower doses, it is evident that doses effective to treat HIV can be readily achieved.

Studies conducted in animals implanted with the human cell lines HL-60 (promyelocytic leukemia) and SUDHL-4 (B-cell non-Hodgkin's lymphoma) showed significant sustained reduction in tumor masses, particularly when flavopiridol was administered as an IV bolus and/or IP for 5 consecutive days at a dose of 5 mg/kg/dose (Arguello et al., 1998). This regimen was well tolerated in these animals. Initial plasma samples from these animals demonstrated high plasma flavopiridol concentration (~6–8 $\mu$M) followed by a rapid decline in plasma levels. Immunohistochemistry studies of tumors obtained from treated animals compared with controls displayed significant apoptosis detected by immunostaining.

The antitumor effects of flavopiridol on HNSCC tumor xenografts were also determined. Subcutaneous tumors of HN12 cells (human tumor cells that harbor a mutated p53 protein) were established in athymic nu/nu mice within 12 days (7–9 mm in diameter) and then treated with flavopiridol. Upon completion, animals from the treated and control group were euthanized and tumor tissue analyzed, or the animals were monitored for body weight and tumor growth for a further 10 weeks.

The immediate effect of flavopiridol was noticeable by the end of the treatment period, at which time the treated group demonstrated a reduction in tumor growth by approximately 23%. This reduction was sustained, and by 10 weeks, these lesions were approximately 60% smaller than those from control animals ($p<0.05$). Analysis of the T/C (ratio of the changes in the median tumor size of treated and control animals) for each time point revealed that the optimal T/C was 26% (74% reduction; $p<0.001$; day 31). Drug toxicity was limited, as when assessed by weight loss, animals in the treated group demonstrated only a marginal reduction (<10%) during the treatment period and made full recovery within 3–4 days of completion.

Excised tumor tissues from both control and treated group were analyzed for apoptosis, using the TUNEL assay. Although increased apoptotic staining was observed as early as 2 days of flavopiridol treatment, the level of TUNEL staining was remarkably elevated upon completion of treatment. Together, these data suggest that flavopiridol has potent antitumor activity in vivo, possibly by inducing tumor cells to undergo apoptosis (Patel et al., 1998).

In parallel experiments, paraffin tumor tissues sections were analyzed for cyclin $D_1$, D3 and cyclin E, and expression of all three gene products was readily detected in the control tissue. In contrast, a significant reduction in levels of cyclin $D_1$ was observed in the treated tissue, whereas those of cyclin D3 and cyclin E were unaffected. Thus, expression of cyclin $D_1$ was reported to be specifically diminished in vivo in response to flavopiridol treatment (Patel et al., 1998).

Murine pharmacokinetic experiments using doses of 75, 50, 25, or 12.5 mmol/kg (32.9, 21.9, 11.0, or 5.5 mg/kg) were conducted by 0.5 minute IV infusion. Plasma concentration-time profiles exhibited biexponential behavior with harmonic mean half-lives of 16.4 and 201.0 minutes for the $\alpha$ and $\beta$ phases, respectively. The mean total body plasma clearance was 22.6 ml/min/kg. Peak plasma levels were proportional to the doses administered within this dose range. An IV dose of 100 mmol/kg (4–3.8 mg/kg), however, produced plasma levels in excess of that which would be projected from a linear relationship between dose and plasma concentration. Mice given this dose were moribund within one hour following injection.

Canine pharmacokinetics were studied in two dogs each given 4 mmol/kg (1.8 mg/kg) by one minute infusion. Plasma concentration-time profiles exhibited biexponential behavior with harmonic mean half-lives of 23.4 and 273.9 minutes for the $\alpha$ and $\beta$ phases, respectively. The mean total body plasma clearance was 10.4 ml/min/kg. Bolus IV doses of 25 and 8 mmol/kg (11.0 and 3.5 mg/kg) and 12 mmol/kg (5.3 mg/kg) given by 24 hr continuous IV infusion produced severe gastrointestinal symptoms, including vomiting, diarrhea and hemorrhage. Administration of 6 mmol/kg (2.6 mg/kg) by 24 hr continuous infusion IV was tolerated without significant evidence of toxicity as indicated by clinical signs, or routine hematology and clinical chemistry, except for a mild elevation of the serum alkaline phosphatase levels. Significantly, using this approach steady state plasma concentrations of approximately 0.3 mM (0.13 mg/ml) were achieved.

Fischer 344 male rats were administered 0, 0.5, 2, 4 and 8 mg/kg/day (0, 3, 12, 24, and 48 mg/m$^2$/day) of flavopiridol as a bolus intravenous injection in the lateral tail vein for 5 consecutive days. Daily doses of 8 mg/kg/day were lethal on days 2 through 8. All rats treated at 0, 0.5. 2. and 4 mg/kg/day survived to scheduled necropsy on days 8 and 29. Soft and loose stools were seen in most drug-treated rats with greater incidence and severity occurring in the 4 and 8 mg/kg/day groups. Mucous and liquid stools, as well as significant and steady weight loss, were also seen in the 8 mg/kg/day group. Rats in the 2 and 4 mg/kg/day groups showed limited (28%–37%) reductions in leukocyte counts on day 8 but recovery was complete by day 15. Pasted perineum (due to diarrhea) was seen at necropsy in the 8 mg/kg/day group.

Drug-related microscopic lesions were present in the bone marrow (myeloid cell hypoplasia), cecum (necrosis), epididymides (abnormal spermatids), mandibular lymph nodes (necrosis), mesenteric lymph nodes (lymphoid hypoplasia and infiltrating macrophages), spleen (lymphoid atrophy and absence of hematopoietic cell proliferation) and thymus (atrophy and lymphoid necrosis). These lesions occurred primarily in the 8 mg/kg/day group although one to two rats in the 4 mg/kg/day group showed minimal necrosis of the cecum wall, lymphoid hypoplasia and thymic atrophy. The TLD for flavopiridol given intravenously to male rats for five daily doses was between 4 mg/kg/day (24 mg/m$^2$/day). Bone marrow toxicity was considered to be dose-limiting.

Clinical trials in human patients have also been conducted, the results from which also show the safe administration of flavopiridol in amounts effective to produce anti-tumor effects.

A phase I trial of flavopiridol in patients with refractory malignancies was conducted, allowing the maximum-tolerated dose (MTD), toxicity profile and pharmacology of flavopiridol administration (72-hour infusion every 2 weeks) to be determined. Seventy-six patients with refractory malignancies with prior disease progression were treated with flavopiridol, with first-cycle pharmacokinetic sampling. In common with all six clinical trials reported on the NIH clinical trials web page (http://cancernet.nci.nih.gov/trialsrch.shtm), patients infected with the HIV virus were excluded from the trial.

Forty-nine patients defined the first MTD, 50 mg/m$^2$/d×3 with dose-limiting toxicity (DLT) of secretory diarrhea at 62.5 mg/kg/d×3. Subsequent patients received anti-diarrheal prophylaxis (ADP) to define a second MTD, 78 mg/m$^2$/d×3 with DLT of hypotension at 98 mg/m$^2$/d×3. Other toxicities included a proinflammatory syndrome with alterations in acute-phase reactants, particularly at doses >50 mg/m$^2$/d×3, which in some patients prevented chronic therapy every 2 weeks. In some patients, ADP was not successful, requiring dose de-escalation.

Although approximately 70% of patients displayed predictable flavopiridol pharmacology, unexpected interpatient variability and post-infusion peaks were observed in approximately 30% of cases. At the two MTDs, mean plasma flavopiridol concentrations of 271 nM (50 mg/m$^2$/d×3) and 344 nM (78 mg/m$^2$/d×3), respectively, were achieved.

Antitumor effects were observed in certain patients with renal, prostate, and colon cancer, and non-Hodgkin's lymphoma. Plasma concentrations of flavopiridol (200 to 400 nM) deduced to be necessary from studies in preclinical models were achieved safely. The MTD of infusional flavopiridol was found to be 50 mg/m$^2$/d×3 with dose-limiting secretory diarrhea at 62.5 mg/m$^2$/d×3. With ADP, 78 mg/m$^2$/d×3 was the MTD, with dose-limiting hypotension at 98 mg/m$^2$/d×3. Based on chronic tolerability, 50 mg/m$^2$/d×3 was the recommended phase II dose without ADP (Senderowicz et al., 1998).

Interpreting results from this Phase I infusional trial (Senderowicz et al., 1998) in the context of the present HIV treatment invention shows that, even at the lowest dose given to patients (4 mg/m$^2$/day over 72 hour continuous infusion), peak concentrations above those required to inhibit HIV transcription were reached: cmax: 17–40 nM. No side effects were observed until 18 mg/m$^2$/day (180–220 nM), which is well above the concentration required for HIV inhibition. Flavopiridol decreased lymphocytes in both the infusional and 1 hr infusion trial. However, in the infusional trial, significant drops in lymphocytes occurred at doses >or equal to 50 mg/m$^2$/day. This decline was acute, reversible and not associated with increased infection complications.

Although by no means a requirement of the invention, it is currently contemplated that exposure to, and preferably, chronic exposure to, a plasma concentration of about 30–60 nM, more preferably about 30 nM, of flavopiridol would effectively suppress HIV. Any route of administration that results in such plasma levels can be used in conjunction with the present invention.

In considering the active plasma concentration of flavopiridol, as with any drug, the most pertinent value is the concentration of "free drug". The present inventors contemplate that up to about 80% of flavopiridol could bind to plasma proteins, meaning that about 20% of total flavopiridol is in the unbound, "free" form. However, such phenomena are routinely encountered by physicians and can be readily factored into the dosing regimens for any individual or group of patients, particularly in light of the clinical data available from cancer treatment and the comparative studies presented herein.

Studies in human xenograft leukemia/lymphoma models and in patients with head and neck neoplasms established that apoptotic responses were observed only when flavopiridol was administered in a bolus fashion (Patel et al., 1998; Arguello et al., 1998). These apoptotic responses were associated with peak plasma concentrations of 5–8 $\mu$M (Arguello et al., 1998), which micromolar concentrations were only observed in preclinical models when flavopiridol was used in a bolus administration. Studies comparing infusional versus bolus administration in animals demonstrated that the AUC observed in both schedules were similar, allowing the conclusion that the apoptotic responses observed in these apoptosis-sensitive models were associated with peak flavopiridol plasma concentration ~5–8 $\mu$M. Furthermore, the partial response observed in the infusional clinical trial occurred at the highest dose level administered to humans (122.5 mg/m$^2$/day), achieving a peak plasma concentration of about 10 $\mu$g (Senderowicz et al., 1998).

In light of the success of the bolus flavopiridol administration in preclinical models, another Phase I trial was commenced using a 1 hour infusion of flavopiridol every day for 5 consecutive days (QDx5 schedule) every 3 weeks. Again, patients infected with HIV were excluded from the trial. Twenty-seven patients were treated in this phase I trial. The maximal tolerated dose (recommended Phase II dose) was 37.5 mg/m$^2$/day for 5 consecutive days. Dose limiting toxicities observed at 53 mg/m$^2$/day were nausea/vomiting, neutropenia, lymphocytopenia, fatigue and diarrhea. Other (non-dose limiting) side effects were 'local tumor pain' and anorexia.

In this Phase I bolus trial, a mean flavopiridol peak plasma concentration of about 2 $\mu$M was obtained at the MTD (37.5 mg/m$^2$/day QDx5). Moreover, patients at the QDx3 (50 mg/m$^2$/day) schedule reached approximately 4 $\mu$M. However, the QDx5 schedule achieved higher AUCs and was more tolerable.

Thus, appropriate flavopiridol doses for Phase II clinical trials administered as 1 hour infusion for the treatment of cancer have been defined as 37.5 mg/m$^2$/day IV bolus for 5 consecutive days, administered every 3 weeks (total dose: 187.5 mg/m$^2$). Patients infected with the HIV virus have been excluded from such trials. However, given the connection between low dose flavopiridol and inhibition of HIV made possible by the present invention, and based on good tolerability of flavopiridol in patients with cancer treated with both schedules, the deliberate treatment of HIV patients can now be conducted.

Although unexpected, any side-effects can be routinely managed using techniques commonly known to physicians. Nausea/vomiting can be controlled by a combination of granisetron before each course and metoclopramide for the rest of the cycle. Hypotension can be reversed promptly with IV fluids and standard treatments for hypotension. Naturally, where other agents are used to manage any side-effects, the agents will be selected so that they do not significantly impair the effectiveness of flavopiridol itself. Naturally, agents that impair the activity of flavopiridol will be avoided, as will agents that impair bioavailability, such as those that block absorption of oral flavopiridol, increase excretion or clearance of flavopiridol and such like. Applying these types of considerations is a routine aspect of clinical treatment that can practiced as part of the present invention in light of the present disclosure.

There is no reason why flavopiridol treatment for HIV and AIDS could not utilize the type of doses reported in the foregoing anti-cancer studies, namely, infusional flavopiridol of 50 mg/m$^2$/d×3; infusional flavopiridol with ADP of 78 mg/m$^2$/d×3, both schedules, every 2 weeks; and 1 hour infusion flavopiridol of 37.5 mg/m$^2$/day IV for 5 days every 3 weeks. However, it is a distinct advantage of this invention, due to both P-TEFb being a preferred target and the uncompetitive nature of inhibition, that the doses of flavopiridol for HIV treatment can be reduced, and even markedly reduced, in comparison to those used for cancer treatment.

Accordingly, flavopiridol doses of about 4 mg/m$^2$/day (over 72 hour continuous infusion) would yield therapeutically effective levels of flavopiridol in HIV and AIDS patients. Rate-controlled administration devices, rapidly flowing IV and central venous catheters are appropriate for such administration, although a variety of effective administration means are available, any one or more of which may be used in conjunction with the present invention. Those of ordinary skill in the art will thus be able to routinely vary both the dose and administration schedule, once weekly, for example, without undue experimentation in light of the present disclosure.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary technical, procedural or other details supplementary to those set forth herein, are specifically incorporated herein by reference without disclaimer.

Abergel, Moulard, Moreau, Loret, Cambillau, Fontecilla-Camps, "Systematic use of the incomplete factorial approach in the design of protein crystallization studies," *J Biol. Chem.*, 266:20131–20138, 1991.

Archambault, Pan, Dahmus, Cartier, Marshall, Zhang, Dahmus, Greenblatt, "FCP1, the RAP74-interacting subunit of a human protein phosphatase that dephosphorylates the carboxyl-terminal domain of RNA polymerase 110," *J. Biol. Chem.*, 273:27593–27601, 1998.

Arguello, Alexander, Sterry, Tudor, Smith, Kalavar, Greene, Koss, Morgan, Stinson, Siford, Alvord, Klabansky, Sausville, "Flavopiridol induces apoptosis of normal lymphoid cells, causes immunosuppression, and has potent antitumor activity In vivo against human leukemia and lymphoma xenografts," *Blood*, 91:2482–2490, 1998.

Bellizzi, Widom, Kemp, Clardy, "Producing selenomethionine-labeled proteins with a baculovirus expression vector system," *Structure. Fold. Des.*, 7:R263–R267, 1999.

Bentley, "Regulation of transcriptional elongation by RNA polymerase II," *Curr. Opin. Genet. Dev.*, 5:210–216, 1995.

Bentley, "Coupling RNA polymerase II transcription with pre-mRNA processing," *Curr. Opin. Cell Biol.*, 11:347–351, 1999.

Bieniasz, Grdina, Bogerd, Cullen, "Recruitment of a protein complex containing Tat and cyclin T1 to TAR governs the species specificity of HIV-1 Tat," *EMBO J*, 17:7056–7065, 1998.

Bieniasz, Grdina, Bogerd, Cullen, "Analysis of the effect of natural sequence variation in Tat and in cyclin T on the formation and RNA binding properties of Tat-cyclin T complexes," *J. Virol.*, 73:5777–5786, 1999a.

Bieniasz, Grdina, Bogerd, Cullen, "Highly divergent lentiviral Tat proteins activate viral gene expression by a common mechanism," *Mol. Cell Biol.*, 19:4592–4599, 1999b.

Bieniasz, Grdina, Bogerd, Cullen, "Recruitment of cyclin T1/P-TEFb to an HIV type 1 long terminal repeat promoter proximal RNA target is both necessary and sufficient for full activation of transcription," *Proc. Natl. Acad Sci. USA.*, 96:7791–7796, 1999c.

Blau, Xiao, McCracken, O'Hare, Greenblatt, Bentley, "Three functional classes of transcriptional activation domains," *Mol. Cell Biol.*, 16:2044–2055, 1996.

Boyd, Simpson, Cann, Johnson, Weiss, "A single amino acid substitution in the V1 loop of human immunodeficiency virus type 1 gp120 alters cellular tropism," *J Virol.*, 67:3649–3652, 1993.

Byrd, et al., *Blood*, 92:3804, 1998.

Carlson, Dubay, Sausville, Brizuela, Worland, "Flavopiridol induces G1 arrest with inhibition of cyclin-dependent kinase (CDK) 2 and CDK4 in human breast carcinoma cells," *Cancer Res.*, 56:2973–2978, 1996.

Carlson, Lahusen, Singh, Loaiza-Perez, Worland, Pestell, Albanese, Sausville, Senderowicz, "Down-regulation of cyclin D$_1$ by transcriptional repression in MCF-7 human breast carcinoma cells induced by flavopiridol," *Cancer Res.*, 59:4634–4641, 1999.

Carrington, Dean, Martin, O'Brien, "Genetics of HIV-1 infection: chemokine receptor CCR5 polymorphism and its consequences," *Hum. Mol. Genet.*, 8:1939–1945, 1999.

Carroll, Peterlin, Derse, "Inhibition of human immunodeficiency virus type I Tat activity by coexpression of heterologous trans activators," *J. Virol.*, 66:2000–2007, 1992.

Chao, Fujinaga, Marion, Taube, Sausville, Senderowicz, Peterlin, Price, "Flavopiridol inhibits P-TEFb and blocks HIV-1 replication," *J. Biol. Chem.*, 275:28345–28348, 2000.

Chayen, Boggon, Cassetta, Deacon, Gleichmann, Habash, Harrop, Helliwell, Nieh, Peterson, Raftery, Snell, Hadener, Niemann, Siddons, Stojanoff, Thompson, Ursby, Wulff, "Trends and challenges in experimental macromolecular crystallography," *Q. Rev. Biophys.*, 29:227–278, 1996.

Chen and Zhou, "Tat activates human immunodeficiency virus type 1 transcriptional elongation independent of TFIIH kinase," *Mol. Cell Biol.*, 19:2863–2871, 1999.

Cho, Kim, Mancebo, Lane, Flores, Reinberg, "A protein phosphatase functions to recycle RNA polymerase II," *Genes Dev.*, 13:1540–1552, 1999.

Chodosh, Fire, Samuels, Sharp, "5,6-Dichloro-1-beta-D-ribofuranosylbenzimidazole inhibits transcription elongation by RNA polymerase II in vitro," *J. Biol. Chem.*, 264:2250–2257, 1989.

Chun and Jeang, "Requirements for RNA polymerase II carboxyl-terminal domain for transcription of human retroviruses, human T-cell lymphotrophic virus, and HIV-1," *J. Biol. Chem.*, 271:27888–27894, 1996.

Cleland, *Methods Enzymol.*, 63:103–138, 1979.

Collart, Tourkine, Belin, Vassalli, Jeanteur, Blanchard, "c-fos Gene transcription in murine macrophages is modulated by a calcium-dependent block to elongation in intron 1," *Mol. Cell. Biol.,* 11:2826–2831, 1991.

Cujec, Okamoto, Fujinaga, Meyer, Chamberlin, Morgan, Peterlin, "The HIV transactivator Tat binds to the cdk-activating kinase and activates the phosphorylation of the carboxy-terminal domain of RNA polymerase II," *Genes Dev.,* 11:2645–2657, 1997.

Dahmus, "Phosphorylation of mammalian RNA polymerase II," *Methods in Enzymology,* 273:185–193, 1996.

De Azevedo, Mueller-Dieckmann, Schulze-Gahrnen, et al., "Structural Basis for Specificity and Potency of a Flavonoid Inhibitor of Human CDK2, A Cell Cycle Kinase," *Proc. Natl. Acad. Sci. USA,* 93:2735–40, 1996.

Dixon and Webb, Enzymes $3^{RD}$ Edition, Academic Press, New York, 2000.

Edwards, Wong, Elledge, "Human cyclin K, a novel RNA polymerase II-associated cyclin possessing both carboxy-terminal domain kinase and Cdk-activating kinase activity," *Mol. Cell Biol.,* 18:4291–4300, 1998.

Egyhazi, Ossoinak, Pigon, Holmgren, Lee, Greenleaf, "Phosphorylation dependence of the initiation of productive transcription of Balbiani ring 2 genes in living cells," *Chromosoma,* 104:422–433, 1996.

Fackler, et al., *Eur. J. Biochem.,* 247:843–851, 1997.

Finzi and Silliciano, "Viral dynamics in HIV-1 infection," *Cell,* 93:665–671, 1998.

Flores, Lee, Kessler, Miller, Schlief, Tomassini, Hazuda, "Host-cell positive transcription elongation factor b kinase activity is essential and limiting for HIV type 1 replication," *Proc. Natl. Acad. Sci. USA,* 96:7208–7213, 1999.

Fu, Peng, Price, Flores, "Cyclin K functions as a Cdk9 regulatory subunit and participates in RNA polymerase II transcription," *J. Biol. Chem.,* 274:34527–34530, 1999.

Fujinaga, Cujec, Peng, Garriga, Price, Grana, Peterlin, "The ability of positive transcription elongation factor B to transactivate human immunodeficiency virus transcription depends on a functional kinase domain, cyclin T1, and Tat," *J. Viro.,* 72:7154–7159, 1998.

Gane and Dean, "Recent advances in structure-based rational drug design," *Curr. Opin. Struct. Biol.,* 10:401–404, 2000.

Garber and Jones, "HIV-1 Tat: coping with negative elongation factors," *Curr. Opin. Immunol.,* 11:460–465, 1999.

Garber, Wei, Jones, "HIV-1 Tat interacts with cyclin T1 to direct the P-TEFb CTD kinase complex to TAR RNA," *Cold Spring Harb. Symp. Quant. Biol.,* 63:371–380, 1998a.

Garber, Wei, KewalRamani, Mayall, Herrmann, Rice, Littman, Jones, "The interaction between HIV-1 Tat and human cyclin T1 requires zinc and a critical cysteine residue that is not conserved in the murine CycT1 protein," Genes Dev., 12:3512–3527, 1998b.

Garber, Mayall, Suess, Meisenhelder, Thompson, Jones, "CDK9 autophosphorylation regulates high-affinity binding of the human immunodeficiency virus type 1 tat-P-TEFb complex to TAR RNA," *Mol. Cell Biol.,* 20:6958–6969, 2000.

Garcia-Martinez, Mavankal, Neveu, Lane, Ivanov, Gaynor, "Purification of a Tat-associated kinase reveals a TFIIH complex that modulates HIV-1 transcription," *EMBO J.,* 16:2836–2850, 1997.

Garriga, Mayol, Grana, "The CDC2-related kinase PITALRE is the catalytic subunit of active multimeric protein complexes," *Biochemical Journal,* 319:293–298, 1996a.

Garriga, Segura, Mayol, Grubmeyer, Grana, "Phosphorylation site specificity of the CDC2-related kinase PITALRE," *Biochemical Journal,* 320:983–989, 1996b.

Garriga, Peng, Parreno, Price, Henderson, Grana, "Upregulation of cyclin T1/CDK9 complexes during T cell activation," *Oncogene,* 17:3093–3102, 1998.

Gold and Rice, "Targeting of CDK8 to a promoter-proximal RNA element demonstrates catalysis-dependent activation of gene expression," *Nucleic Acids Res.,* 26:3784–3788, 1998a.

Gold, Yang, Herrmann, Rice, "PITALRE, the catalytic subunit of TAK, is required for human immunodeficiency virus Tat transactivation in vivo," *J. Virol.,* 72:4448–4453, 1998b.

Grana, De Luca, Sang, Fu, Claudio, Rosenblatt, Morgan, Giordano, "PITALRE, a nuclear CDC2-related protein kinase that phosphorylates the retinoblastoma protein in vitro," *Proc. Natl. Acad. Sci. U.S.A.,* 91:3834–3838, 1994.

Grana and Reddy, "Cell Cycle Control in Mammalian Cells: Role of Cyclins, Cyclin Dependent Kinases (CDKs), Growth Suppressor Genes and Cyclin-Dependent Kinase Inhibitors (CKIs)," *Oncogene,* 11:211–9, 1995.

Gray, Wodicka, Thunnissen, Norman, Kwon, Espinoza, Morgan, Barnes, LeClerc, Meijer, Kim, Lockhart, Schultz, "Exploiting chemical libraries, structure, and genomics in the search for kinase inhibitors," *Science,* 281:533–538, 1998.

Gray, Detivaud, Doerig and Meijer, "ATP-Site Directed Inhibitors of Cyclin-Dependent Kinases," *Curr. Med. Chem.,* 6:859–75, 1999.

Guo and Price, "Mechanism of DmS-II-mediated pause suppression by Drosophila RNA polymerase II," *J. Biol. Chem.,* 268:18762–18770, 1993.

Herrmann and Rice, "Specific interaction of the human immunodeficiency virus Tat proteins with a cellular protein kinase," *Virology,* 197:601–608, 1993.

Herrmann and Rice, "Lentivirus Tat proteins specifically associate with a cellular protein kinase, TAK, that hyperphosphorylates the carboxyl-terminal domain of the large subunit of RNA polymerase II: candidate for a Tat cofactor," *J. Virol.,* 69:1612–1620, 1995.

Herrmann, Carroll, Wei, Jones, Rice, "Tat-associated kinase, TAK, activity is regulated by distinct mechanisms in peripheral blood lymphocytes and promonocytic cell lines," *J. Virol.,* 72:9881–9888, 1998.

Ho and Shuman, "Distinct roles for CTD Ser-2 and Ser-5 phosphorylation in the recruitment and allosteric activation of mammalian mRNA capping enzyme," *Molecular Cell,* 3:405–411, 1999.

Holstege, Jennings, Wyrick, Lee, Hengartner, Green, Golub, Lander, Young, "Dissecting the regulatory circuitry of a eukaryotic genome," *Cell,* 95:717–728, 1998.

Imamura, Koga, Uriu, Otagiri, Satoh, Hara, "Catalytic properties for naphthoquinones and partial primary structure of rabbit heart acetohexamide reductase," *Biol. Pharm. Bull.,* 23:155–158, 2000.

Ingelman, Ramaswamy, Niviere, Fontecave, Eklund, "Crystal structure of NAD(P)H:flavin oxidoreductase from *Escherichia coli,*" *Biochemistry,* 38:7040–7049, 1999.

Isel and Karn, "Direct evidence that HIV-1 Tat stimulates RNA polymerase II carboxyl-terminal domain hyperphosphorylation during transcriptional elongation," *J. Mol. Biol.,* 290:929–941, 1999.

Kanazawa, Okamoto, Peterlin, "Tat competes with CIITA for the binding to P-TEFb and blocks the expression of MHC class II genes in HIV infection," *Immunity (In Press),* 1999.

Kao, Calman, Luciw, Peterlin, "Antitermination of transcription within the long terminal repeat of HIV by the tat gene product," *Nature,* 330:489–493, 1987.

Karn, "Tackling Tat," *J. Mol. Biol.,* 293:235–254, 1999.

Kauppi, Lee, Carredano, Parales, Gibson, Eklund, Ramaswamy, "Structure of an aromatic-ring-hydroxylating dioxygenase-naphthalene 1,2-dioxygenase," *Structure,* 6:571–586, 1998.

Kaur, Stetler-Stevenson, Sebers, et al., "Growth Inhibition with Reversible Cell Cycle Arrest of Carcinoma Cells by Flavone L86-8275," *J. Natl. Cancer. Inst.,* 84:1736–40, 1992.

Keen, Churcher, Karn, "Transfer of Tat and release of TAR RNA during the activation of the human immunodeficiency virus type-I transcription elongation complex," *EMBO J.,* 16:5260–5272, 1997.

Kephart, Marshall, Price, "Stability of Drosophila RNA polymerase II elongation complexes in vitro," *Mol. Cell. Biol.,* 12:2067–2077, 1992.

Kephart, Price, Burton, Finkelstein, Greenblatt, Price, "Cloning of a Drosophila cDNA with sequence similarity to human transcription factor RAP74," *Nucleic Acids Res.,* 21:1319, 1993.

Khelef, Buton, Beatini, Wang, Meiner, Chang, Farese Jr., Maxfield, Tabas, "Immunolocalization of acyl-coenzyme A:cholesterol O-acyltransferase in macrophages," *J. Biol. Chem.,* 273:11218–11224, 1998.

Kim, Schulze-Gahmen, Brandsen, de Azevedo, "Structural basis for chemical inhibition of CDK2," *Prog. Cell Cycle Res.,* 2:137–145, 1996.

Kimura, Tao, Roeder, Cook, "Quantitation of RNA polymerase II and its transcription factors in an HeLa cell: little soluble holoenzyme but significant amounts of polymerases attached to the nuclear substructure," *Mol. Cell Biol.,* 19:5383–5392, 1999.

Landau and Rosenbusch, "Lipidic cubic phases: a novel concept for the crystallization of membrane proteins," *Proc. Natl. Acad. Sci. USA,* 93:14532–14535, 1996.

Laspia, Wendel, Mathews, "HIV-1 Tat overcomes inefficient transcriptional elongation in vitro, " *J. Mol. Biol.,* 232:732–746, 1993.

Lee and Greenleaf, "Modulation of RNA polymerase II elongation efficiency by C-terminal heptapeptide repeat domain kinase I," *J. Biol. Chem.,* 272:10990–10993, 1997.

Li, Bhuiyan, Alhasan, Senderowicz, Sarkar, *Clin. Cancer Res.,* 6(1):223–229, 2000.

Lis, Mason, Peng, Price, and Werner, "P-TEFb kinase recruitment and function at heat shock loci," *Genes Dev.,* 14:792–803, 2000.

Liu, Xie, Price, "A human RNA polymerase II transcription termination factor is a SWI2/SNF2 family member," *J. Biol. Chem.,* 273:25541–25544, 1998.

Losiewicz, Carlson, Kaur, Sausville, Worland, "Potent inhibition of CDC2 kinase activity by the flavonoid L86-8275," *Biochem. Biophys. Res. Commun.,* 201:589–595, 1994.

Lu and Partridge, "A new blocking method for application of murine monoclonal antibody to mouse tissue sections," *J. Histochem. Cytochem.,* 46:977–984, 1998.

Luecke, Schobert, Richter, Cartailler, Lanyi, "Structure of bacteriorhodopsin at 1.55 A resolution," *J. Mol. Biol.,* 291:899–911, 1999.

Madore and Cullen, "Genetic analysis of the cofactor requirement for human immunodeficiency virus type 1 Tat function," *J. Virol.,* 67:3703–3711, 1993.

Majello, Napolitano, Lania, "Recruitment of the TATA-binding protein to the HIV-1 promoter is a limiting step for Tat transactivation," *AIDS,* 12:1957–1964, 1998.

Majello, Napolitano, Giordano, Lania, Cdk, Cyclin, "Transcriptional regulation by targeted recruitment of cyclin-dependent CDK9 kinase in vivo," *Oncogene,* 18:4598–4605, 1999.

Mancebo, Lee, Flygare, Tomassini, Luu, Zhu, Peng, Blau, Hazuda, Price, Flores, "P-TEFb kinase is required for HIV Tat transcriptional activation in vivo and in vitro," *Genes Dev.,* 11:2633–2644, 1997.

Marciniak and Sharp, "HIV-1 Tat protein promotes formation of more-processive elongation complexes," *EMBO J.,* 10:4189–4196, 1991.

Marshall and Price, "Control of formation of two distinct classes of RNA polymerase II elongation complexes," *Mol. Cell. Biol.,* 12:2078–2090, 1992.

Marshall and Price, "Purification of P-TEFb, a transcription factor required for the transition into productive elongation," *J. Biol. Chem.,* 270:12335–12338, 1995.

Marshall, Peng, Xie, Price, "Control of RNA polymerase II elongation potential by a novel carboxyl-terminal domain kinase," *J. Biol. Chem.,* 271:27176–27183, 1996.

Marshall, Dahmus, Dahmus, "Regulation of carboxyl-terminal domain phosphatase by HIV-1 Tat protein," *J. Biol. Chem.,* 273:31726–31730, 1998.

Marshall, Guo, Price, "Drosophila RNA polymerase II elongation factor DmS-I1 has homology to mouse S-II and sequence similarity to yeast PPR2," *Nucleic Acids Res.,* 18:6293–6298, 1990.

Marzluff, "Preparation of active nuclei," *Methods Enzymol.,* 181:30–36, 1990.

Maury, "Monocyte maturation controls expression of equine infectious anemia virus," *J. Virol.,* 68:6270–6279, 1994.

Maury, "Regulation of equine infectious anemia virus expression," *J. Biomed. Sci.,* 5:11–23, 1998.

Maury, Oaks, Bradley, "Equine endothelial cells support productive infection of equine infectious anemia virus,"*J. Virol,* 72:9291–9297, 1998.

McCune, "Development and applications of the SCID-hu mouse model," *Semin. Immunol.,* 8:187–196, 1996.

McCune, "Animal models of HIV-1 disease," *Science,* 278:2141–2142, 1997.

McLaren, Prentice, Charnock-Jones, Sharkey, Smith, "Immunolocalization of the apoptosis regulating proteins Bcl-2 and Bax in human endometrium and isolated peritoneal fluid macrophages in endometriosis," *Hum. Reprod.,* 12:146–152, 1997.

Miller, Asselin, Dufort, Yang, Gupta, Marcu, Nepveu, "A cis-acting element in the promoter region of the murine c-myc gene is necessary for transcriptional block," *Mol. Cell Biol.,* 9:5340–5349, 1989.

Minvielle-Sebastia, L. and W. Keller, "mRNA polyadenylation and its coupling to other RNA processing reactions and to transcription," *Curr. Opin. Cell Biol.,* 11:352–357, 1999.

Morgan, "Principles of CDK Regulation," *Nature,* 374:131–4, 1995.

Morgan, "Cyclin-Dependent Kinases: Engines, Clocks, and Microprocessors," *Annu. Rev. Cell Dev. Biol.,* 13:261–91, 1997.

Napolitano, Licciardo, Gallo, Majello, Giordano, Lania, "The CDK9-associated cyclins T1 and T2 exert opposite effects on HIV-1 Tat activity," *AIDS,* 13:1453–1459, 1999.

Parada and Roeder, "Enhanced processivity of RNA polymerase II triggered by Tat-induced phosphorylation of its carboxy-terminal domain," *Nature,* 384:375–378, 1996.

Parker, Nieves-Neira, et al., "Early Induction of Apoptosis in Hematopoietic Cell Lines After Exposure to Flavopiridol," *Blood,* (91):458–465, 1998.

Patel, Senderowicz, Pinto, et al., "Flavopiridol, a Novel Cyclin-Dependent Kinase Inhibitor, Suppresses the Growth of Head and Neck Squamous Cell Carcinomas by Inducing Apoptosis," *J. Clin. Invest.,* 102:1674–1681, 1998.

Pendergrast and Hernandez, "RNA-targeted activators, but not DNA-targeted activators, repress the synthesis of short transcripts at the human immunodeficiency virus type 1 long terminal repeat," *J. Virol.,* 71:910–917, 1997.

Peng, Liu, Marion, Zhu, Price, "RNA polymerase II elongation control," *Cold Spring Harbor Symp. Quant. Biol.,* 63:365–370, 1998a.

Peng, Marshall, Price, "Identification of a cyclin subunit required for the function of Drosophila P-TEFb," *J. Biol. Chem.,* 273:13855–13860, 1998b.

Peng, Zhu, Milton, Price, "Identification of multiple cyclin subunits of human P-TEFb," *Genes Dev.,* 12:755–762, 1998c.

Pines, "The Cell Cycle Kinases," *Semin. Cancer Biol.,* 5:305–13, 1994.

Ping and Rana, "Tat-associated kinase (P-TEFb): a component of transcription preinitiation and elongation complexes," *J. Biol. Chem.,* 274:7399–7404, 1999.

Price, "P-TEFb, a cyclin-dependent kinase controlling elongation by RNA polymerase II," *Mol. Cell Biol.,* 20:2629–2634, 2000.

Price, Sluder, Greenleaf, "Dynamic interaction between a Drosophila transcription factor and RNA polymerase II," *Mol. Cell Biol.,* 9:1465–1475, 1989.

Rana and Jeang, "Biochemical and functional interactions between HIV-1 Tat protein and TAR RNA," *Arch. Biochem. Biophys.,* 365:175–185, 1999.

Reines, Conaway, Conaway, "The RNA polymerase II general elongation factors," *Trends. Biochem. Sci.,* 21:351–355, 1996.

Reines, Conaway, Conaway, "Mechanism and regulation of transcriptional elongation by RNA polymerase II," *Curr. Opin. Cell Biol.,* 11:342–346, 1999.

Roda Husman and Schuitemaker, "Chemokine receptors and the clinical course of HIV-1 infection," *Trends Microbiol.,* 6:244–249, 1998.

Ross, Bieniasz, Cullen, "Role of chemokine receptors in HIV-1 infection and pathogenesis," *Adv. Virus Res.,* 52:233–267, 1999.

Schrump, Matthews, Chen, Mixon, Altorki, *Clin. Cancer Res.,* 4:2885, 1998.

Schwartz, Farsi, Maslak, Kelsen, Spriggs, *Clin. Cancer Res.,* 3:1467, 1997.

Sedlacek, Czech, Naik, Kaur, Worland, Losiewicz, Parker, Carlson, Smith, Senderowicz and Sausville, "Flavopiridol (L86-8275, NSC-649890), A New Kinase Inhibitor for Tumor Therapy," *International Journal of Oncology,* 9:1143–1168, 1996.

Sehgal, Darnell, Tamm, "The inhibition by DRB (5,6,-dichloro-1-B-D-ribofuranosylbenzimidazole) of hnRNA and mRNA production in HeLa cells," *Cell,* 9:473–480, 1976.

Senderowicz and Sausville, "Preclinical and clinical development of cyclin-dependent kinase modulators," *J. Natl. Cancer Inst.,* 92:376–387, 2000.

Senderowicz and Sausville, *J. Natl. Cancer Inst.,* 92(5):6–17, 2000.

Senderowicz, Carlson, Worland, et al., "Decreased Transcription of Cyclin $D_1$ Induced by a Cyclin Dependent Kinase Inhibitor, Flavopiridol," *In Proc. Eighty-Eightieth Annual Meeting of the American Association of Cancer Research. San Diego, Calif.,* 1997.

Senderowicz, Headlee, Stinson, Lush, Kalil, Villalba, Hill, Steinberg, Figg, Tompkins, Arbuck, Sausville, "Phase I trial of continuous infusion flavopiridol, a novel cyclin-dependent kinase inhibitor, in patients with refractory neoplasms," *J. Clin. Oncol.,* 16:2986–2999, 1998.

Shapiro, Koestner, Matranga, Rollins, *Clin. Cancer Res.,* 5:2925, 1999.

Shilatifard, "Factors regulating the transcriptional elongation activity of RNA polymerase II [Review]," *FASEB J.,* 12:1437–1446, 1998a.

Shilatifard, "The RNA polymerase II general elongation complex. Biological Chemistry 379, 27–31, 1998b.

Singh, Sausville and Senderowicz, "Cyclin D1 and Cdk6 are the Targets for Flavopiridol-Mediated G1 Block in MCF10A Breast Epithelial Cell Line," *Proceedings of the American Association for Cancer Research Annual Meeting,* 40:28, 1999.

Sluder, Greenleaf, Price, "Properties of a Drosophila RNA polymerase II elongation factor," *J Biol., Chem.,* 264:8963–8969, 1989.

Stoddart, Rabin, Hincenbergs, Moreno, Linquist-Stepps, Leeds, Truong, Wyatt, Ecker, McCune, "Inhibition of human immunodeficiency virus type 1 infection in SCID-hu Thy/Liv mice by the G-quartet-forming oligonucleotide, ISIS 5320," *Antimicrob. Agents Chemother.,* 42:2113–2115, 1998.

Stoddart, Moreno, Linquist-Stepps, Bare, Bogan, Gobbi, Buckheit Jr., Bedard, Rando, McCune, "Antiviral activity of 2'-deoxy-3'-oxa-4'-thiocytidine (BCH-10652) against lamivudine-resistant human immunodeficiency virus type 1 in SCID-hu Thy/Liv mice," *Antimicrob. Agents Chemother.,* 44:783–786, 2000.

Tamm, Kikuchi, Darnell, Salditt-Georgeieff, "Short capped hnRNA precursor chains in HeLa cells: continued synthesis in the presence of 5,6-dichloro-1-B-D-ribofuranosylbenzimidazole," *Biochemistry,* 19:2743–2748, 1980.

Taube, Fujinaga, Irwin, Wimmer, Geyer, Peterlin, "Interactions between equine cyclin T1, Tat and TAR are disrupted by a leucine to valine substitution found in human cyclin T1," *J. Virol.,* 74:892–898, 1999a.

Taube, Fujinaga, Wimmer, Barboric, Peterlin, "Tat transactivation: A model for the regulation of eukaryotic transcriptional elongation," *Virology,* 264:245–253, 1999b.

Toohey and Jones, "In vitro formation of short RNA polymerase II transcripts that terminate within the HIV-1 and HIV-2 promoter-proximal downstream regions," *Genes Dev.,* 3:265–282, 1989.

Wada, Takagi, Yamaguchi, Ferdous, Imai, Hirose, Sugimoto, Yano, Hartzog, Winston, Buratowski, Handa, "DSIF, a novel transcription elongation factor that regulates RNA polymerase II processivity, is composed of human Spt4 and Spt5 homologs," *Genes Dev.,* 12:343–356, 1998a.

Wada, Takagi, Yamaguchi, Watanabe, Handa, "Evidence that P-TEFb alleviates the negative effect of DSIF on RNA polymerase II-dependent transcription in vitro," *EMBO J.,* 17:7395–7403, 1998b.

Wei, Garber, Fang, Fischer, Jones, "A novel CDK9-associated C-type cyclin interacts directly with HIV-1 Tat and mediates its high-affinity, loop-specific binding to TAR RNA," *Cell,* 92:451–462, 1998.

Wen and Shatkin, "Transcription elongation factor hSPT5 stimulates mRNA capping," *Genes Dev.,* 13:1774–1779, 1999.

Wimmer, Fujinaga, Taube, Cujec, Zhu, Peng, Price, Peterlin, "Interactions between Tat and TAR and human immunodeficiency virus replication are facilitated by human cyclin T1 but not cyclins T2a or T2b," *Virology,* 255:182–189, 1999.

Worland, Kaur, Stetler-Stevenson, et al., "Alteration of the Phosphorylation State of p34cdc2 Kinase by the Flavone L86-8275 in Breast Carcinoma Cells. Correlation with Decreased HI Kinase Activity," *Biochem. Pharmacol.*, 46:1831–40, 1993.

Wu-Baer, Lane, Gaynor, "Role of the human homolog of the yeast transcription factor SPT5 in HIV-1 Tat-activation," *J. Mol. Biol.*, 277:179–197, 1998.

Xie and Price, "Purification of an RNA polymerase II transcript release factor from Drosophila," *J. Biol. Chem.*, 271:11043–11046, 1996.

Xie and Price, "Drosophila factor 2, an RNA polymerase II transcript release factor, has DNA-dependent ATPase activity," *J. Biol. Chem.*, 272:31902–31907, 1997.

Yamaguchi, Takagi, Wada, Yano, Furuya, Sugimoto, Hasegawa, Handa, "NELF, a multisubunit complex containing RD, cooperates with DSIF to repress RNA polymerase II elongation," *Cell*, 97:41–51, 1999a.

Yamaguchi, Wada, Watanabe, Takagi, Hasegawa, Handa, "Structure and function of the human transcription elongation factor DSIF," *J. Biol. Chem.*, 274:8085–8092, 1999b.

Yang, Gold, Tang, Lewis, Aguilarcordova, Rice, Herrmann, "TAK, an HIV TAT-associated kinase, is a member of the cyclin-dependent family of protein kinases and is induced by activation of peripheral blood lymphocytes and differentiation of promonocytic cell lines," *Proc. Natl. Acad. Sci. U.S.A.*, 94:12331–12336, 1997.

Yankulov and Bentley, "Transcriptional control: Tat cofactors and transcriptional elongation," *Current Biology*, 8:R447–R449, 1998.

Yao and Browning, "Potential Use of Flavopiridol to Treat HHV-8-Associated Malignancies," *Blood*, 92 (10 Suppl. I Part 1–2):539A, 1998.

Zandomeni, Mittleman, Bunick, Ackerman, Weinmann, "Mechanism of action of dichloro-beta-D-ribofuranosylbensimidazole: Effect on in vitro transcription," *Proc. Natl. Acad. Sci. U.S.A.*, 79:3167–3170, 1982.

Zawel, Kumar, Reinberg, "Recycling of the general transcription factors during RNA polymerase II transcription," *Genes Dev.*, 9:1479–1490, 1995.

Zhou, Chen, Pierstorff, Luo, "Transcription elongation factor P-TEFb mediates Tat activation of HIV-1 transcription at multiple stages," *EMBO J.*, 17:3681–3691, 1998.

Zhou, Halanski, Radonovich, Kashanchi, Peng, Price, Brady, "Tat modifies the activity of CDK9 to phosphorylate serine 5 of the RNA polymerase II carboxyl-terminal domain during human immunodeficiency virus type 1 transcription," *Mol. Cell Biol.*, 20:5077–5086, 2000.

Zhu, Pe'ery, Peng, Ramanathan, Marshall, Marshall, Amendt, Mathews, Price, "Transcription elongation factor P-TEFb is required for HIV-1 tat transactivation in vitro," *Genes Dev.*, 11:2622–2632, 1997.

What is claimed is:

1. A method for inhibiting P-TEFb, comprising contacting P-TEFb with an amount of an flavopiridol compound effective to inhibit said P-TEFb.

2. The method of claim 1, wherein said P-TEFb is comprised within a cell-free composition.

3. The method of claim 1, wherein said P-TEFb is comprised within a cell.

4. The method of claim 3, wherein said P-TEFb is comprised within an HIV-infected cell.

5. A method for inhibiting viral transcription, comprising providing to a system competent to perform viral transcription an amount of a flavopiridol compound effective to inhibit the cyclin-dependent kinase subunit of P-TEFb within said system, thereby inhibiting viral transcription.

6. The method of claim 5, wherein said viral transcription is HIV transcription.

7. A method for inhibiting viral replication or propagation in a mammalian cell, comprising providing a flavopiridol compound to a mammalian cell infected with a virus in an amount effective to inhibit P-TEFb within said cell, thereby inhibiting viral transcription, replication and propagation in said cell.

8. The method of claim 7, wherein said cell is infected with HIV.

9. The method of claim 7, wherein said cell is a mammalian cell located within a mammal and said flavopiridol is administered to said mammal.

10. The method of claim 7, wherein said cell is a human cell.

11. A method for inhibiting HIV replication or propagation in a patient, comprising providing a flavopiridol compound to a patient infected, or suspected of being infected, with HIV in an amount effective to inhibit P-TEFb within cells of said patient, thereby inhibiting HIV transcription, replication and propagation in said cells of said patient.

* * * * *

UNITED STATES PATENT AND TRADEMARK OFFICE
CERTIFICATE OF CORRECTION

PATENT NO. : 6,660,750 B2
DATED : December 9, 2003
INVENTOR(S) : Price et al.

It is certified that error appears in the above-identified patent and that said Letters Patent is hereby corrected as shown below:

<u>Title page,</u>
Item [73], Assignees, after "the" please insert -- Secretary of the --.

<u>Column 64,</u>
Line 36, after "flavopiridol" please insert -- compound --.

Signed and Sealed this

Third Day of February, 2004

JON W. DUDAS
*Acting Director of the United States Patent and Trademark Office*